(12) United States Patent
Weis et al.

(10) Patent No.: US 10,660,900 B2
(45) Date of Patent: May 26, 2020

(54) METHODS AND COMPOSITIONS FOR POTENTIATING THE ACTION OF OPIOID ANALGESICS USING IBOGA ALKALOIDS

(71) Applicant: DemeRx, Inc., Fort Lauderdale, FL (US)

(72) Inventors: Holger Weis, Fort Lauderdale, FL (US); Emeline Maillet, Miami Beach, FL (US)

(*) Notice: Subject to any disclaimer, the term of this patent is extended or adjusted under 35 U.S.C. 154(b) by 0 days.

(21) Appl. No.: 15/093,717

(22) Filed: Apr. 7, 2016

(65) Prior Publication Data
US 2016/0220579 A1    Aug. 4, 2016

Related U.S. Application Data

(63) Continuation-in-part of application No. PCT/US2015/062783, filed on Nov. 25, 2015.

(60) Provisional application No. 62/084,979, filed on Nov. 26, 2014, provisional application No. 62/119,021, filed on Feb. 20, 2015, provisional application No. 61/996,996, filed on Apr. 7, 2015.

(51) Int. Cl.
| | |
|---|---|
| *A61K 31/55* | (2006.01) |
| *A61K 36/24* | (2006.01) |
| *A61K 31/485* | (2006.01) |
| *A61K 31/4468* | (2006.01) |
| *A61K 31/4025* | (2006.01) |
| *A61K 31/439* | (2006.01) |
| *A61K 31/137* | (2006.01) |
| *A61K 31/135* | (2006.01) |
| *A61K 31/4535* | (2006.01) |

(52) U.S. Cl.
CPC ............ *A61K 31/55* (2013.01); *A61K 31/135* (2013.01); *A61K 31/137* (2013.01); *A61K 31/4025* (2013.01); *A61K 31/439* (2013.01); *A61K 31/4468* (2013.01); *A61K 31/4535* (2013.01); *A61K 31/485* (2013.01); *A61K 36/24* (2013.01)

(58) Field of Classification Search
None
See application file for complete search history.

(56) References Cited

U.S. PATENT DOCUMENTS

| | | | |
|---|---|---|---|
| 2,817,623 | A | 12/1957 | Schneider |
| 4,626,539 | A | 12/1986 | Aungst et al. |
| 4,806,341 | A | 2/1989 | Chien et al. |
| 5,149,538 | A | 9/1992 | Granger et al. |
| 5,591,738 | A | 1/1997 | Lotsof |
| 5,616,575 | A | 4/1997 | Efange et al. |
| 6,348,456 | B1 | 2/2002 | Mash et al. |
| 6,416,793 | B1 | 7/2002 | Zeligs et al. |
| 6,933,308 | B2 | 8/2005 | Boy et al. |
| 7,220,737 | B1 | 5/2007 | Mash |
| 7,754,710 | B2 | 7/2010 | Mash |
| 8,178,524 | B2 | 5/2012 | Mash |
| 8,362,007 | B1 | 1/2013 | Mash et al. |
| 8,637,648 | B1 | 1/2014 | Mash et al. |
| 8,648,198 | B2 | 2/2014 | Furukawa et al. |
| 8,741,891 | B1 | 6/2014 | Mash |
| 8,742,096 | B2 | 6/2014 | Moriarty et al. |
| 8,765,737 | B1 | 7/2014 | Mash et al. |
| 8,853,201 | B2 | 10/2014 | Gless et al. |
| 8,940,728 | B2 | 1/2015 | Mash et al. |
| 9,045,481 | B2 | 6/2015 | Mash et al. |
| 9,308,272 | B2 | 4/2016 | Mash et al. |
| 2003/0153552 | A1 | 8/2003 | Mash et al. |
| 2003/0194438 | A1 | 10/2003 | Prescott et al. |
| 2006/0229293 | A1 | 10/2006 | Lotsof |
| 2007/0185085 | A1 | 8/2007 | Mash |
| 2010/0311722 | A1 | 12/2010 | Mash |
| 2010/0311723 | A1 | 12/2010 | Mash |
| 2010/0311725 | A1 | 12/2010 | Mash |
| 2012/0083485 | A1 | 4/2012 | Mash |
| 2012/0253037 | A1 | 10/2012 | Moriarty et al. |
| 2013/0011444 | A1 | 1/2013 | Zebala |
| 2013/0072472 | A1 | 3/2013 | Gless et al. |
| 2013/0131046 | A1 | 5/2013 | Moriarty et al. |
| 2013/0165414 | A1 | 6/2013 | Gless et al. |
| 2013/0165425 | A1 | 6/2013 | Gless et al. |
| 2013/0165647 | A1 | 6/2013 | Moriarty et al. |
| 2013/0211073 | A1 | 8/2013 | Moriarty |
| 2013/0211074 | A1 | 8/2013 | Moriarty |
| 2013/0296823 | A1 | 11/2013 | Melker et al. |
| 2013/0303756 | A1 | 11/2013 | Mash et al. |
| 2013/0311725 | A1 | 11/2013 | Greenhalgh |
| 2014/0179685 | A1 | 6/2014 | Mash et al. |
| 2014/0187655 | A1 | 7/2014 | Mash et al. |

(Continued)

FOREIGN PATENT DOCUMENTS

| | | |
|---|---|---|
| WO | WO-96/03127 A1 | 2/1996 |
| WO | WO-99/11250 | 3/1999 |

(Continued)

OTHER PUBLICATIONS

International Search Report and Written Opinion for related application No. PCT/US2016/031932, dated Dec. 12, 2016.

(Continued)

*Primary Examiner* — Brian J Davis
(74) *Attorney, Agent, or Firm* — Mintz Levin Cohn Ferris Glovsky and Popeo PC

(57) ABSTRACT

Methods and compositions for potentiating the effect of an opioid analgesic in a patient undergoing or planning to undergo opioid analgesic therapy using a potentiating amount of iboga alkaloid or pharmaceutically acceptable salt and/or solvate thereof that does not prolong the patient's QT interval by more than about 50 milliseconds.

2 Claims, 20 Drawing Sheets

(56) References Cited

U.S. PATENT DOCUMENTS

| | | |
|---|---|---|
| 2014/0288056 A1 | 9/2014 | Friedhoff |
| 2014/0315891 A1 | 10/2014 | Mash |
| 2014/0357741 A1 | 12/2014 | Mash et al. |
| 2015/0045350 A1 | 2/2015 | Friedhoff |
| 2015/0231145 A1 | 8/2015 | Friedhoff |
| 2015/0231146 A1 | 8/2015 | Friedhoff |
| 2015/0238503 A1 | 8/2015 | Maillet et al. |
| 2015/0246055 A1 | 9/2015 | Friedhoff |
| 2015/0257667 A1 | 9/2015 | Friedhoff |
| 2015/0258105 A1 | 9/2015 | Maillet et al. |
| 2015/0258106 A1 | 9/2015 | Friedhoff |
| 2015/0258107 A1 | 9/2015 | Friedhoff |
| 2015/0258108 A1 | 9/2015 | Maillet et al. |
| 2015/0258111 A1 | 9/2015 | Maillet et al. |
| 2015/0258113 A1 | 9/2015 | Friedhoff |
| 2015/0258114 A1 | 9/2015 | Friedhoff |
| 2015/0342959 A1 | 12/2015 | Friedhoff |
| 2016/0008372 A1 | 1/2016 | Weis |
| 2016/0038508 A1 | 2/2016 | Perry et al. |
| 2016/0220579 A1 | 8/2016 | Weis et al. |

FOREIGN PATENT DOCUMENTS

| | | |
|---|---|---|
| WO | WO-2012/012764 A1 | 1/2012 |
| WO | WO-2012/103028 | 8/2012 |
| WO | WO-2012/135047 | 10/2012 |
| WO | WO-2013/040471 | 3/2013 |
| WO | WO-2013/085849 A2 | 6/2013 |
| WO | WO-2013/085922 A1 | 6/2013 |
| WO | WO-2013/112622 | 8/2013 |
| WO | WO-2013/112673 | 8/2013 |
| WO | WO-2014/019692 | 2/2014 |
| WO | WO-2014/143201 | 9/2014 |
| WO | WO-2014/144508 | 9/2014 |
| WO | WO-2015/126434 | 8/2015 |
| WO | WO-2015/126836 | 8/2015 |
| WO | WO-2015/163844 | 10/2015 |
| WO | WO-2015/195673 | 12/2015 |
| WO | WO-2016/086194 | 6/2016 |
| WO | WO-2016/134019 | 8/2016 |

OTHER PUBLICATIONS

Cubeddu "QT Prolongation and Fatal Arrhythmias: A Review of Clinical Implications and Effects of Drugs",American Journal of Therapeutics 10, pp. 452-457, 2003.
Malik et al., "Evaluation of Drug-Induced QT Interval Prolongation," Drug Safety, 2001, 24(5), pp. 323-351.
Mash et al., Annals of the New York Academy of Sciences, 2000, vol. 914, pp. 394-401.
Sala et al. "QT Interval Prolongation related to psychoactive drug treatment: a comparison of monotherapy versus polytherapy", Ann Gen Psychiatry 2005; 4(1):1.
Australian New Zealand Clinical Trials Registry ACTRN12612000821897, 2012.
Bhargava, et al., "Effects of noribogaine on the development of tolerance to antinociceptive action of morphine in mice," Brain Research, (1997) 771:343-346.
Bhargava, et al., "Effects of ibogaine and noribogaine on the antinociceptive action of μ-, δ- and κ-opioid receptor agonists in mice," Brain Research, (1997), 752:234-238.
Breen, et al. "Cessation of Methadone Maintenance Treatment Using Buprenorphine: transfer from methadone to buprenorphine and subsequent buprenorphine reductions," Drug and Alcohol Dependence, 71, (2003) 49-55.
Calsyn et al., "Slow tapering from methadone maintenance in a program encouraging indefinite maintenance," Journal of Substance Abuse Treatment, (2006), 30:159-163.
Cao, et al., "Effects of ibogaine on the development of tolerance to antinociceptive action of μ-, δ- and κ-opioid receptor agonists in mice," Brain Research, (1997), 752:250-254.

Chang et al. "Noribogaine reduces nicotine self-administration in rats," Journal of Pyschopharmacology, May 20, 2015 (May 20, 2015), vol. 29, No. 6, pp. 704-711.
Donnelly, J.R., "The Need for Ibogaine in Drug and Alcohol Addiction Treatment," Journal of Legal Medicine, (2011), 32:93-114.
Eap et al., "Interindividual Variability of the Clinical Pharmacokinetics of Methadone," Clinical Pharmacokinetics, (2002), 41(14):1153-1193.
Fermini et al., Nature Reviews Drug Discovery 2003, 2, 439-447.
Goutarel, et al., "Pharmacodynamics and Therapeutic Applications of Iboga and Ibogaine," Psychedelic Monographs and Essays, vol. 6:70-111, 1993.
Hoelen et al., Long-QT Syndrome Induced by the Antiaddiction Drug Ibogaine, Jan. 15, 2009, N Engl J Med, 360(3), pp. 308-309.
Huffman, et al., "A Formal Synthesis of (±)-Ibogamine", J. Org. Chem., (1985), 50:1460-1464.
International Preliminary Report on Patentability dated Sep. 24, 2015 for PCT Application No. PCT/US2014/028946.
International Preliminary Report on Patentability for PCT/US2013/069235, dated Sep. 24, 2015.
International Search Report and Written Opinion Application No. PCT/US2015/062783, dated Feb. 9, 2016, 16 pages.
Khan et al., "Long QT syndrome: Diagnosis and management", American Heart Journal, 2002, 143(1):7-14.
Krantz et al., "QTc Interval Screen in Methadone Treatment," Annals of Internal Medicine, 2009, American College of Physicians, vol. 150, pp. 387-395.
Kroupa, et al., "Ibogaine in the 21st Century: Boosters, Tune-ups and Maintenance," MAPS, (2005), 15(1):21-24.
Kubiliene, et al., "Acute toxicity of ibogaine and noribogaine," Medicina (Kaunas), (2008), 44(12):984-988.
Maillet et al., "Noribogaine is a G-protein biased k-opioid receptor agonist", Neuropharmacology, 2015, 99, pp. 675-688.
Mitchell et al., "Temperature and the cold pressor test", J. Pain, 2004, 5:233-237.
New Zealand Ministry of Health, Prescriber Update (2010), 31(4), pp. 27-29.
PCT International Preliminary Report on Patentability for PCT Patent Application No. PCT/US14/19692, dated Feb. 1, 2016. 19 pages.
PCT International Search Report and Written Opinion, dated Jun. 10, 2016, in related PCT Patent Application No. PCT/US16/18273.
PCT International Search Report and Written Opinion, dated Mar. 10, 2014, in related PCT Patent Application No. PCT/US13/69235.
PCT International Search Report and Written Opinion for Appl No. PCT/US2015/016186, dated Apr. 24, 2015.
PCT International Search Report and Written Opinion for Appl. No. PCT/US2014/019692, dated Nov. 18, 2014.
PCT International Search Report and Written Opinion for Appl. No. PCT/US2014/028946, dated Jul. 28, 2014.
Pearl et al., "Radioligand-binding Study of Noribogaine, A Likely Metabolite of Ibogaine", Brain Research, 1995, 675:342-344.
Popik et. al., "100 Years of Ibogaine: Neurochemical and Pharmacological Actions of a Putative Anti-addictive Drug," Pharmacological Reviews (1995)47:235:253.
Sharma et. al. "Enhancement of Morphine Antinociception by Ibogaine and Noribogaine in Morphine-tolerant Mice," Pharmacology (1998) 57:229-232.
Stichering, et al., "Christian, Methadone-induced Torsade de pointes tachycardias," Swiss Med Wkly, 2005; vol. 135, pp. 282-285.
Weiss et al., "Neurobiology of craving, conditioned reward and relapse", Current Opinion in Pharmacology, 2005, 5:9-19.
Zubaran et a., "Noribogaine Generalization to the Ibogaine Stimulus: Correlation with Noribogaine Concentration in Rat Brain", Neuropsychopharmacology, 1999, vol. 21, pp. 119-126.
Ward J, et al. Herbal Medicines for the Management of Opioid Addiction. CNS Drugs, 2011;25(12):999-1007.
Mass U, Strubelt S. Fatalities after taking ibogaine in addiction treatment could be related to sudden cardiac death caused by autonomic dysfunction. Medical Hypotheses, 2006;67:960-964.

Box includes values representing 25% - 75% quartiles. Diamond = median; crossbar in box = mean; whiskers = values within standard deviation of mid-quartiles. No outliers present.

- Charged (negative)
- Polar
- Hydrophobic
- Water
- π-π stacking
- π-cation
- H-bond (backbone)
- H-bond (side chain)

METHODS AND COMPOSITIONS FOR POTENTIATING THE ACTION OF OPIOID ANALGESICS USING IBOGA ALKALOIDS

CROSS-REFERENCE TO RELATED APPLICATIONS

This application is a continuation-in-part of PCT Application No. PCT/US2015/062783, filed Nov. 25, 2015, which claims the benefit under 35 U.S.C. 119(e) of U.S. Provisional Application Ser. No. 62/084,979 filed Nov. 26, 2014; 62/119,021 filed Feb. 20, 2015; and 61/996,996 filed Apr. 7, 2015, each of which is hereby incorporated by reference into this application in its entirety.

FIELD OF THE INVENTION

This invention is directed to methods and compositions for potentiating the effect of opioids in a patient undergoing or planning to undergo opioid analgesic treatment for pain. In particular the methods and compositions include treating the patient with an analgesic opioid or derivative thereof in combination with a potentiating amount of an iboga alkaloid or pharmaceutically acceptable salt or solvate thereof at a safe and effective dosage. In particular the potentiating amount of the iboga alkaloid or pharmaceutically acceptable salt or solvate thereof is such that the maximum QT interval prolongation experienced by the patient is less than about 60 ms, less than about 50 ms, preferably less than about 30 ms, more preferably less than about 20 ms.

STATE OF THE ART

Addictive opioid analgesic agents including derivatives thereof (e.g. morphine, hydromorphone) are well-known and exceptionally potent analgesics. Such opioids operate as mu receptor agonists. Upon administration, opioids initiate a cascade of biological events including increased serotonin and dopamine expression. As is well known, continued use of many such opioids (especially at high doses) carries a significant risk of dependency/addiction. Indeed, potential addiction to such opioids is a serious issue that limits the therapeutic use of addictive opioids as analgesic agents. For example, the use of morphine as an analgesic is common among end stage patients suffering from serious pain where addiction is no longer a concern.

Drug tolerance to opioid analgesics is common, and may be psychological and/or physiological. A patient who has developed tolerance to the opioid analgesic is not necessarily addicted to or misusing the analgesic. Drug tolerance occurs when the patient's reaction to the drug is reduced, requiring an increase in dose to achieve the same desired effect. There are several potential methods for how tolerance develops, including receptor desensitization, receptor phosphorylation, receptor internalization or down-regulation, and up-regulation of inhibitory pathways.

Drug tolerance requires that the dosage of analgesic be increased in order to provide sustained analgesic effect. However, high doses of opioids may lead to serious complications and side effects, including physical dependence, addiction, respiratory depression, nausea, sedation, euphoria or dysphoria, decreased gastrointestinal motility, and itching.

Furthermore, opioid use is associated with a number of unpleasant side effects. Side effects include sedation, dizziness, nausea, vomiting, constipation, and respiratory depression.

It would be beneficial to provide a method for potentiating the effect of opioid analgesic(s) in a patient taking one or more opioid analgesics for the treatment of pain, such that a lower dose of opioid is required to treat the pain.

SUMMARY OF THE INVENTION

This invention is directed, in part, to the use of an iboga alkaloid to potentiate the activity of opioid analgesic agents in a patient taking one or more opioid analgesics wherein the iboga alkaloid is dosed in an amount to potentiate the opioid while maintaining an acceptable QT interval prolongation. Potentiation of the opioid analgesic may be characterized by a number of parameters, including but not limited to: a decrease in the amount of opioid analgesic required to treat a similar pain level; improved therapeutic effect from a specified dose of opioid analgesic, a reduced tolerance to the opioid analgesic; reduced dependency on the opioid analgesic; reduced risk of tolerance to the opioid analgesic; or reduced risk of dependency on the opioid analgesic.

The use of morphine in combination with iboga alkaloids has been disclosed in non-human subjects such that it did not evaluate the QT interval prolongation, nor were dosing regimens addressed that affect potentiation while maintaining an acceptable QT prolongation. This invention is based, at least on part, on the surprising discovery that iboga alkaloids, e.g. noribogaine, can be administered to a patient at a dose that potentiates opioid analgesic action while also minimizing the risk of unsafe QT interval prolongation by the iboga alkaloid.

In one embodiment, the patient has developed or is at risk of developing a tolerance for the analgesic. In a preferred embodiment, the patient has not yet developed a tolerance to the opioid analgesic. In one embodiment, the iboga alkaloid is administered throughout opioid treatment. In one embodiment, the iboga alkaloid is administered after tolerance (or suspected tolerance) to the opioid has occurred. In an especially preferred embodiment, the patient is naïve to the opioid analgesic, i.e., the patient has not been administered an opioid analgesic for a period of time such that any residual opioid in the blood stream is less than an amount to impart an analgesic effect to the patient. Preferably, the patient has not been administered an opioid analgesic within two weeks and preferably within four weeks prior to administration of iboga alkaloid in combination with an opioid analgesic.

In one embodiment, administration of the iboga alkaloid inhibits tolerance to the opioid analgesic in the opioid-treated patient wherein the iboga alkaloid is dosed in an amount to potentiate the opioid while maintaining an acceptable QT interval prolongation. As used herein, the term "inhibits tolerance to the opioid analgesic" includes one or more of the following:

the administration of the iboga alkaloid reduces tolerance to the opioid analgesic;

the administration of the iboga alkaloid increases the amount of time for the patient to become tolerant to the opioid analgesic;

the administration of the iboga alkaloid increases the dose of opioid analgesic at which tolerance to the opioid occurs; and/or the administration of the iboga alkaloid resensitizes the patient to the opioid.

Pain has physical manifestations, but can also include psychological and emotional factors. The methods and compositions described herein are related to treatment of physical manifestations of pain.

In one embodiment, the dose of opioid analgesic that is administered to the patient is reduced relative to the dose prior to iboga alkaloid administration, wherein the iboga alkaloid is dosed in an amount to potentiate the opioid while maintaining an acceptable QT interval prolongation. In one embodiment, the dose of opioid analgesic that is administered to the patient is reduced relative to the dose that would have been administered in the absence of iboga alkaloid administration.

In one embodiment, gradient doses of the iboga alkaloid and opioid analgesic are administered to the patient. In some embodiments, the dosage of iboga alkaloid is incrementally increased with a concomitant decrease in the opioid analgesic dosage. Patients undergoing such gradient dosing procedures may be monitored by a clinician to ensure potentiation of the opioid while maintaining an acceptable QT interval prolongation. The clinician may also monitor for unacceptable respiratory depression. Analysis of a suitable dosage is well within the skill of the art based on the teachings provided herein, taking into account the age, weight and condition of the patient as well as other well known factors.

In one embodiment, effective analgesia can be achieved in a patient while resensitizing the patient to the addictive opioid analgesic. The term "resensitizing the patient" is used herein to refer to reducing, relieving, attenuating, and/or reversing tolerance to the analgesic. In one embodiment, the resensitized patient obtains therapeutic effect from a lower dose of the opioid analgesic than before resensitization. In one embodiment, the resensitized patient obtains improved therapeutic effect from the same dose of the opioid analgesic compared to before resensitization.

In one embodiment, it is contemplated that co-administration of the iboga alkaloid with the opioid prevents, inhibits or attenuates dependence on and/or addiction to the opioid analgesic, wherein the iboga alkaloid is dosed in an amount to potentiate the opioid while maintaining an acceptable QT interval prolongation. In one embodiment, it is contemplated that administration of the iboga alkaloid increases the amount of time for the patient to become dependent on and/or addicted to the opioid analgesic. In one embodiment, it is contemplated that administration of the iboga alkaloid increases the dose of opioid analgesic at which dependence and/or addiction to the opioid occurs. In one embodiment, it is contemplated that potentiation of the effect of the opioid analgesic allows less of the opioid to be administered to the patient, further reducing the probability of dependence or addiction (e.g., abuse liability) to the opioid analgesic.

It has been discovered that the use of iboga alkaloids, derivatives, or pharmaceutically acceptable salts and/or solvates thereof imparts a dose-dependent prolongation of the treated patient's QT interval, rendering higher dosing of such alkaloids (e.g., noribogaine) unacceptable. A prolonged QT interval can lead to Torsades de Pointes, a serious arrhythmia that can result in death. In a preferred embodiment of the methods and compositions of this invention, the amount of iboga alkaloids required to achieve one or more of the benefits enumerated above is limited such that the patient's QT interval is not prolonged or by more than about 60 milliseconds (ms), preferably not by more than 50 ms, and most preferably not by more than 30 ms.

The current invention is predicated on the surprising discovery that the use of an iboga alkaloid or pharmaceutically acceptable salt and/or solvate thereof at a dosage that is below that considered effective for treatment of opioid addiction provides a therapeutic potentiation of opioid analgesics and exhibits a dose-dependent QT interval prolongation. This low dose of iboga alkaloid imparts minimal QT interval prolongation while also reducing the risk of tolerance and/or addiction to opioid analgesics. Preferably, the dose range that provides both therapeutic results and an acceptable QT interval prolongation of less than about 60 milliseconds, less than about 50 milliseconds, less than about 30 milliseconds, or less than about 20 milliseconds is between about 0.05 mg and about 50 mg per day, or any subrange or subvalue within the range.

In some embodiments, the ratio of opioid analgesic to iboga alkaloid or pharmaceutically acceptable salt and/or solvate thereof administered to the patient is between 100:1 and 1:100. In one embodiment, the ratio of opioid analgesic to iboga alkaloid or pharmaceutically acceptable salt and/or solvate thereof is between 100:1 and 1:50. In one embodiment, the ratio of opioid analgesic to iboga alkaloid or pharmaceutically acceptable salt and/or solvate thereof is between 100:1 and 1:10. In one embodiment, the ratio of opioid analgesic to iboga alkaloid or pharmaceutically acceptable salt and/or solvate thereof is between 100:1 and 1:1.

Without being bound by theory, it is believed that co-administration of iboga alkaloid with an opioid as described herein will result in potentiation of the effect of the opioid with fewer negative side effects, reduced tolerance to the opioid, and/or a lower rate of dependence and/or addiction to the opioid compared to opioid administration without the iboga alkaloid.

In one embodiment, the iboga alkaloid or pharmaceutically acceptable salt and/or solvate thereof is administered concurrently with the opioid analgesic, wherein the iboga alkaloid is dosed in an amount effective to potentiate the opioid while maintaining an acceptable QT interval prolongation. In one embodiment, a composition comprising an iboga alkaloid or salt and/or solvate thereof and the opioid analgesic is administered. Such a combination of both the iboga alkaloid and the analgesic eliminates the possibility that the patient will self-administer one drug but not the other. It is further contemplated that such a combination will reduce the abuse potential of the opioid analgesic.

Alternatively, in another embodiment such as a clinical setting, the iboga alkaloid or pharmaceutically acceptable salt and/or solvate thereof is administered before or after administration of the analgesic, wherein the iboga alkaloid is dosed in an amount effective to potentiate the opioid while maintaining an acceptable QT interval prolongation. For example, either drug can be administered one, two, three, four, eight, ten, twelve, 24 hours or more after administration of the remaining drug. In one embodiment, one dose of iboga alkaloid is administered. In one embodiment, two or more doses of iboga alkaloid are administered.

In one embodiment, the amount of iboga alkaloid administered per day is increased or decreased over time depending upon factors such as the amount of opioid analgesic administered, the weight, age and condition of the patient, and other factors well within the skill of the attending clinician, wherein the amount of iboga alkaloid potentiates the opioid while maintaining an acceptable QT interval prolongation. In one embodiment, the duration of iboga alkaloid treatment is less than about four weeks. In one embodiment, the patient ceases iboga alkaloid administration for a period of time (e.g., between two days and about three weeks) before restarting the iboga alkaloid treatment.

In some embodiments, the therapeutic dose of iboga alkaloid or pharmaceutically acceptable salt and/or solvate thereof administered to the patient is an amount sufficient to achieve one or more of the benefits set forth above and preferably results in an average serum concentration of no more than about 100 ng/mL, wherein the dose of iboga alkaloid is an amount that potentiates the opioid while maintaining an acceptable QT interval prolongation. In a preferred embodiment, the dose of iboga alkaloid or pharmaceutically acceptable salt and/or solvate thereof administered to the patient provides an average serum concentration of no more than about 50 ng/mL.

In one embodiment, the dose of iboga alkaloid or pharmaceutically acceptable salt and/or solvate thereof administered to the patient provides a serum concentration of no more than about 10,000 ng*hour/mL (area under the curve for a period of time, AUC/t) over the period during which the iboga alkaloid is administered, wherein the dose of iboga alkaloid is an amount that potentiates the opioid while maintaining an acceptable QT interval prolongation. The period of treatment may be between about one day and about three weeks or longer. In a preferred embodiment, the period of treatment is about two weeks to about three weeks. In some embodiments, the iboga alkaloid or pharmaceutically acceptable salt and/or solvate thereof is administered as long as the opioid analgesic is administered.

In one embodiment, a patient undergoing opioid analgesic treatment for pain is administered a gradient dosage of iboga alkaloid or pharmaceutically acceptable salt and/or solvate thereof over a course of time. In one embodiment, the gradient dose is an increasing dose of iboga alkaloid. In one embodiment, the gradient dose is a decreasing dose of iboga alkaloid. The patient may be monitored by a skilled clinician to ensure the iboga alkaloid is dosed in an amount to potentiate the opioid while maintaining an acceptable QT interval prolongation and without a resultant respiratory depression.

DETAILED DESCRIPTION OF THE INVENTION

Figure 1:
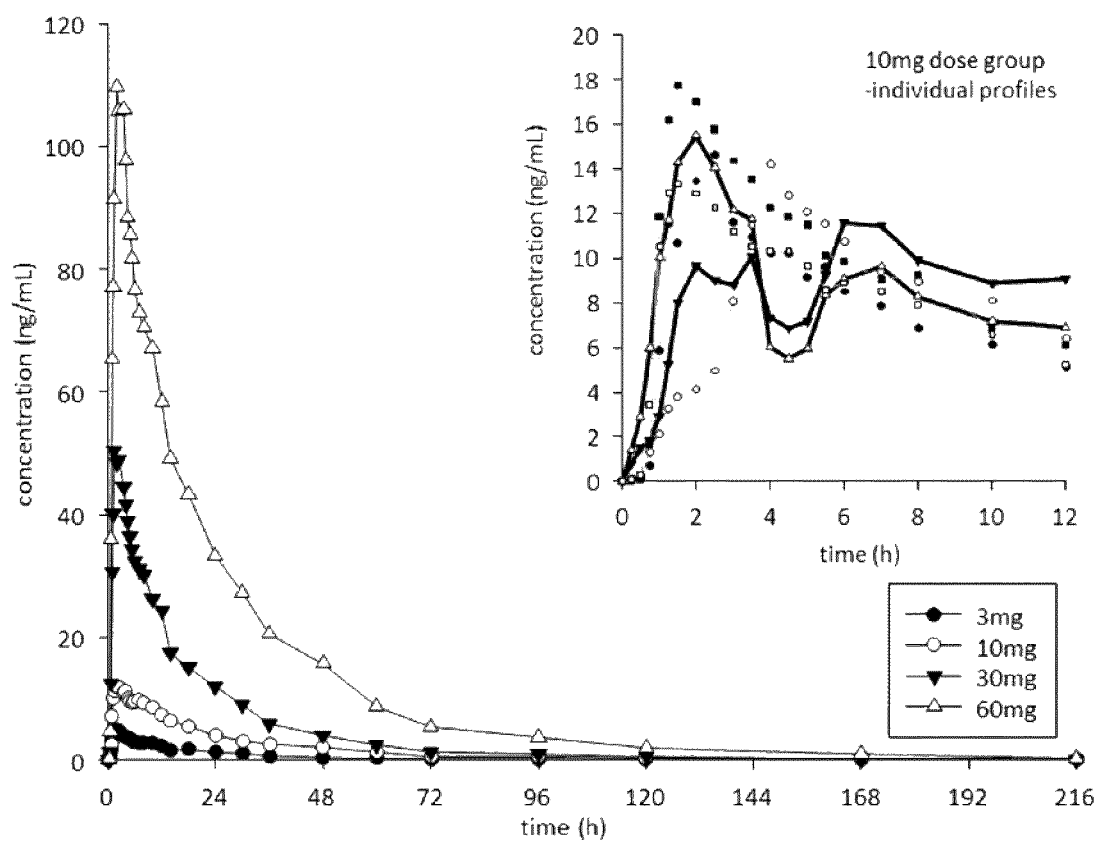
FIG. 1 represents mean noribogaine concentration-time profiles in healthy patients after single oral dosing with 3 mg (●), 10 mg (○), 30 mg (▼) or 60 mg (Δ) doses. Inset: Individual concentration-time profiles from 0-12 h after a 10 mg dose.

It is to be understood that this invention is not limited to particular embodiments described, as such may, of course, vary. It is also to be understood that the terminology used herein is for the purpose of describing particular embodiments only, and is not intended to be limiting, since the scope of this invention will be limited only by the appended claims.

The detailed description of the invention is divided into various sections only for the reader's convenience and disclosure found in any section may be combined with that in another section. Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. Thus, for example, reference to "a compound" includes a plurality of compounds.

I. Definitions

Unless defined otherwise, all technical and scientific terms used herein have the same meaning as commonly understood by one of ordinary skill in the art to which this invention belongs. As used herein the following terms have the following meanings.

The term "about" when used before a numerical designation, e.g., temperature, time, amount, concentration, and such other, including a range, indicates approximations which may vary by (+) or (−) 10%, 5% or 1%.

"Administration" refers to introducing an agent into a patient. Typically, an effective amount is administered, which amount can be determined by the treating physician or the like. Any route of administration, such as oral, topical, subcutaneous, peritoneal, intra-arterial, inhalation, vaginal, rectal, nasal, introduction into the cerebrospinal fluid, or instillation into body compartments can be used. The agent may be administered by direct blood stream delivery, e.g. sublingual, intranasal, or intrapulmonary administration.

The related terms and phrases "administering" and "administration of", when used in connection with a compound or pharmaceutical composition (and grammatical equivalents) refer both to direct administration, which may be administration to a patient by a medical professional or by self-administration by the patient, and/or to indirect administration, which may be the act of prescribing a drug. For example, a physician who instructs a patient to self-administer a drug and/or provides a patient with a prescription for a drug is administering the drug to the patient. In addition, "concomitant administration" refers to either simultaneous administration or administration proximate in time whereby both drugs are therapeutically active in the patient.

"Periodic administration" or "periodically administering" refers to multiple treatments that occur on a daily, weekly, or monthly basis. Periodic administration may also refer to administration of the iboga alkaloid or salt and/or solvate thereof one, two, three, or more times per day. Administration may be via transdermal patch, gum, lozenge, sublingual tablet, intranasal, intrapulmonary, oral administration, or other administration.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

As used herein, the term "alkyl" refers to monovalent saturated aliphatic hydrocarbyl groups having from 1 to 12 carbon atoms, 1 to 10 carbon atoms, preferably 1 to 6 carbon atoms, and more preferably 1 to 3 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—). The term "$C_x$ alkyl" refers to an alkyl group having x carbon atoms, wherein x is an integer, for example, $C_3$ refers to an alkyl group having 3 carbon atoms.

"Alkenyl" refers to straight or branched hydrocarbyl groups having from 2 to 6 carbon atoms and preferably 2 to 4 carbon atoms and having at least 1 and preferably from 1 to 2 sites of vinyl (>C=C<) unsaturation. Such groups are exemplified, for example, by vinyl, allyl, and but-3-en-1-yl. Included within this term are the cis and trans isomers or mixtures of these isomers.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—CH$_2$C≡CH).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein and with the proviso that any hydroxy or thiol substitution is not attached to a vinyl (unsaturated) carbon atom.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein and with the proviso that any hydroxy or thiol substitution is not attached to an acetylenic carbon atom.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Acyl includes the "acetyl" group $CH_3C(O)$—.

"Acylamino" refers to the groups —$NR^{38}$C(O)alkyl, —$NR^{38}$C(O)substituted alkyl, —$NR^{38}$C(O)cycloalkyl, —$NR^{38}$C(O)substituted cycloalkyl, —$NR^{38}$C(O)cycloalkenyl, —$NR^{38}$C(O)substituted cycloalkenyl, —$NR^{38}$C(O)alkenyl, —$NR^{38}$C(O)substituted alkenyl, —$NR^{38}$C(O)alkynyl, —$NR^{38}$C(O)substituted alkynyl, —$NR^{38}$C(O)aryl, —$NR^{38}$C(O)substituted aryl, —$NR^{38}$C(O)heteroaryl, —$NR^{38}$C(O)substituted heteroaryl, —$NR^{38}$C(O)heterocyclic, and —$NR^{38}$C(O)substituted heterocyclic wherein $R^{38}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group —$NH_2$.

"Substituted amino" refers to the group —$NR^{39}R^{40}$ where $R^{39}$ and $R^{40}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-cycloalkenyl, —$SO_2$-substituted cylcoalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic and wherein $R^{39}$ and $R^{40}$ are optionally joined, together with the nitrogen bound thereto to form a heterocyclic or substituted heterocyclic group, provided that $R^{39}$ and $R^{40}$ are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When $R^{39}$ is hydrogen and $R^{40}$ is alkyl, the substituted amino group is sometimes referred to herein as alkylamino. When $R^{39}$ and $R^{40}$ are alkyl, the substituted amino group is sometimes referred to herein as dialkylamino. When referring to a monosubstituted amino, it is meant that either $R^{39}$ or $R^{40}$ is hydrogen but not both. When referring to a disubstituted amino, it is meant that neither $R^{39}$ nor $R^{40}$ are hydrogen.

"Aminocarbonyl" refers to the group —C(O)$NR^{41}R^{42}$ where $R^{41}$ and $R^{42}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{41}$ and $R^{42}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonyl" refers to the group —C(S)$NR^{41}R^{42}$ where $R^{41}$ and $R^{42}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{41}$ and $R^{42}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —$NR^{38}$C(O)$NR^{41}R^{42}$ where $R^{38}$ is hydrogen or alkyl and $R^{41}$ and $R^{42}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{4'}$ and $R^{42}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonylamino" refers to the group —$NR^{38}$C(S)$NR^{41}R^{42}$ where $R^{38}$ is hydrogen or alkyl and $R^{41}$ and $R^{42}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{41}$ and $R^{42}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyloxy" refers to the group —O—C(O)$NR^{41}R^{42}$ where $R^{41}$ and $R^{42}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{41}$ and $R^{42}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyl" refers to the group —$SO_2NR^{41}R^{42}$ where $R^{41}$ and $R^{42}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{41}$ and $R^{42}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyloxy" refers to the group —O—$SO_2NR^{41}R^{42}$ where $R^{41}$ and $R^{42}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{41}$ and $R^{42}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonylamino" refers to the group —$NR^{38}$—$SO_2NR^{41}R^{42}$ where $R^{38}$ is hydrogen or alkyl and $R^{41}$ and $R^{42}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{41}$ and $R^{42}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amidino" refers to the group —C(=$NR^{43}$)$NR^{41}R^{42}$ where $R^{41}$, $R^{42}$, and $R^{43}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{41}$ and $R^{42}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Carbonyl" refers to the divalent group —C(O)— which is equivalent to —C(=O)—.

"Carboxy" or "carboxyl" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino" refers to the group —NR$^{38}$—C(O)O-alkyl, —NR$^{38}$—C(O)O-substituted alkyl, —NR$^{38}$—C(O)O-alkenyl, —NR$^{38}$—C(O)O-substituted alkenyl, —NR$^{38}$—C(O)O-alkynyl, —NR$^{38}$—C(O)O-substituted alkynyl, —NR$^{38}$—C(O)O-aryl, —NR$^{38}$—C(O)O-substituted aryl, —NR$^{38}$—C(O)O-cycloalkyl, —NR$^{38}$—C(O)O-substituted cycloalkyl, —NR$^{38}$—C(O)O-cycloalkenyl, —NR$^{38}$—C(O)O-substituted cycloalkenyl, —NR$^{38}$—C(O)O-heteroaryl, —NR$^{38}$—C(O)O-substituted heteroaryl, —NR$^{38}$—C(O)O-heterocyclic, and —NR$^{38}$—C(O)O-substituted heterocyclic wherein R$^{38}$ is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, substituted —O—C(O)O-alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" refers to the group —CN.

"Cycloalkyl" refers to cyclic alkyl groups of from 3 to 10 carbon atoms having single or multiple cyclic rings including fused, bridged, and spiro ring systems. One or more of the rings can be aryl, heteroaryl, or heterocyclic provided that the point of attachment is through the non-aromatic, non-heterocyclic ring carbocyclic ring. Examples of suitable cycloalkyl groups include, for instance, adamantyl, cyclopropyl, cyclobutyl, cyclopentyl, and cyclooctyl. Other examples of cycloalkyl groups include bicycle[2,2,2,]octanyl, norbornyl, and spirobicyclo groups such as spiro[4.5]dec-8-yl.

"Cycloalkenyl" refers to non-aromatic cyclic alkyl groups of from 3 to 10 carbon atoms having single or multiple cyclic rings and having at least one >C=C< ring unsaturation and preferably from 1 to 2 sites of >C=C< ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

"Cycloalkyloxy" refers to —O-cycloalkyl.

"Substituted cycloalkyloxy" refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy" refers to —O-(substituted cycloalkenyl).

"Cycloalkenylthio" refers to —S-cycloalkenyl.

"Substituted cycloalkenylthio" refers to —S-(substituted cycloalkenyl).

"Guanidino" refers to the group —NHC(=NH)NH$_2$.

"Substituted guanidino" refers to —NR$^{44}$C(=NR$^{44}$)N(R$^{44}$)$_2$ where each R$^{44}$ is independently selected from the group consisting of hydrogen, alkyl, substituted alkyl, aryl, substituted aryl, heteroaryl, substituted heteroaryl, heterocyclic, and substituted heterocyclic and two R$^{44}$ groups attached to a common guanidino nitrogen atom are optionally joined together with the nitrogen bound thereto to form a heterocyclic or substituted heterocyclic group, provided that at least one R$^{44}$ is not hydrogen, and wherein said substituents are as defined herein.

"Halo" or "halogen" refers to fluoro, chloro, bromo and iodo and preferably is fluoro or chloro.

"Haloalkyl" refers to alkyl groups substituted with 1 to 5, 1 to 3, or 1 to 2 halo groups, wherein alkyl and halo are as defined herein.

"Haloalkoxy" refers to alkoxy groups substituted with 1 to 5, 1 to 3, or 1 to 2 halo groups, wherein alkoxy and halo are as defined herein.

"Haloalkylthio" refers to alkylthio groups substituted with 1 to 5, 1 to 3, or 1 to 2 halo groups, wherein alkylthio and halo are as defined herein.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridyl, pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, and/or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems. In fused ring systems, one or more the rings can be cycloalkyl, aryl, or heteroaryl provided that the point of attachment is through the non-aromatic heterocyclic ring. In one embodiment, the nitrogen and/or sulfur atom(s) of the heterocyclic group are optionally oxidized to provide for the N-oxide, sulfinyl, and/or sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group —NO$_2$.

"Oxo" refers to the atom (=O) or (—O—).

"Spiro ring systems" refers to bicyclic ring systems that have a single ring carbon atom common to both rings.

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-cycloalkenyl, —SO$_2$-substituted cylcoalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Substituted sulfonyl includes groups such as methyl-SO$_2$—, phenyl-SO$_2$—, and 4-methylphenyl-SO$_2$—. The term "alkylsulfonyl" refers to —SO$_2$-alkyl. The term "haloalkylsulfonyl" refers to —SO$_2$-haloalkyl where haloalkyl is defined herein. The term "(substituted sulfonyl)amino" refers to —NH(substituted sulfonyl), and the term "(substituted sulfonyl)aminocarbonyl" refers to —C(O)NH(substituted sulfonyl), wherein substituted sulfonyl is as defined herein.

"Sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cycloalkyl, —OSO$_2$-cycloalkenyl, —OSO$_2$-substituted cylcoalkenyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thiol" refers to the group —SH.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein.

"Compound" or "compounds" as used herein is meant to include the stereoisomers and tautomers of the indicated formulas.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

As used herein, the term "phosphate ester" refers to any one of the mono-, di- or triphosphate esters of noribogaine, wherein the mono-, di- or triphosphate ester moiety is bonded to the 12-hydroxy group and/or the indole nitrogen of noribogaine.

As used herein, the term "phosphate ester" refers to any one of the mono-, di- or triphosphate esters of noribogaine, wherein the mono-, di- or triphosphate ester moiety is bonded to the 12-hydroxy group and/or the indole nitrogen of noribogaine.

As used herein, the term "monophosphate" refers to the group —P(O)(OH)$_2$.

As used herein, the term "diphosphate" refers to the group —P(O)(OH)—OP(O)(OH)$_2$.

As used herein, the term "triphosphate" refers to the group —P(O)(OH)—(OP(O)(OH))$_2$OH.

As used herein, the term "ester" as it refers to esters of the mono-, di- or triphosphate group means esters of the monophosphate can be represented by the formula —P(O)(OR$^{45}$)$_2$, where each R$^{45}$ is independently hydrogen, C$_1$-C$_{12}$ alkyl, C$_3$-C$_{10}$ cycloalkyl, C$_6$-C$_{14}$ aryl, heteroaryl of 1 to 10 carbon atoms and 1 to 4 optionally oxidized heteroatoms selected from the group consisting of oxygen, nitrogen, and sulfur and the like, provided that at least one R$^{45}$ is not hydrogen. Likewise, exemplary esters of the di- or triphosphate can be represented by the formulas —P(O)(OR$^{45}$)—OP(O)(OR$^{45}$)$_2$ and —P(O)(OR$^{45}$)—(OP(O)(OR$^{45}$))$_2$OR$^{45}$, where R$^{45}$ is as defined above.

As used herein, the term "hydrolyzable group" refers to a group that can be hydrolyzed to release the free hydroxy group under hydrolysis conditions. Examples of hydrolysable group include, but are not limited to those defined for R above. Preferred hydrolysable groups include carboxyl esters, phosphates and phosphate esters. The hydrolysis may be done by chemical reactions conditions such as base hydrolysis or acid hydrolysis or may be done in vivo by biological processes, such as those catalyzed by a phosphate hydrolysis enzyme. Nonlimiting examples of hydrolysable group include groups linked with an ester-based linker (—C(O)O— or —OC(O)—), an amide-based linker (—C(O)NR$^{46}$— or —NR$^{46}$C(O)—), or a phosphate-linker (—P(O)(OR$^{46}$)—O—, —O—P(S)(OR$^{46}$)—O—, —O—P(S)(SR$^{46}$)—O—, —S—P(O)(OR$^{46}$)—O—, —O—P(O)(OR$^{46}$)—S—, —S—P(O)(OR$^{46}$)—S—, —O—P(S)(OR$^{46}$)—S—,—S—P(S)(OR$^{46}$)—O—,—O—P(O)(R$^{46}$)—O—, —O—P(S)(R$^{46}$)—O—, —S—P(O)(R$^{46}$)—O—, —S—P(S)(R$^{46}$)—O—, —S—P(O)(R$^{46}$)—S—, or —O—P(S)(R$^{46}$)—S—) where R$^{46}$ can be hydrogen or alkyl.

Substituted groups of this invention, as set forth above, do not include polymers obtained by an infinite chain of substituted groups. At most, any substituted group can be substituted up to five times.

The term "iboga alkaloid" as used herein refers to ibogaine or noribogaine. Iboga alkaloid also refers to a derivative of noribogaine or ibogaine, as well as pharmaceutically acceptable salts and pharmaceutically acceptable solvates thereof.

"Ibogaine" refers to the compound:

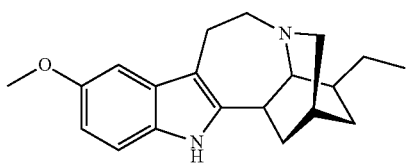

as well as ibogaine derivatives, pharmaceutically acceptable salts, and pharmaceutically acceptable solvates thereof. It should be understood that where "ibogaine" is mentioned herein, one more polymorphs of ibogaine can be utilized and are contemplated. Ibogaine is isolated from *Tabernanth iboga*, a shrub of West Africa. Ibogaine can also be synthesized using known methods. See, e.g., Büchi, et al. (1966), J. Am. Chem Society, 88(13), 3099-3109. Non-limiting examples of ibogaine derivatives encompassed by this invention are given in more detail in the "Compositions of the Invention" section below.

"Noribogaine" refers to the compound:

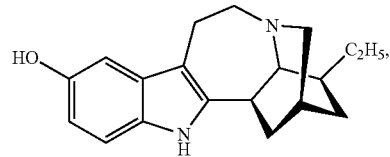

as well as noribogaine derivatives, pharmaceutically acceptable salts, and pharmaceutically acceptable solvates thereof. It should be understood that where "noribogaine" is mentioned herein, one more polymorphs of noribogaine can be utilized and are contemplated. In some embodiments, noribogaine is noribogaine glucuronide. Noribogaine can be prepared by demethylation of naturally occurring ibogaine. Demethylation may be accomplished by conventional techniques, such as by reaction with boron tribromide/methylene chloride at room temperature followed by conventional purification. See, for example, Huffman, et al., J. Org. Chem. 50:1460 (1985), which is incorporated herein by reference in its entirety. Noribogaine can be synthesized as described, for example in U.S. Patent Pub. Nos. 2013/0165647, 2013/0303756, and 2012/0253037, PCT Patent Publication No. WO 2013/040471 (includes description of making noribogaine polymorphs), and U.S. patent application Ser. No. 13/593,454, each of which is incorporated herein by reference in its entirety.

"Noribogaine derivatives" refer to esters or O-carbamates of noribogaine, or pharmaceutically acceptable salts and/or solvates of each thereof. Also encompassed within this invention are derivatives of noribogaine that act as prodrug forms of noribogaine. A prodrug is a pharmacological substance administered in an inactive (or significantly less active) form. Once administered, the prodrug is metabolized in vivo into an active metabolite. Noribogaine derivatives include, without limitation, those compounds set forth in U.S. Pat. Nos. 6,348,456 and 8,362,007; as well as in U.S. patent application Ser. No. 13/165,626; and US Patent Application Publication Nos. US2013/0131046; US2013/0165647; US2013/0165425; and US2013/0165414; all of which are incorporated herein by reference. Non-limiting examples of noribogaine derivatives encompassed by this invention are given in more detail in the "Compositions of the Invention" section below.

This invention is not limited to any particular chemical form of iboga alkaloid, and the drug may be given to patients either as a free base, solvate, or as a pharmaceutically acceptable acid addition salt. In the latter case, the hydrochloride salt is generally preferred, but other salts derived from organic or inorganic acids may also be used. Examples of such acids include, without limitation, those described below as "pharmaceutically acceptable salts" and the like.

"Pharmaceutically acceptable composition" refers to a composition that is suitable for administration to a human. Such compositions include various excipients, diluents, carriers, and such other inactive agents well known to the skilled artisan.

"Pharmaceutically acceptable salt" refers to pharmaceutically acceptable salts, including pharmaceutically acceptable partial salts, of a compound, which salts are derived from a variety of organic and inorganic counter ions well known in the art and include, by way of example only, hydrochloric acid, hydrobromic acid, phosphoric acid, sulfuric acid, methane sulfonic acid, phosphorous acid, nitric acid, perchloric acid, acetic acid, tartaric acid, lactic acid, succinic acid, citric acid, malic acid, maleic acid, aconitic acid, salicylic acid, thalic acid, embonic acid, enanthic acid, oxalic acid and the like, and when the molecule contains an acidic functionality, include, by way of example only, sodium, potassium, calcium, magnesium, ammonium, tetraalkylammonium, and the like.

"Therapeutically effective amount" or "effective amount" refers to an amount of a drug or an agent that, when administered to a patient suffering from a condition, will have the intended therapeutic effect, e.g., alleviation, amelioration, palliation, elimination, or prevention of one or more manifestations (e.g., symptoms) of the condition in the patient. The therapeutically effective amount will vary depending upon the patient and the condition being treated, the weight and age of the subject, the severity of the condition, the salt, solvate, or derivative of the active drug portion chosen, the particular composition or excipient chosen, the dosing regimen to be followed, timing of administration, the manner of administration and the like, all of which can be determined readily by one of ordinary skill in the art. The full therapeutic effect does not necessarily occur by administration of one dose, and may occur only after administration of a series of doses. Thus, a therapeutically effective amount may be administered in one or more administrations. For example, and without limitation, a therapeutically effective amount of iboga alkaloid, in the context of potentiating the effect of an opioid analgesic, refers to an amount of iboga alkaloid that increases the analgesic effect of the opioid analgesic in a patient. This amount is also referred to as the "potentiating amount" of iboga alkaloid. In particular the potentiating amount of the iboga alkaloid or pharmaceutically acceptable salt or solvate thereof is such that the QT interval experienced by the patient is less than about 60 ms, less than about 50 ms, preferably less than 30 ms, more preferably less than 20 ms.

A "therapeutic level" of a drug is an amount of iboga alkaloid or pharmaceutical salt and/or solvate thereof that is sufficient to potentiate the effect of an opioid analgesic, but not high enough to pose any significant risk to the patient. Therapeutic levels of drugs can be determined by tests that measure the actual concentration of the compound in the blood of the patient. This concentration is referred to as the "serum concentration." Where the serum concentration of iboga alkaloid is mentioned, it is to be understood that the term "iboga alkaloid" encompasses any form of iboga alkaloid, including derivatives thereof.

The term "potentiation" as used herein refers to an increase in the action of a drug by the addition of another drug that does not necessarily possess similar properties.

The term "dose" refers to a range of iboga alkaloid or pharmaceutical salt or solvate thereof that provides a therapeutic serum level of noribogaine when given to a patient in need thereof. The dose is recited in a range, for example from about 0.001 mg to about 50 mg per day, and can be expressed either as milligrams (mg) or as mg/kg body weight. The attending clinician will select an appropriate dose from the range based on the patient's weight, age, opioid analgesic, health, and other relevant factors, all of which are well within the skill of the art.

The term "unit dose" refers to a dose of drug that is given to the patient to provide therapeutic results, independent of the weight of the patient. In such an instance, the unit dose is sold in a standard form (e.g., 10 mg tablet). The unit dose may be administered as a single dose or a series of subdoses. In some embodiments, the unit dose provides a standardized level of drug to the patient, independent of weight of patient. Many medications are sold based on a dose that is therapeutic to all patients based on a therapeutic window. In such cases, it is not necessary to titrate the dosage amount based on the weight of the patient.

"Treatment," "treating," and "treat" are defined as acting upon a disease, disorder, or condition with an agent to reduce or ameliorate harmful or any other undesired effects of the disease, disorder, or condition and/or its symptoms. "Treatment," as used herein, covers the treatment of a human patient, and includes: (a) reducing the risk of occurrence of the condition in a patient determined to be predisposed to the condition but not yet diagnosed as having the condition, (b) impeding the development of the condition, and/or (c) relieving the condition, i.e., causing regression of the condition and/or relieving one or more symptoms of the condition. "Treating" or "treatment of" a condition or patient refers to taking steps to obtain beneficial or desired results, including clinical results such as the reduction of symptoms. For purposes of this invention, beneficial or desired clinical results include, but are not limited to increasing the effect of a given dose of an opioid analgesic compound; reducing, attenuating, relieving, or reversing tolerance to the opioid analgesic; reducing the risk of or preventing dependency and/or addiction to the opioid analgesic.

"Nociceptive pain" refers to pain that is sensed by nociceptors, which are the nerves that sense and respond to parts of the body suffering from a damage. The nociceptors can signal tissue irritation, impending injury, or actual injury. When activated, they transmit pain signals (via the peripheral nerves as well as the spinal cord) to the brain. Nociceptive pain is typically well localized, constant, and often has an aching or throbbing quality. A subtype of nociceptive pain includes visceral pain and involves the internal organs. Visceral pain tends to be episodic and poorly localized. Nociceptive pain may be time limited; when the tissue damage heals, the pain typically resolves. However, nociceptive pain related to arthritis or cancer may not be time limited. Nociceptive pain tends to respond to treatment with opiate analgesics, such as, for example, buprenorphin, codeine, hydrocodone, oxycodone, morphine, and the like. Examples of nociceptive pain include, without limitation, pains from sprains, bone fractures, burns, bumps, bruises, cuts, inflammatory pain from an infection or arthritic disorder, pains from obstructions, cancer pain, and myofascial pain related to abnormal muscle stresses.

"Neuropathic pain" refers to chronic pain, often due to tissue injury. Neuropathic pain is generally caused by injury or damage to nerve fibers. It may include burning or coldness, "pins and needles" sensations, numbness and/or itching. It may be continuous and/or episodic. Neuropathic pain is difficult to treat, but can be treated with opioids, including, without limitation, methadone, tramadol, tapentadol, oxycodone, methadone, morphine, levorphanol, and the like. Causes of neuropathic pain include, without limitation, alcoholism; amputation; back, leg, and hip problems; chemotherapy; diabetes; facial nerve problems; HIV/AIDS; multiple sclerosis; shingles; spine surgery; trigeminal neuralgia; fibromyalgia; and the like. In some cases, the cause of neuropathic pain may be unclear or unknown.

"Addictive" refers to a compound that, when administered to a mammal over a period of time, creates dependency and/or addiction in the mammal to that compound. The dependence can be physiological and/or psychological. A therapeutic effect of an addictive compound on a mammal may decrease with prolonged administration of the addictive compound, which is a non-limiting example of a physiological dependence. When administered to a mammal, an addictive compound may also create a craving in the mammal for more of it, which is a non-limiting example of a psychological dependence. Examples of addictive compounds include, without limitation, addictive opioids, and the like. In contrast, ibogaine, noribogaine, and derivatives of each are non-addictive alkaloids.

The term "tolerance" as used herein refers to the psychological and/or physiologic process wherein the patient adjusts to the frequent presence of a substance such that a higher dose of the substance is required to achieve the same effect. Tolerance may develop at different times for different effects of the same drug (e.g., analgesic effect versus side effects). The mechanisms of tolerance are not entirely understood, but they may include receptor down-regulation or desensitization, inhibitory pathway up-regulation, increased metabolism, and/or changes in receptor processing (e.g., phosphorylation).

"Opioid" refers to a natural product or derivative thereof containing a basic nitrogen atom, typically as part of a cyclic ring structure and less commonly as an acyclic moiety, and synthetic derivatives thereof. Opioids include compounds extracted from poppy pods and their semi-synthetic counterparts which bind to the opiate receptors. Non-limiting examples of opioids include, without limitation, buprenorphine, codeine, heroine, hydrocodone, oxycodone, morphine, hydromorphone, thebaine, and their derivatives, which will be well known to the skilled artisan.

"Analgesic" and "analgesic agent" refer to a compound that is capable of inhibiting and/or reducing pain in mammals. Pain may be inhibited and/or reduced in the mammal by the binding of the opioid analgesic agent to the mu receptor. When analgesia is effected through the mu receptor, the analgesic agent is referred to as a mu receptor agonist. Certain analgesic agents are capable of inhibiting nociceptive and/or neuropathic pain including, by way of non-limiting example, morphine, codeine, hydromorphone, oxycodone, hydrocodone, buprenorphin, and the like.

As used herein, the term "patient" refers to a human.

As used herein, the term "QT interval" refers to the measure of the time between the start of the Q wave and the end of the T wave in the electrical cycle of the heart. Prolongation of the QT interval refers to an increase in the QT interval, i.e., increase from a baseline QT interval.

A "pharmaceutically acceptable solvate" or "hydrate" of a compound of the invention means a solvate or hydrate complex that is pharmaceutically acceptable and that possesses the desired pharmacological activity of the parent compound, and includes, but is not limited to, complexes of a compound of the invention with one or more solvent or water molecules, or 1 to about 100, or 1 to about 10, or one to about 2, 3 or 4, solvent or water molecules.

Herein the term solvate refers to a solid form of a compound that crystallizes with one or more molecules of solvent trapped inside. A few examples of solvents that can be used to create solvates, such as pharmaceutically acceptable solvates, include, but are not limited to, water, methanol, ethanol, isopropanol, butanol, C1-C6 alcohols in general (and optionally substituted), tetrahydrofuran, acetone, ethylene glycol, propylene glycol, acetic acid, formic acid, water, and solvent mixtures thereof. Other such biocompatible solvents which may aid in making a pharmaceutically acceptable solvate are well known in the art and applicable to the present invention. Additionally, various organic and inorganic acids and bases can be added or even used alone as the solvent to create a desired solvate. Such acids and bases are known in the art. When the solvent is water, the solvate can be referred to as a hydrate. Further, by being left in the atmosphere or recrystallized, the compounds of the present invention may absorb moisture, may include one or more molecules of water in the formed crystal, and thus become a hydrate. Even when such hydrates are formed, they are included in the term "solvate". Solvate also is meant to include such compositions where another compound or complex co-crystallizes with the compound of interest.

As used herein the term "abuse liability" refers to the properties of a drug (e.g., an opiate) that would lead to abuse and dependence in humans. The drug may be available as a prescription medication and/or through illicit routes.

II. Compositions of the Invention

As will be apparent to the skilled artisan upon reading this disclosure, this invention provides compositions for potentiating the effect of an opioid analgesic in a patient undergoing or planning to undergo opioid analgesic treatment for pain, comprising an effective amount of an iboga alkaloid, derivative, prodrug, pharmaceutically acceptable salt and/or solvate of each thereof and wherein the iboga alkaloid is dosed in an amount to both potentiate the opioid while maintaining an acceptable QT interval prolongation. In a preferred embodiment, the iboga alkaloid is noribogaine or a salt or solvate thereof.

In some embodiments, the composition is formulated for oral, transdermal, internal, pulmonary, rectal, nasal, vaginal, lingual, intravenous, intraarterial, intramuscular, intraperitoneal, intracutaneous or subcutaneous delivery.

In one embodiment, the therapeutically effective amount of the compound is from about 0.001 mg to about 50 mg per day. In a preferred embodiment, the therapeutically effective amount of the compound is from about 0.001 mg to about 30 mg per day. In another embodiment, the therapeutically effective amount of the compound is from about 0.001 mg to about 20 mg per day. In another embodiment, the therapeutically effective amount of the compound is from about 0.001 mg to about 10 mg per day. In another embodiment, the therapeutically effective amount of the compound is from about 0.001 mg to about 5 mg per day. In another embodiment, the therapeutically effective amount of the compound is from about 0.001 mg to about 1 mg per day. In another embodiment, the therapeutically effective amount of the compound is from about 0.001 mg to about 0.1 mg per day. In another embodiment, the therapeutically effective amount of the compound is from about 0.001 mg to about 0.01 mg per day. The ranges include both extremes as well as any subranges there between.

In another embodiment, the therapeutically effective amount of the compound is from about 0.01 mg to about 50 mg per day. In another embodiment, the therapeutically effective amount of the compound is from about 0.01 mg to about 30 mg per day. In another embodiment, the therapeutically effective amount of the compound is from about 0.01 mg to about 20 mg per day. In another embodiment, the therapeutically effective amount of the compound is from about 0.01 mg to about 10 mg per day. In another embodiment, the therapeutically effective amount of the compound is from about 0.01 mg to about 5 mg per day. In another embodiment, the therapeutically effective amount of the compound is from about 0.01 mg to about 1 mg per day. In another embodiment, the therapeutically effective amount of the compound is from about 0.01 mg to about 0.1 mg per day. The ranges include both extremes as well as any subranges there between. The ranges include both extremes as well as any subranges there between.

In another embodiment, the therapeutically effective amount of the compound is from about 0.1 mg to about 50 mg per day. In another embodiment, the therapeutically effective amount of the compound is from about 0.1 mg to about 30 mg per day. In another embodiment, the therapeutically effective amount of the compound is from about 0.1 mg to about 20 mg per day. In another embodiment, the therapeutically effective amount of the compound is from about 0.1 mg to about 10 mg per day. In another embodiment, the therapeutically effective amount of the compound is from about 0.1 mg to about 5 mg per day. In another embodiment, the therapeutically effective amount of the compound is from about 0.1 mg to about 1 mg per day. The ranges include both extremes as well as any subranges there between. The ranges include both extremes as well as any subranges there between.

In another embodiment, the therapeutically effective amount of the compound is from about 1 mg to about 50 mg per day. In another embodiment, the therapeutically effective amount of the compound is from about 1 mg to about 30 mg per day. In another embodiment, the therapeutically effective amount of the compound is from about 1 mg to about 20 mg per day. In another embodiment, the therapeutically effective amount of the compound is from about 1 mg to about 10 mg per day. In another embodiment, the therapeutically effective amount of the compound is from about 1 mg to about 5 mg per day. The ranges include both extremes as well as any subranges there between. The ranges include both extremes as well as any subranges there between.

In one embodiment, the therapeutically effective amount of the compound is from about 5 mg to about 50 mg per day. In a preferred embodiment, the therapeutically effective amount of the compound is from about 5 mg to about 30 mg per day. In another embodiment, the therapeutically effective amount of the compound is from about 5 mg to about 20 mg per day. In another embodiment, the therapeutically effective amount of the compound is from about 10 mg to about 50 mg per day. In another embodiment, the therapeutically effective amount of the compound is from about 10 mg to about 30 mg per day. In another embodiment, the therapeutically effective amount of the compound is from about 10 mg to about 20 mg per day. The ranges include both extremes as well as any subranges there between.

In one embodiment, the therapeutically effective amount of the compound is about 0.001 mg per day. In one embodiment, the therapeutically effective amount of the compound is about 0.01 mg per day. In one embodiment, the therapeutically effective amount of the compound is about 0.1 mg per day. In one embodiment, the therapeutically effective amount of the compound is about 1 mg per day. In one embodiment, the therapeutically effective amount of the compound is about 5 mg per day. In one embodiment, the therapeutically effective amount of the compound is about 10 mg per day. In one embodiment, the therapeutically effective amount of the compound is about 15 mg per day. In one embodiment, the therapeutically effective amount of the compound is about 20 mg per day. In one embodiment, the therapeutically effective amount of the compound is about 25 mg per day. In one embodiment, the therapeutically effective amount of the compound is about 30 mg per day. In one embodiment, the therapeutically effective amount of the compound is about 35 mg per day. In one embodiment, the therapeutically effective amount of the compound is about 40 mg per day. In one embodiment, the therapeutically effective amount of the compound is about 45 mg per day. In one embodiment, the therapeutically effective amount of the compound is about 50 mg per day. In one embodiment, the therapeutically effective amount of the compound is about 60 mg per day. In one embodiment, the therapeutically effective amount of the compound is about 70 mg per day. In one embodiment, the therapeutically effective amount of the compound is about 80 mg per day.

In one embodiment, the iboga alkaloid is ibogaine, noribogaine, an ibogaine derivative, noribogaine derivative, or prodrug, salt or solvate thereof.

In one embodiment, the noribogaine derivative is represented by Formula I:

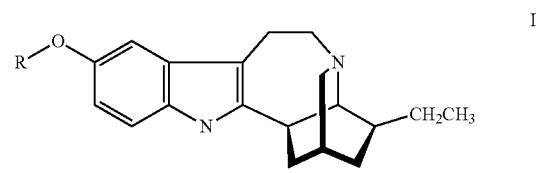

I or a pharmaceutically acceptable salt and/or solvate thereof, wherein R is hydrogen or a hydrolyzable group such as hydrolyzable esters of from about 1 to 12 carbons.

Generally, in the above formula, R is hydrogen or a group of the formula:

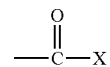

wherein X is a $C_1$-$C_{12}$ group, which is unsubstituted or substituted. For example, X may be a linear alkyl group such as methyl, ethyl, n-propyl, n-butyl, n-pentyl, n-hexyl, n-heptyl, n-octyl, n-nonyl, n-decyl, n-undecyl or n-dodecyl, or a branched alkyl group, such as i-propyl or sec-butyl. Also, X may be a phenyl group or benzyl group, either of which may be substituted with lower alkyl groups or lower alkoxy groups. Generally, the lower alkyl and/or alkoxy groups have from 1 to about 6 carbons. For example, the group R may be acetyl, propionyl or benzoyl. However, these groups are only exemplary.

Generally, for all groups X, they may either be unsubstituted or substituted with lower alkyl or lower alkoxy groups. For example, substituted X may be o-, m- or p-methyl or methoxy benzyl groups.

$C_1$-$C_{12}$ groups include $C_1$-$C_{12}$ alkyl, $C_3$-$C_{12}$ cycloalkyl, $C_6$-$C_{12}$ aryl, $C_7$-$C_{12}$ arylalkyl, wherein $C_x$ indicates that the group contains x carbon atoms. Lower alkyl refers to $C_1$-$C_4$ alkyl and lower alkoxy refers to $C_1$-$C_4$ alkoxy.

In one embodiment, the noribogaine derivative is represented by Formula II:

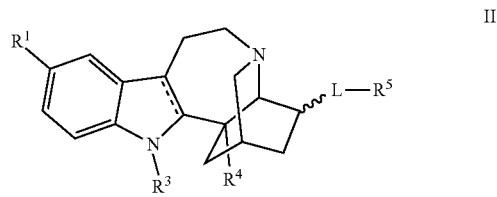

II or a pharmaceutically acceptable salt and/or solvate thereof, wherein

------ is a single or double bond;

$R^1$ is halo, $OR^2$, or $C_1$-$C_{12}$ alkyl optionally substituted with 1 to 5 $R^{10}$;

$R^2$ is hydrogen or a hydrolysable group selected from the group consisting of —C(O)$R^x$, —C(O)O$R^x$ and —C(O)N($R^y$)$_2$ where each $R^x$ is selected from the group consisting of $C_1$-$C_6$ alkyl optionally substituted with 1 to 5 $R^{10}$, and
  each $R^y$ is independently selected from the group consisting of hydrogen, $C_1$-$C_6$ alkyl optionally substituted with 1 to 5 $R^{10}$, $C_6$-$C_{14}$ aryl optionally substituted with 1 to 5 $R^{10}$, $C_3$-$C_{10}$ cycloalkyl optionally substituted with 1 to 5 $R^{10}$, $C_1$-$C_{10}$ heteroaryl having 1 to 4 heteroatoms and which is optionally substituted with 1 to 5 $R^{10}$, $C_1$-$C_{10}$ heterocyclic having 1 to 4 heteroatoms and which is optionally substituted with 1 to 5 $R^{10}$, and where each $R^y$, together with the nitrogen atom bound thereto form a $C_1$-$C_6$ heterocyclic having 1 to 4 heteroatoms and which is optionally substituted with 1 to 5 $R^{10}$ or a $C_1$-$C_6$ heteroaryl having 1 to 4 heteroatoms and which is optionally substituted with 1 to 5 $R^{10}$;

$R^3$ is selected from the group consisting of hydrogen, $C_1$-$C_{12}$ alkyl optionally substituted with 1 to 5 $R^{10}$, aryl optionally substituted with 1 to 5 $R^{10}$, —C(O)$R^6$, —C(O)N$R^6R^6$ and —C(O)O$R^6$;

$R^4$ is selected from the group consisting of hydrogen, —(CH$_2$)$_m$O$R^8$, —C$R^7$(OH)$R^8$, —(CH$_2$)$_m$CN, —(CH$_2$)$_m$CO$R^8$, —(CH$_2$)$_m$CO$_2R^8$, —(CH$_2$)$_m$C(O)N$R^7R^8$, —(CH$_2$)$_m$C(O)N$R^7$N$R^8R^8$, —(CH$_2$)$_m$C(O)N$R^7$N$R^8$C(O)$R^9$, and —(CH$_2$)$_m$N$R^7R^8$;

m is 0, 1, or 2;

L is a bond or $C_1$-$C_{12}$ alkylene;

$R^5$ is selected from the group consisting of hydrogen, $C_1$-$C_{12}$ alkyl substituted with 1 to 5 $R^{10}$, $C_1$-$C_{12}$ alkenyl substituted with 1 to 5 $R^{10}$, —$X^1$—$R^7$, —($X^1$—Y)$_n X^1$—$R^7$, —SO$_2$N$R^7R^8$, —O—C(O)$R^9$, —C(O)O$R^8$, —C(O)N$R^7R^8$, —N$R^7R^8$, —NHC(O)$R^9$, and —N$R^7$C(O)$R^9$;

each $R^6$ is independently selected from the group consisting of hydrogen, $C_1$-$C_{12}$ alkyl, $C_2$-$C_{12}$ alkenyl, $C_2$-$C_{12}$ alkynyl, $C_6$-$C_{10}$ aryl, $C_1$-$C_6$ heteroaryl having 1 to 4 heteroatoms, and $C_1$-$C_6$ heterocycle having 1 to 4 heteroatoms, and wherein the alkyl, alkenyl, alkynyl, aryl, heteroaryl, and heterocycle are optionally substituted with 1 to 5 $R^{10}$;

$X^1$ is selected from the group consisting of O and S;

Y is $C_1$-$C_4$ alkylene or $C_6$-$C_{10}$ arylene, or a combination thereof;

n is 1, 2, or 3;

$R^7$ and $R^8$ are each independently selected from the group consisting of hydrogen, $C_1$-$C_{12}$ alkyl optionally substituted with 1 to 5 $R^{10}$, $C_1$-$C_6$ heterocycle having 1 to 4 heteroatoms and which is optionally substituted with 1 to 5 $R^{10}$, $C_3$-$C_{10}$ cycloalkyl optionally substituted with 1 to 5 $R^{10}$, $C_6$-$C_{10}$ aryl optionally substituted with 1 to 5 $R^{10}$ and $C_1$-$C_6$ heteroaryl having 1 to 4 heteroatoms optionally substituted with 1 to 5 $R^{10}$;

$R^9$ is selected from the group consisting of $C_1$-$C_{12}$ alkyl optionally substituted with 1 to 5 $R^{10}$, $C_1$-$C_6$ heterocycle having 1 to 4 heteroatoms optionally substituted with 1 to 5 $R^{10}$, $C_3$-$C_{10}$ cycloalkyl optionally substituted with 1 to 5 $R^{10}$, $C_6$-$C_{10}$ aryl optionally substituted with 1 to 5 $R^{10}$ and $C_1$-$C_6$ heteroaryl having 1 to 4 heteroatoms optionally substituted with 1 to 5 $R^{10}$;

$R^{10}$ is selected from the group consisting of $C_1$-$C_4$ alkyl, phenyl, halo, —O$R^{11}$, —CN, —CO$R^{11}$, —CO$_2R^{11}$, —C(O)NH$R^{11}$, —N$R^{11}R^{11}$, C(O)N$^{11}R^{11}$, —C(O)NHN HR$^{11}$, —C(O)N$R^{11}$NH$R^{11}$, —C(O)N$R^{11}$N$R^{11}R^{11}$, —C(O)NHN$R^{11}C(O)R^{11}$, —C(O)NHNHC(O)$R^{11}$, —SO$_2$N$R^{11}R^{11}$, —C(O)N$R^{11}$N$R^{11}$C(O)$R^{11}$, and —C(O)N$R^{11}$NHC(O)$R^{11}$; and $R^{11}$ is independently hydrogen or $C_1$-$C_{12}$ alkyl;

provided that:
  when L is a bond, then $R^5$ is not hydrogen;
  when ------ is a double bond, $R^1$ is an ester hydrolyzable group, $R^3$ and $R^4$ are both hydrogen, then -L-$R^5$ is not ethyl;
  when ------ is a double bond, $R^1$ is —OH, halo or $C_1$-$C_{12}$ alkyl optionally substituted with 1 to 5 $R^{10}$, then $R^4$ is hydrogen; and
  when ------ is a double bond, $R^1$ is O$R^2$, $R^4$ is hydrogen, -L-$R^5$ is ethyl, then $R^2$ is not a hydrolyzable group selected from the group consisting of an ester, amide, carbonate and carbamate.

In one embodiment, the noribogaine derivative is represented by Formula III:

III or a pharmaceutically acceptable salt and/or solvate thereof, wherein
  ------ is a single or double bond;
  $R^{12}$ is halo, —OH, —SH, —NH$_2$, —S(O)$_2$N($R^{17}$)$_2$, —$R^z$-$L^1$-$R^{18}$, —$R^z$-$L^1$-$R^{19}$, —$R^z$-$L^1$-$R^{20}$ or —$R^z$-$L^1$-CH$R^{18}R^{19}$, where $R^z$ is O, S or N$R^{17}$;
  $L^1$ is alkylene, arylene, —C(O)-alkylene, —C(O)-arylene, —C(O)O-arylene, —C(O)O-alkylene, —C(O)N$R^{20}$-alkylene, —C(O)N$R^{20}$-arylene, —C(N$R^{20}$)N$R^{20}$-alkylene or —C(N$R^{20}$)N$R^{20}$-arylene, wherein $L^1$ is configured such that —O-$L^1$-$R^{18}$ is —OC(O)-alkylene-$R^{18}$, —OC(O)O-arylene-$R^{18}$, —OC(O)O-alkylene-$R^{18}$, —OC(O)-arylene-$R^{18}$, —OC(O)N$R^{20}$-alkylene-$R^{18}$, —OC(O)N$R^{20}$-arylene-$R^{18}$, —OC(N$R^{20}$)N$R^{20}$-alkylene-$R^{18}$ or —OC(N$R^{20}$)N$R^{20}$-arylene-$R^{18}$, and wherein the alkylene and arylene are optionally substituted with 1 to 2 $R^{16}$;
  $R^{13}$ is hydrogen, —S(O)$_2$O$R^{20}$, —S(O)$_2R^{20}$, —C(O)$R^{15}$, —C(O)N$R^{15}R^{15}$, —C(O)O$R^{15}$, $C_1$-$C_{12}$ alkyl optionally substituted with 1 to 5 $R^{16}$, $C_1$-$C_{12}$ alkenyl optionally substituted with 1 to 5 $R^{16}$, or aryl optionally substituted with 1 to 5 $R^{16}$;
  $R^{14}$ is hydrogen, halo, —O$R^{17}$, —CN, $C_1$-$C_{12}$ alkyl, $C_1$-$C_{12}$ alkoxy, aryl or aryloxy, where the alkyl, alkoxy, aryl, and aryloxy are optionally substituted with 1 to 5 $R^{16}$;
  each $R^{15}$ is independently selected from the group consisting of hydrogen, $C_1$-$C_{12}$ alkyl, $C_2$-$C_{12}$ alkenyl, $C_2$-$C_{12}$ alkynyl, aryl, heteroaryl, and heterocycle, and wherein the alkyl, alkenyl, alkynyl, aryl, heteroaryl, and heterocycle are optionally substituted with 1 to 5 $R^{16}$;
  $R^{16}$ is selected from the group consisting of phenyl, halo, —O$R^{17}$, —CN, —CO$R^{17}$, —CO$_2R^{17}$, —N$R^{17}R^{17}$, —N$R^{17}$C(O)$R^{17}$, —N$R^{17}$SO$_2R^{17}$, —C(O)N$R^{17}R^{17}$, —C(O)N$R^{17}$N$R^{17}R^{17}$, —SO$_2$N$R^{17}R^{17}$ and —C(O)N$R^{17}$N$R^{17}$C(O)$R^{17}$;
  each $R^{17}$ is independently hydrogen or $C_1$-$C_{12}$ alkyl optionally substituted with from 1 to 3 halo;

$R^{18}$ is hydrogen, —C(O)$R^{20}$, —C(O)O$R^{20}$, —C(O)N($R^{20}$)$_2$ or —N($R^{20}$)C(O)$R^{20}$;

$R^{19}$ is hydrogen, —N($R^{20}$)$_2$, —C(O)N($R^{20}$)$_2$, —C(N$R^{20}$)N($R^{20}$)$_2$, —C(NSO$_2$$R^{20}$)N($R^{20}$)$_2$, —N$R^{20}$C(O)N($R^{20}$)$_2$, —N$R^{20}$C(S)N($R^{20}$)$_2$, —N$R^{20}$C(N$R^{20}$)N($R^{20}$)$_2$, —N$R^{20}$C(NSO$_2$$R^{20}$)N($R^{20}$)$_2$ or tetrazole; and each $R^{20}$ is independently selected from the group consisting of hydrogen, $C_1$-$C_{12}$ alkyl and aryl;

provided that:

when ------ is a double bond and $R^{13}$ and $R^{14}$ are hydrogen, then $R^{12}$ is not hydroxy;

when ------ is a double bond, $R^{14}$ is hydrogen, $R^{12}$ is —O-$L^1$-$R^{18}$, —O-$L^1$-$R^{19}$, —O-$L^1$-$R^{20}$, and $L^1$ is alkylene, then —O-$L^1$-$R^{18}$, —O-$L^1$-$R^{19}$, —O-$L^1$-$R^{20}$ are not methoxy;

when ------ is a double bond, $R^{14}$ is hydrogen, $R^z$ is O, $L^1$ is —C(O)-alkylene, —C(O)-arylene, —C(O)O-arylene, —C(O)O-alkylene, —C(O)N$R^{20}$-alkylene, or —C(O)N$R^{20}$-arylene, then none of $R^{18}$, $R^{19}$ or $R^{20}$ are hydrogen.

In one embodiment, the noribogaine derivative is represented by Formula IV:

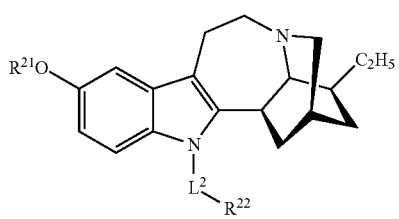

IV or a pharmaceutically acceptable salt and/or solvate thereof, wherein $R^{21}$ is selected from the group consisting of hydrogen, a hydrolysable group selected from the group consisting of —C(O)$R^{23}$, —C(O)N$R^{24}$$R^{25}$ and —C(O)O$R^{26}$, where $R^{23}$ is selected from the group consisting of hydrogen, alkyl, substituted alkyl, alkenyl, substituted alkenyl, alkynyl and substituted alkynyl, $R^{24}$ and $R^{25}$ are independently selected from the group consisting of hydrogen, alkyl, substituted alkyl, alkenyl, substituted alkenyl, alkynyl, substituted alkynyl, aryl, substituted aryl, heteroaryl, substituted heteroaryl, heterocyclic and substituted heterocyclic, $R^{26}$ is selected from the group consisting of alkyl, substituted alkyl, alkenyl, substituted alkenyl, alkynyl, substituted alkynyl, aryl, substituted aryl, heteroaryl, substituted heteroaryl, heterocyclic and substituted heterocyclic, provided that $R^{21}$ is not a saccharide or an oligosaccharide;

$L^2$ is selected from the group consisting of a covalent bond and a cleavable linker group;

$R^{22}$ is selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic, provided that R is not a saccharide or an oligosaccharide;

provided that when $L^2$ is a covalent bond and $R^{22}$ is hydrogen, then $R^{21}$ is selected from the group consisting of —C(O)N$R^{24}$$R^{25}$ and —C(O)O$R^{26}$; and further provided that when $R^{21}$ is hydrogen or —C(O)$R^{23}$ and $L^2$ is a covalent bond, then $R^{22}$ is not hydrogen.

In one embodiment, the noribogaine derivative is represented by Formula V:

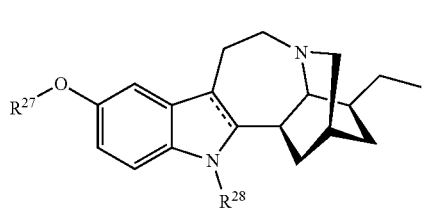

V or a pharmaceutically acceptable salt and/or solvate thereof, wherein:

⚏ refers to a single or a double bond provided that when ⚏ is a single bond, Formula V refers to the corresponding dihydro compound;

$R^{27}$ is hydrogen or SO$_2$O$R^{29}$;

$R^{28}$ is hydrogen or SO$_2$O$R^{29}$;

$R^{29}$ is hydrogen or $C_1$-$C_6$ alkyl;

provided that at least one of $R^{27}$ and $R^{28}$ is not hydrogen.

In one embodiment, the noribogaine derivative is represented by Formula VI:

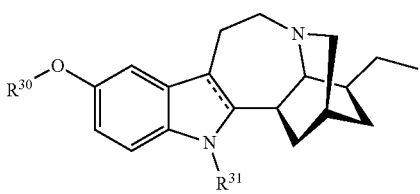

VI or a pharmaceutically acceptable salt and/or solvate thereof, wherein:

⚏ refers to a single or a double bond provided that when ⚏ is a single bond, Formula VI refers to the corresponding vicinal dihydro compound;

$R^{30}$ is hydrogen, a monophosphate, a diphosphate or a triphosphate; and $R^{31}$ is hydrogen, a monophosphate, a diphosphate or a triphosphate;

provided that both $R^{30}$ and $R^{31}$ are not hydrogen;

wherein one or more of the monophosphate, diphosphate and triphosphate groups of $R^{30}$ and $R^{31}$ are optionally esterified with one or more $C_1$-$C_6$ alkyl esters.

In some embodiments, the ibogaine or ibogaine derivative is represented by Formula VII:

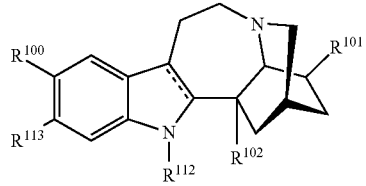

VII or a pharmaceutically acceptable salt and/or solvate thereof, wherein $R^{100}$ is H, halo, $C_1$-$C_3$ alkyl, substituted $C_1$-$C_3$ alkyl, O$R^{110}$, NH$_2$, NH$R^{110}$, N$R^{110}$$R^{111}$, NHC(O)$R^{110}$, or N$R^{110}$C(O)$R^{111}$;

$R^{101}$ is H, $C_1$-$C_3$ alkyl, substituted $C_1$-$C_3$ alkyl, $C_1$-$C_3$ alkoxy, $CH_2$—X—$CH_3$, or $(CH_2)_m R^{103}$;

$R^{102}$ is H, COOH, $COOR^{104}$, $(CH_2)_n OH$, $CH(OH)R^{105}$, $CH_2 OR^{105}$, $C(O)NH_2$, $C(O)NHR^{105}$, $C(O)NR^{105}R^{106}$, $C(O)NHNH_2$, $C(O)NHNHR^{105}$, $C(O)NHNR^{105}R^{106}$, $C(O)NR^{105}NH_2$, $C(O)NR^{105}NHR^{106}$, $C(O)NR^{105}NR^{106}R^{107}$, $C(O)NHNH(C(O)R^{105})$, $C(O)NHNR^{105}(C(O)R^{106})$, $C(O)NR^{105}NH(C(O)R^{106})$, $C(O)NR^{105}NR^{106}(C(O)R^{107})$, CN, or $C(O)R^{105}$;

$R^{103}$ is $C_1$-$C_3$ alkyl, benzyl, substituted $C_1$-$C_3$ alkyl, YH, $YR^{108}$, $YC(O)R^{108}$, $C(O)YR^{108}$, $C(O)NH_2$, $C(O)NHR^{108}$, $C(O)NR^{108}R^{109}$, $NH_2$, $NHR^{108}$, $NR^{108}R^{109}$, $NHC(O)R^{108}$, $O(CH_2)_p O(CH_2)_q O(CH_2)_r CH_3$ or $NR^{108}C(O)R^{109}$; $R^{104}$ is $C_1$-$C_6$ alkyl or $(CH_2 CH_2 O)_n CH_3$;

$R^{105}$, $R^{106}$, $R^{107}$, $R^{108}$, $R^{109}$, $R^{110}$, and $R^{111}$ are independently alkyl or substituted alkyl;

$R^{112}$ is H, alkyl, or substituted alkyl;

$R^{113}$ is H, $OR^{110}$, alkyl, or substituted alkyl;

X is O or NH;

Y is O or S;

m is an integer selected from 0-8;

each of n, p and q is 1, 2 or 3; and r is 0, 1 or 2.

In some embodiments, the ibogaine or ibogaine derivative is represented by Formula VIII:

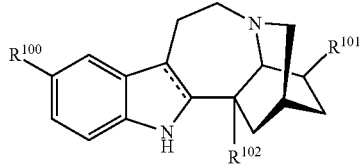

VIII or a pharmaceutically acceptable salt and/or solvate thereof, wherein $R^{100}$ is hydrogen or $C_1$-$C_3$ alkoxy, $R^{101}$ is hydrogen, $C_1$-$C_3$ alkyl, $C_1$-$C_3$ alkoxy, $(CH_2)_m OC(O)$alkyl, $(CH_2)_m OH$, $(CH_2)_m O$alkyl, $(CH_2)_m O(CH_2)_p O(CH_2)_q O(CH_2)_r CH_3$ or $CH_2$—Y—$CH_3$ where each of m, p and q is 1, 2 or 3; and r is 0, 1 or 2, Y is O or NH, and $R^{102}$ is H, $(CH_2)_n OH$, COOH, or $COOR^{104}$, where $R^{104}$ is $C_1$-$C_6$ alkyl or $(CH_2 CH_2 O)_n CH_3$, where n is 1, 2, or 3.

In one embodiment, $R^{100}$ is methoxy. In one embodiment, $R^{101}$ is ethyl. In one embodiment, $R^{101}$ is methoxy. In one embodiment, $R^{101}$ is $CH_2$—Y—$CH_3$ where Y is O. In one embodiment, $R^{101}$ is $CH_2$—Y—$CH_3$ where Y is NH. In one embodiment, $R^{102}$ is hydrogen. In one embodiment, In one embodiment, $R^{102}$ is $COOR^{104}$ and $R^{104}$ is methyl. In one embodiment, n=1. In a preferred embodiment, $R^{100}$, $R^{101}$ and $R^{102}$ are all not hydrogen. In one embodiment, when $R^{100}$ is methoxy and $R^{101}$ is hydrogen, then $R^{102}$ is COOH or $COOR^{104}$. In another embodiment, when $R^{100}$ is methoxy and $R^{101}$ is hydrogen, then X is $COOR^{104}$ where $R^{104}$ is $(CH_2 CH_2 O)CH_3$.

In one embodiment, $R^{102}$ is hydrogen.

In one embodiment, $R^{101}$ is H. In one embodiment, $R^{101}$ is $C_1$-$C_3$ alkyl, such as ethyl. In one embodiment, $R^{101}$ is $CH_2 CH_2 OH$. In one embodiment, $R^{101}$ is $CH_2 CH_2 OCH_3$. In one embodiment, $R^{101}$ is $CH_2 CH_2 OCH_2 Ph$. In one embodiment, $R^{101}$ is $CH_2 CH_2 OC(O)$alkyl. In one embodiment, $R^{101}$ is $CH_2 CH_2 O(CH_2)_p O(CH_2)_q O(CH_2)_r CH_3$.

In one embodiment, $R^{102}$ is $CH_2 OH$ and $CH(OH)R^{105}$. In one embodiment, $R^{102}$ is $CH_2 OR^{105}$. In one embodiment, $R^{102}$ is $CO_2 R^{105}$. In one embodiment, $R^{102}$ is $C(O)NH_2$, $C(O)NHR^{105}$, or $C(O)NR^{105}R^{106}$. In one embodiment, $R^{102}$ is $C(O)NHNH_2$, $C(O)NHNHR^{105}$, $C(O)NR^{105}NH_2$, $C(O)NHNR^{105}R^{106}$, $C(O)NHR^{105}NHR^{106}$, or $C(O)NR^{105}NR^{106}R^{107}$. In one embodiment, $R^{102}$ is $C(O)NHNH(C(O)R^{105})$, $C(O)NHNR^{105}(C(O)R^{106})$, $C(O)NR^{105}NH(C(O)R^{106})$, or $C(O)NR^{105}NR^{106}(C(O)R^{107})$. In one embodiment, $R^{102}$ is $C(O)R^{105}$.

In some embodiments, the ibogaine or ibogaine derivative is selected from:

| Name | Structure |
|---|---|
| coronaridine | 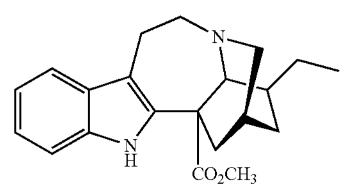 |
| 18-hydroxycoronaridine | 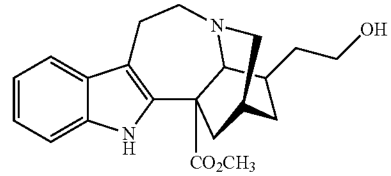 |
| 18-methoxycoronaridine | 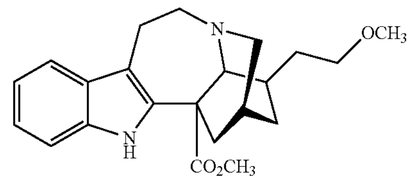 |

-continued
| Name | Structure |
|---|---|
| 18-benzyloxycoronaridine | 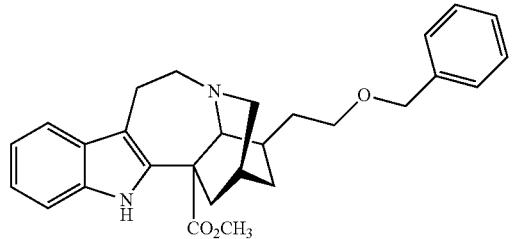 |
| 18-hydroxycoronaridine laurate | 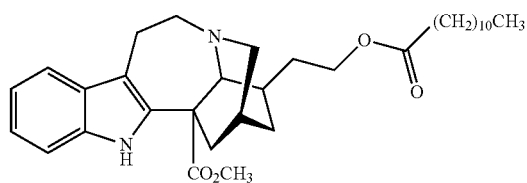 |
| 18-hydroxycoronaridine methoxyethoxymethyl ether | 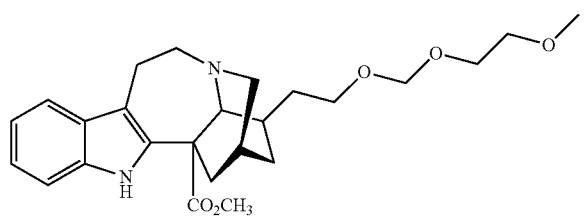 |
| 18-hydroxycoronaridine acetate | 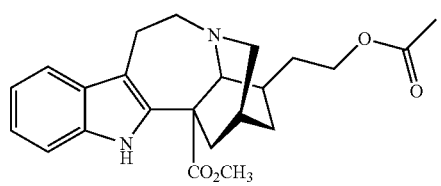 |
| voacangine | 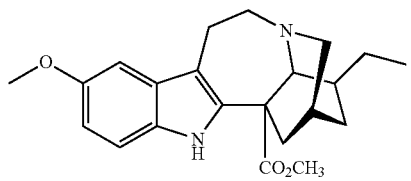 |
| 18-hydroxyvoacangine | 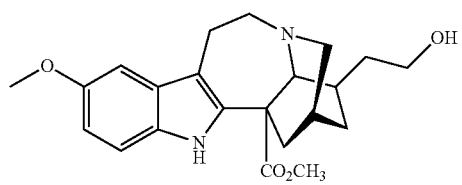 |
| 18-methoxyvoacangine | 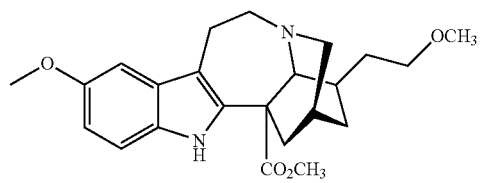 |

| Name | Structure |
|---|---|
| 18-benzyloxyvoacangine | 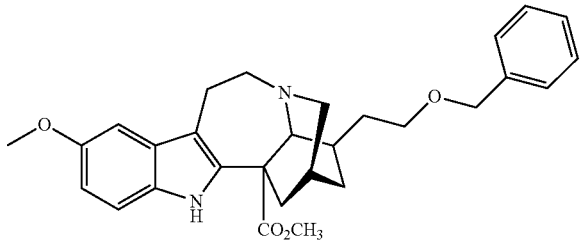 |
| 18-hydroxyvoacangine laurate | 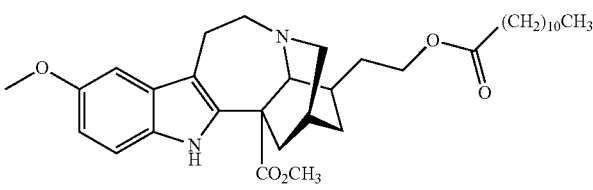 |
| 18-hydroxyvoacangine acetate | 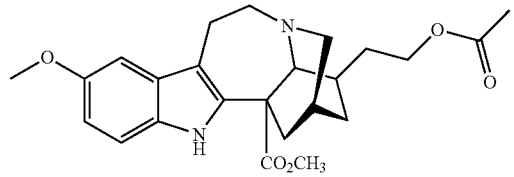 |
| 18-hydroxyvoacangine methoxyethoxymethyl ether | 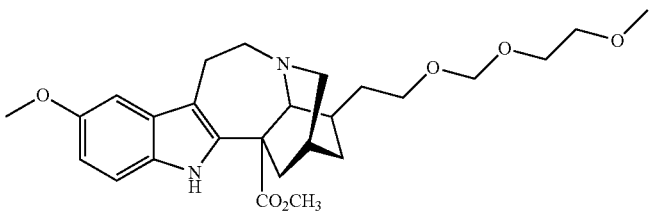 |
| conopharyngine | 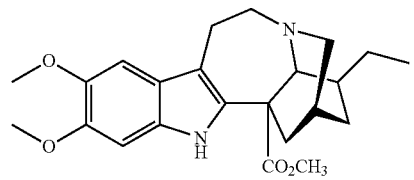 |
| 18-hydroxyconopharyngine | 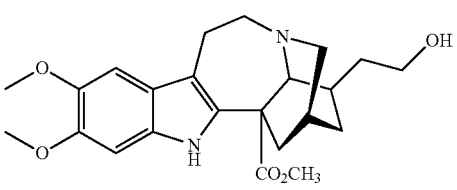 |
| 18-methoxyconopharyngine | 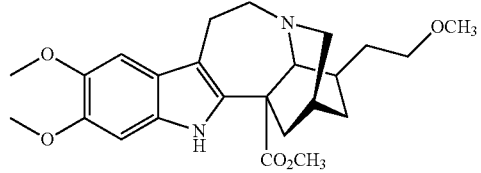 |

| Name | Structure |
|---|---|
| 18-benzyloxyconopharyngine | 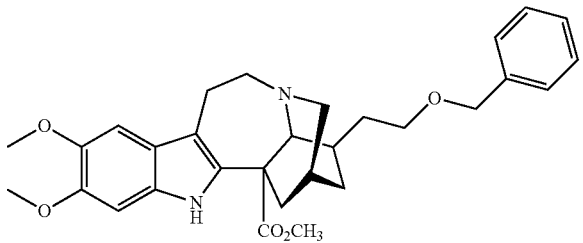 |
| 18-hydroxyconopharyngine laurate | 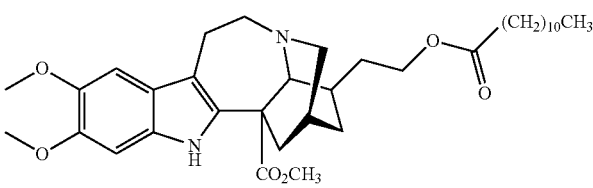 |
| 18-hydroxyconopharyngine acetate | 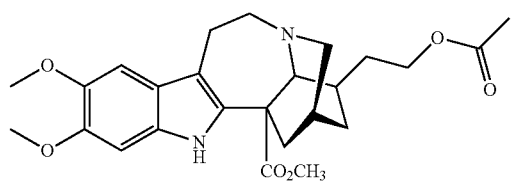 |
| 18-hydroxyconopharyngine methoxyethoxymethyl ether | 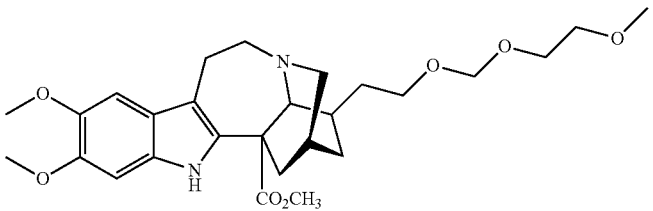 |
| ibogamine | 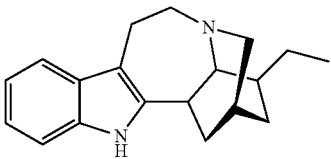 |
| 16-ethoxycarbonyl-18-hydroxyibogamine | 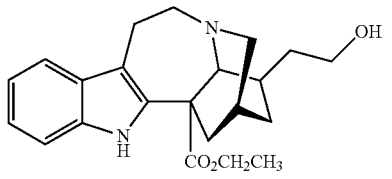 |
| 16-hydroxymethyl-18-hydroxyibogamine | 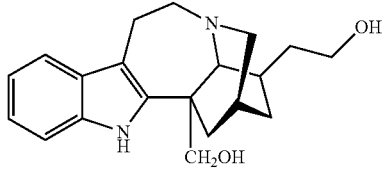 |
| 16-ethoxycarbonyl-18-methoxyibogamine | 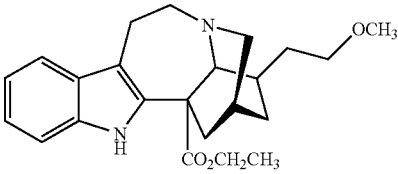 |

-continued
| Name | Structure |
|---|---|
| 16-hydroxymethyl-18-methoxyibogamine | 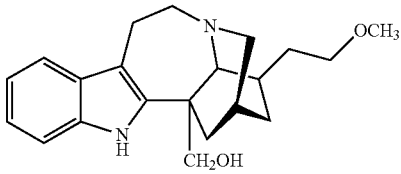 |
| 16-ethoxycarbonyl-18-benzyloxyibogamine | 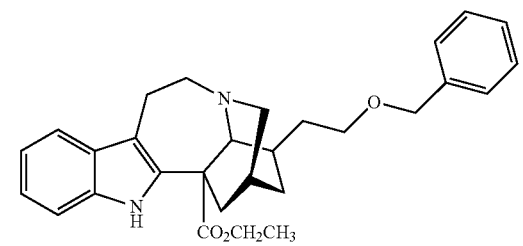 |
| 16-ethoxycarbonyl-18-hydroxyibogamine laurate | 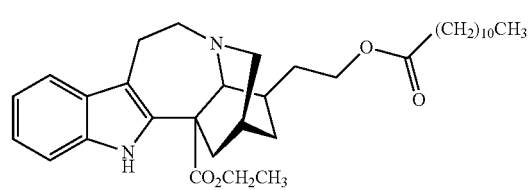 |
| 16-ethoxycarbonyl-18-hydroxyibogamine acetate | 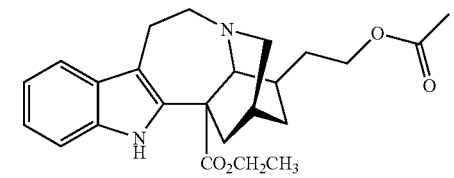 |
| 16-ethoxycarbonyl-18-hydroxyibogamine methoxyethoxymethyl ether | 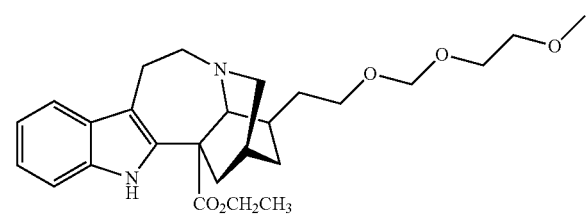 |
| ibogaine | 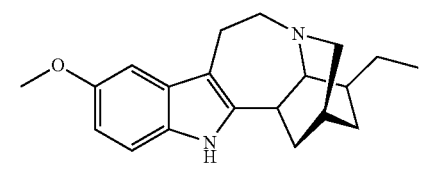 |
| 16-ethoxycarbonyl-18-hydroxyibogaine | 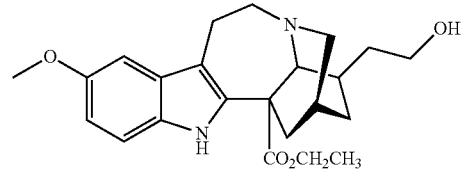 |
| 16-hydroxymethyl-18-hydroxyibogaine | 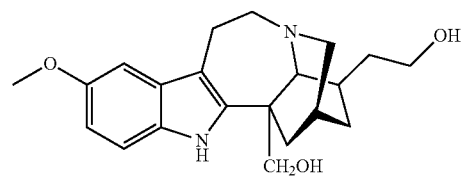 |

-continued
| Name | Structure |
|---|---|
| 16-ethoxycarbonyl-18-methoxyibogaine | 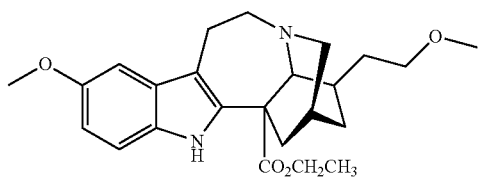 |
| 16-hydroxymethyl-18-methoxyibogaine | 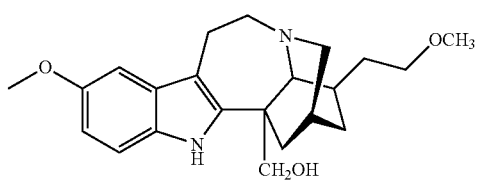 |
| 16-ethoxycarbonyl-18-benzyloxyibogaine | 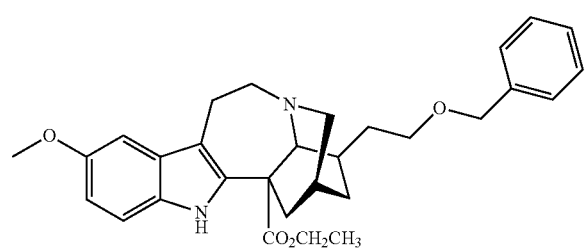 |
| 16-ethoxycarbonyl-18-hydroxyibogaine laurate | 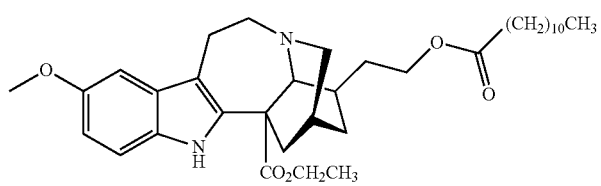 |
| 16-ethoxycarbonyl-18-hydroxyibogaine acetate | 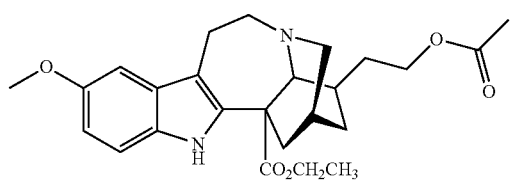 |
| 16-ethoxycarbonyl-18-hydroxyibogaine methoxyethoxymethyl ether | 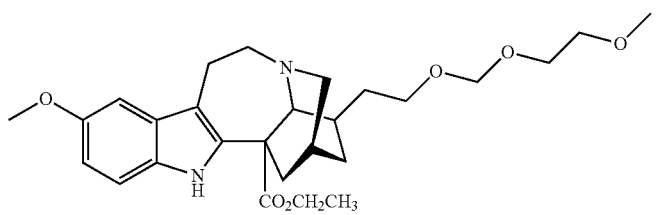 |
| ibogaline | 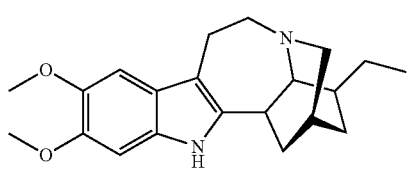 |
| 16-ethoxycarbonyl-18-hydroxyibogaline | 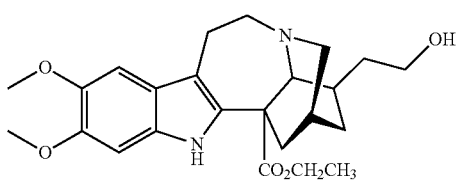 |

-continued
| Name | Structure |
|---|---|
| 16-hydroxymethyl-18-hydroxyibogaline | 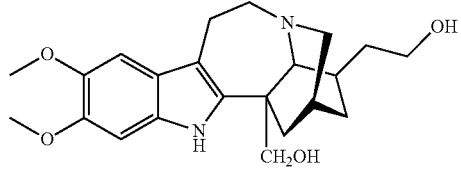 |
| 16-ethoxycarbonyl-18-methoxyibogaline | 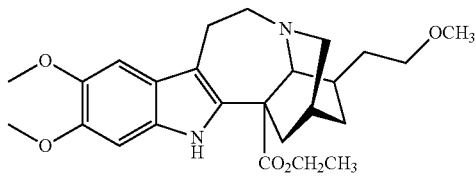 |
| 16-hydroxymethyl-18-methoxyibogaline | 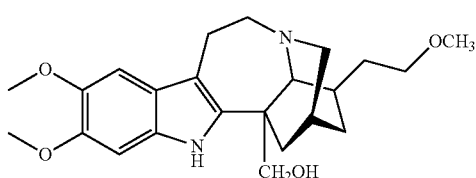 |
| 16-ethoxycarbonyl-18-benzyloxyibogaline | 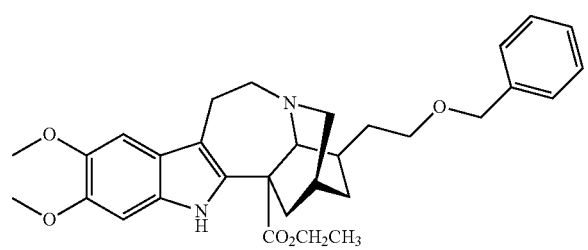 |
| 16-ethoxycarbonyl-18-hydroxyibogaline laurate | 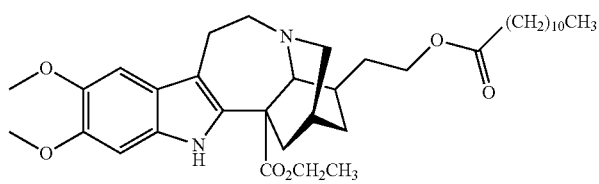 |
| 16-ethoxycarbonyl-18-hydroxyibogaline acetate | 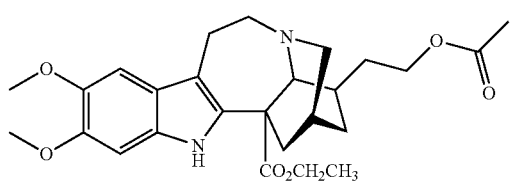 |
| 16-ethoxycarbonyl-18-hydroxyibogaline methoxyethoxymethyl ether | 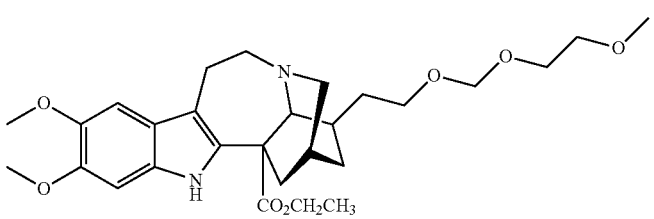 | and pharmaceutically acceptable salts and/or solvates thereof.

In one embodiment, the ibogaine derivative is:

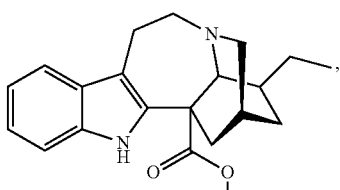

(coronaridine)

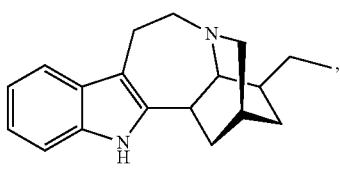

(ibogamine)

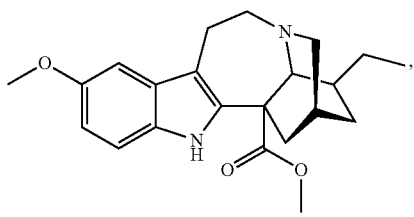

(voacangine)

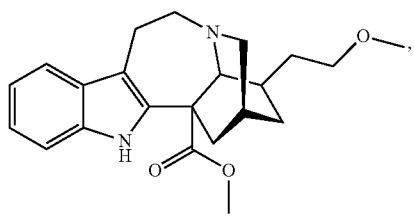

(18-methoxycoronaridine, 18-MC)

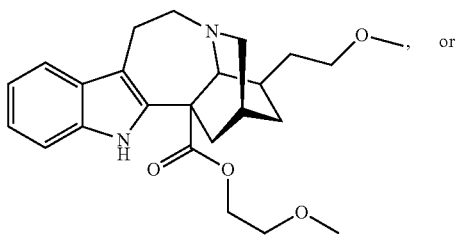

(2-Methoxyethyl-18-methoxycoronaridinate, ME-18-MC)

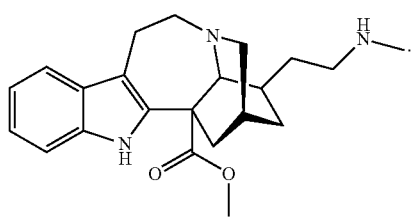

(18-Methylaminocoronaridine, 18-MAC)

III. Methods of the Invention

As will be apparent to the skilled artisan upon reading this disclosure, the present invention provides a method for potentiating the effect of an opioid analgesic in a patient undergoing or planning to undergo opioid analgesic therapy, comprising administering to the patient a dosage of iboga alkaloid or pharmaceutically acceptable salt and/or solvate thereof wherein the iboga alkaloid is dosed in an amount to potentiate the opioid while maintaining an acceptable QT interval prolongation.

In one aspect, the patient is naïve with respect to opioid treatment. That is, the patient has not been administered an opioid analgesic for a period of time such that any residual opioid in the blood stream is less than an amount to impart an analgesic effect to the patient. In one aspect, the patient has not been administered an opioid analgesic within two weeks and preferably within four weeks prior to administration of iboga alkaloid in combination with an opioid analgesic. It is to be understood that such a time period may differ based on the opioid, characteristics of the patient, and the like, and is readily determined by the skilled clinician.

In one aspect of this invention, a patient is treated with an addictive opioid analgesic to relieve the patient's pain. The pain may be of any type and from any source. In one embodiment, the patient is treated for acute pain. In one embodiment, the patient is treated for chronic pain. In one embodiment, the patient is treated for nociceptive pain. In one embodiment, the patient is treated for neuropathic pain. In some embodiments, the pain is caused by surgery, diabetes, trigeminal neuralgia, fibromyalgia, cancer, central pain syndrome, tissue damage, physical injury, and the like. In some embodiments, the source of the pain is unknown or unclear.

In one aspect of this invention, there is provided a method for potentiating the analgesic effect of an opioid analgesic in a patient undergoing or planning to undergo opioid analgesic therapy, the method comprising administering a potentiating amount of an iboga alkaloid or pharmaceutically acceptable salt and/or solvate thereof to potentiate the effect of the opioid as an analgesic, wherein the iboga alkaloid is dosed in an amount to potentiate the opioid while maintaining an acceptable QT interval. In particular, the potentiating amount of the iboga alkaloid or pharmaceutically acceptable salt or solvate thereof is such that the QT interval prolongation experienced by the patient is less than about 60 ms, less than about 50 ms, preferably less than 30 ms, more preferably less than 20 ms.

In one embodiment, maximum QT interval as a result of iboga alkaloid treatment is less than about 500 ms, less than about 490 ms, less than about 480 ms, less than about 470 ms, less than about 460 ms, less than about 450 ms, less than about 440 ms, or less than about 430 ms.

In one aspect of this invention, there is provided a method for reducing tolerance to an opioid analgesic in a patient who exhibits tolerance to an opioid during opioid analgesic therapy, the method comprising administering an effective amount of an iboga alkaloid or pharmaceutically acceptable salt and/or solvate thereof to reduce tolerance to the opioid, wherein the iboga alkaloid is dosed in an amount to potentiate the opioid while maintaining an acceptable QT interval and/or QT interval prolongation.

In one aspect of this invention, there is provided a method for preventing dependence on an opioid analgesic in a patient undergoing or planning to undergo opioid analgesic therapy, the method comprising administering an effective amount of an iboga alkaloid or pharmaceutically acceptable salt and/or solvate thereof to prevent dependence on the opioid, wherein the iboga alkaloid is dosed in an amount to potentiate the opioid while maintaining an acceptable QT interval and/or QT interval prolongation.

In one aspect of this invention, there is provided a method for inhibiting addiction to an opioid analgesic in a patient undergoing or planning to undergo opioid analgesic therapy, the method comprising administering an effective amount of an iboga alkaloid or pharmaceutically acceptable salt and/or solvate thereof to prevent addiction to the opioid, wherein the iboga alkaloid is dosed in an amount to potentiate the opioid while maintaining an acceptable QT interval and/or QT interval prolongation.

In one aspect, this disclosure relates to a method for maintaining efficacy of an opioid analgesic in a patient, the method comprising periodically administering to the patient an opioid and an initial amount of noribogaine for a period of time, determining whether the patient exhibits tolerance to the opioid, and increasing the amount of noribogaine administered without increasing the amount of opioid administered when the patient exhibits tolerance to the opioid. In one embodiment, the amount of noribogaine is increased after a predetermined period of time.

In one aspect, this disclosure relates to a method for maintaining efficacy of an opioid analgesic in a patient, the method comprising periodically administering to the patient an opioid and noribogaine for a period of time, determining whether the patient exhibits tolerance to the opioid, and increasing the amount of opioid administered with or without increasing the amount of norbogaine administered when the patient exhibits tolerance to the opioid. In one embodiment, the amount of opioid and/or noribogaine is increased after a predetermined period of time.

In one aspect, this disclosure relates to a method for determining the amount of noribogaine required for potentiation of an opioid by evaluating tolerance to the opioid and the amount of opioid administered to a patient.

In one aspect, this disclosure relates to a method for determining the amount of opioid required to be administered to a patient in order to have an analgesic effect, when the opioid is to be administered after administration of noribogaine.

In one aspect, this disclosure relates to a method to decrease respiratory depression in a patient by an opioid analgesic by co-administering noribogaine to reduce the amount of opioid required to be administered to the patient.

As used herein, "preventing" or "reducing" tolerance includes increasing the amount of time to opioid tolerance (i.e., the duration of opioid treatment before tolerance occurs); increasing the dose of opioid at which tolerance occurs; and/or preventing tolerance from occurring at any duration or dose of opioid administration.

As used herein, "preventing" or "reducing" dependence includes increasing the amount of time to opioid dependence (i.e., the duration of opioid treatment before dependence occurs); increasing the dose of opioid at which dependence occurs; and/or preventing dependence from occurring at any duration or dose of opioid administration.

The efficacy of a particular amount of an opioid analgesic to treat pain (have an analgesic effect) in a patient can be measured by a variety of well-known methods. These include, for example, animal studies to provide an objective measure (e.g., tail flick assay, foot splay assay,), as well as pain screening instruments (e.g., Brief Pain Inventory, Likert Scale, McGill Pain Questionnaire, Patient Global Impression of Change and Clinical Global Impression of Change, the Short Form-36 Quality of Life Questionnaire scores, the Profile of Mood States, or the Roland Morris Disability Scale); Pain Assessment and Documentation Tool (e.g., to monitor on-going pain assessment); and other methods well-known in the art.

Tolerance or development of tolerance to an opioid can be measured by any method known in the art, now or in the future. For example, the Intracranial Self-Stimulation (ICSS) is a test of tolerance in rodents. In humans, tests such as the cold pressor test or experimental heat pain may be administered before and after treatment with analgesic to determine tolerance and/or efficacy. Differences in the patient screening instruments may also be used for this purpose. Similarly, dependence or development of dependence may be determined by any method known in the art, now or in the future.

In some embodiments, the amount of opioid and/or noribogaine administered to the patient is titrated over time, for example based on the opioid analgesic administered, the amount of pain experienced by the patient (before and/or after opioid administration), the amount of tolerance and/or dependence experienced by the patient, genetic factors (likelihood of dependence or tolerance to an opioid analgesic, optimal opioid analgesic for the patient, etc.), length of time the opioid has been administered to the patient, length of time the opioid is expected to be administered to the patient, duration of noribogaine treatment (actual or expected), and the like. Such titration is within the abilities of the skilled clinician.

In one embodiment, the QT interval is not prolonged more than about 60 ms. In one embodiment, the QT interval is not prolonged more than about 50 ms. In one embodiment, the QT interval is not prolonged more than about 30 ms. In a preferred embodiment, the QT interval is not prolonged more than about 20 ms. In one embodiment, the QT interval is not prolonged more than about 15 ms. In an especially preferred embodiment, the QT interval is not prolonged more than about 10 ms.

In one embodiment, the average serum concentration of the iboga alkaloid is less than about 150 ng/mL. In one embodiment, the average serum concentration of the iboga alkaloid is less than about 100 ng/mL. In a preferred embodiment, the average serum concentration of the iboga alkaloid is less than about 50 ng/mL. In one embodiment, the average serum concentration of the iboga alkaloid is less than about 20 ng/mL. In one embodiment, the average serum concentration of the iboga alkaloid is less than about 10 ng/mL. The ranges include extremes as well as any subranges.

In one embodiment, the serum concentration is less than about 10,000 ng*hour/mL (area under the curve for a period of time, AUC/t) over the period during which the iboga alkaloid is administered. In a preferred embodiment, the serum concentration is less than about 8,000 ng*hour/mL (AUC/t) over the period during which the iboga alkaloid is administered. In one embodiment, the serum concentration is less than about 6,000 ng*hour/mL (AUC/t) over the period during which the iboga alkaloid is administered. The ranges include extremes as well as any subranges.

In another embodiment, a unit dose of iboga alkaloid or salt or solvate thereof is administered. In one embodiment, the unit dose comprises about 0.001 mg to about 80 mg iboga alkaloid per day. In one embodiment, the unit dose comprises about 0.001 mg to about 50 mg iboga alkaloid per day. In one embodiment, the unit dose comprises about 0.001 mg to about 30 mg iboga alkaloid per day. In one embodiment, the unit dose comprises about 0.001 mg to about 20 mg iboga alkaloid per day. In one embodiment, the unit dose comprises about 0.01 mg to about 50 mg iboga alkaloid per day. In one embodiment, the unit dose comprises about 0.01 mg to about 60 mg iboga alkaloid per day. In one embodiment, the unit dose comprises about 0.01 mg to about 70 mg iboga alkaloid per day. In one embodiment, the unit dose comprises about 0.01 mg to about 80 mg iboga alkaloid per day. In one embodiment, the unit dose comprises about 0.01 mg to about 30 mg iboga alkaloid per day. In one embodiment, the unit dose comprises about 0.01 mg to about 20 mg iboga alkaloid per day. The ranges include extremes as well as any subranges. In one embodiment, the unit dose further comprises an opioid analgesic. It is to be understood that the term "unit dose" means a dose sufficient to provide therapeutic results whether given all at once or serially over a period of time.

In some embodiments, the amount of iboga alkaloid administered is independent of the amount of opioid administered. In some embodiments, the amount of iboga alkaloid administered is dependent on the amount of opioid administered. In one embodiment, the iboga alkaloid to opioid ratio is between about 100:1 and about 1:100. In one embodiment, the iboga alkaloid to opioid ratio is between about 100:1 and about 1:90. In one embodiment, the iboga alkaloid to opioid ratio is between about 100:1 and about 1:80. In one embodiment, the iboga alkaloid to opioid ratio is between about 100:1 and about 1:70. In one embodiment, the iboga alkaloid to opioid ratio is between about 100:1 and about 1:60. In one embodiment, the iboga alkaloid to opioid ratio is between about 100:1 and about 1:50. In one embodiment, the iboga alkaloid to opioid ratio is between about 100:1 and about 1:40. In one embodiment, the iboga alkaloid to opioid ratio is between about 100:1 and about 1:30. In one embodiment, the iboga alkaloid to opioid ratio is between about 100:1 and about 1:10. In one embodiment, the iboga alkaloid to opioid ratio is between about 100:1 and about 1:1. In one embodiment, the iboga alkaloid to opioid ratio is between about 10:1 and about 1:100. In one embodiment, the iboga alkaloid to opioid ratio is between about 10:1 and about 1:90. In one embodiment, the iboga alkaloid to opioid ratio is between about 10:1 and about 1:80. In one embodiment, the iboga alkaloid to opioid ratio is between about 10:1 and about 1:70. In one embodiment, the iboga alkaloid to opioid ratio is between about 10:1 and about 1:60. In one embodiment, the iboga alkaloid to opioid ratio is between about 10:1 and about 1:50. In one embodiment, the iboga alkaloid to opioid ratio is between about 10:1 and about 1:40. In one embodiment, the iboga alkaloid to opioid ratio is between about 10:1 and about 1:30. In one embodiment, the iboga alkaloid to opioid ratio is between about 10:1 and about 1:20. In a preferred embodiment, the iboga alkaloid to opioid ratio is between about 10:1 and about 1:10. In one embodiment, the iboga alkaloid to opioid ratio is between about 10:1 and about 1:1. The ranges include extremes as well as any subranges.

In some embodiments, the patient is administered periodically, such as once, twice, three times, four times or five times daily with the iboga alkaloid or a pharmaceutically acceptable salt and/or solvate thereof. In some embodiments, the administration is once daily, or once every second day, once every third day, three times a week, twice a week, or once a week. The iboga alkaloid may be administered concurrently with or proximate in time to administration of the opioid analgesic. The dosage and frequency of the administration depends on the route of administration, dosage, age, and body weight of the patient, condition of the patient, opioid analgesic, length of time of analgesic treatment, and the like, without limitation. Determination of dosage and frequency suitable for the present technology can be readily made a qualified clinician.

In some embodiments, it is contemplated that an increase in the amount of iboga alkaloid administered may be required during treatment. In one embodiment, the amount of iboga alkaloid administered to the patient changes over time. In one embodiment, the amount of iboga alkaloid is increased by about 1% to about 400% at some time after the iboga alkaloid treatment commences. In one embodiment, the amount of iboga alkaloid is increased by about 0.001 mg, 0.01 mg, 0.1 mg, 1 mg, 5 mg, about 10 mg, about 20 mg, or about 30 mg at some time after the iboga alkaloid treatment commences. In one embodiment, the increased dose is incremental, i.e., the dose of iboga alkaloid is increased gradually (incrementally) over time. In one embodiment the incremental or gradient increase of iboga alkaloid is administered with a concomitant incremental or gradient decrease of opioid analgesic. For example, the opioid analgesic can be the sole medicament provided to the patient and over time the amount of iboga alkaloid is introduced while concomitantly reducing the amount of opioid analgesic. In one embodiment, the dose of iboga alkaloid is increased all at once. In one embodiment, the dose of iboga alkaloid varies (up and down) during treatment. In one embodiment, the increased amount of iboga alkaloid administered to the patient does not exceed about 80 mg per day. In a preferred embodiment, the increased amount of iboga alkaloid administered to the patient does not exceed about 50 mg per day.

In one aspect, the amount of iboga alkaloid administered per day is increased between one day and about two weeks after iboga alkaloid treatment commences. In one embodiment, the amount of iboga alkaloid administered per day is increased about one week to about two weeks after iboga alkaloid treatment commences. In one embodiment, the amount of iboga alkaloid administered per day is increased about 3 days after iboga alkaloid treatment commences. In one embodiment, the amount of iboga alkaloid administered per day is increased about 4 days after iboga alkaloid treatment commences. In one embodiment, the amount of iboga alkaloid administered per day is increased about 5 days after iboga alkaloid treatment commences. In one embodiment, the amount of iboga alkaloid administered per day is increased about 6 days after iboga alkaloid treatment commences. In one embodiment, the amount of iboga alkaloid administered per day is increased about one week after iboga alkaloid treatment commences. In one embodiment, the amount of iboga alkaloid administered per day is increased about 10 days after iboga alkaloid treatment commences. In one embodiment, the amount of iboga alkaloid administered per day is increased about 2 weeks after iboga alkaloid treatment commences.

In one embodiment, the amount of iboga alkaloid administered per day is further increased between two days and about two weeks after the first increase (or an increase subsequent to the first increase). In one embodiment, the amount of iboga alkaloid administered per day is increased about 2 days after the first increase (or a subsequent increase). In one embodiment, the amount of iboga alkaloid administered per day is increased about 4 days after the first increase (or a subsequent increase). In one embodiment, the amount of iboga alkaloid administered per day is increased about 5 days after the first increase (or a subsequent increase). In one embodiment, the amount of iboga alkaloid administered per day is increased about 6 days after the first increase (or a subsequent increase). In one embodiment, the amount of iboga alkaloid administered per day is increased about 1 week after the first increase (or a subsequent increase). In one embodiment, the amount of iboga alkaloid administered per day is increased about 10 days after the first increase (or a subsequent increase). In one embodiment, the amount of iboga alkaloid administered per day is increased about 2 weeks after the first increase (or a subsequent increase).

It is further contemplated that less opioid analgesic will be required to treat pain when the patient is being administered the iboga alkaloid. For example, between about 25% and about 75% of the original or usual opioid dose can be administered to a patient. The "usual" opioid dose refers to the dose that would be prescribed by the clinician for the amount and type of pain in the patient, and may depend on a variety of other factors (e.g., size, weight, sex, and/or health of the patient to be treated). In one embodiment, between about 25% and about 65% of the original or usual opioid dose is administered. In one embodiment, between about 25% and about 50% of the original or usual opioid dose is administered. In one embodiment, between about 35% and about 75% of the original or usual opioid dose is administered. In one embodiment, between about 45% and about 75% of the original or usual opioid dose is administered. In one embodiment, between about 50% and about 75% of the original or usual opioid dose is administered. The ranges include extremes as well as any subranges.

It is understood that patients receiving treatment with an iboga alkaloid may exhibit different (i.e., patient-specific) levels of tolerance to the iboga alkaloid and/or opioid analgesic. As such, patients may be monitored during all or some duration of the administration period by a skilled clinician to ensure the iboga alkaloid and/or opioid analgesic is dosed in an amount to potentiate the opioid while maintaining an acceptable QT interval prolongation and without a resultant respiratory depression. During treatment with the iboga alkaloid, the opioid analgesic may require an adjustment up or down. Such adjustments are easily determined by the skilled clinician, based on the patient's needs.

In a preferred embodiment, the iboga alkaloid is administered for a period of time, and then stopped. In one embodiment, the iboga alkaloid is administered for about 2 weeks to about 5 weeks before stopping. In one embodiment, the iboga alkaloid is administered for about 2 weeks before stopping. In one embodiment, the iboga alkaloid is administered for about 10 days before stopping. In one embodiment, the iboga alkaloid is administered for about 3 weeks before stopping. In one embodiment, the iboga alkaloid is administered for about 4 weeks before stopping. In one embodiment, the iboga alkaloid is administered for about 5 weeks before stopping. In one embodiment, the opioid analgesic is administered to the patient after the iboga alkaloid administration is stopped. In one embodiment, administration of the opioid analgesic ceases at approximately the same time that administration of the iboga alkaloid is stopped.

Some patients, for example those with acute pain, may not need to restart iboga alkaloid administration. For example, such patients may discontinue opioid use after a short time. Other patients, particularly those receiving long-term analgesic treatment, may restart iboga alkaloid administration.

In one embodiment, the iboga alkaloid is administered for a subsequent period of time after a break in administration. In one embodiment, the break in administration lasts between 2 days and about 3 weeks. In one embodiment, the break in administration lasts between 1 week and about 3 weeks. In one embodiment, the break in administration lasts between 2 weeks and about 3 weeks. The subsequent period of time may be the same amount of time as the previous amount of time, or longer or shorter. In one embodiment, the iboga alkaloid is administered for a subsequent period of time, and then stopped. In one embodiment, the amount of opioid analgesic administered to the patient is increased during the break. In one embodiment, the amount of opioid analgesic is not increased during the break. When the amount of opioid analgesic administered to the patient is increased during the break, that amount is preferably decreased once iboga alkaloid administration is restarted.

Iboga alkaloid or a pharmaceutically acceptable salt and/or solvate thereof, suitable for administration in accordance with the methods provide herein, can be suitable for a variety of delivery modes including, without limitation, oral and transdermal delivery. Compositions suitable for internal, pulmonary, rectal, nasal, vaginal, lingual, intravenous, intra-arterial, intramuscular, intraperitoneal, intracutaneous and subcutaneous routes may also be used. Possible dosage forms include tablets, capsules, pills, powders, aerosols, suppositories, parenterals, and oral liquids, including suspensions, solutions and emulsions. Sustained release dosage forms may also be used. All dosage forms may be prepared using methods that are standard in the art (see e.g., Remington's Pharmaceutical Sciences, 16th ed., A. Oslo editor, Easton Pa. 1980).

In one embodiment, the iboga alkaloid and opioid are administered in the same composition (e.g., unit dose). It is contemplated that administration using the same composition will increase patient compliance with respect to iboga alkaloid administration. It is further contemplated that compositions comprising an opioid analgesic in combination with an iboga alkaloid will deter or prevent abuse of the opioid, e.g., by an opioid-addicted individual. The individual may be the patient or a different individual.

In one embodiment, the iboga alkaloid and opioid are administered in different compositions. It is contemplated that administration as separate doses allows for more personalized dosing of the iboga alkaloid. Separate dosings is especially appropriate in a clinical setting (e.g., inpatient setting), where patient compliance is not an issue and/or where individualized therapy is important.

As would be understood by one of skill in the art, the opioid analgesic dose is dependent on multiple factors, including the size/weight of the patient; type of pain to be treated; opioid analgesic used; health of the patient; other medications being administered to the patient; degree of tolerance, dependence, or addiction to the opioid; and the like. In one embodiment, the opioid dose is within those considered safe and effective in the art, for example as described in the Agency Medical Directors' Group 2010 Opioid Dosing Guideline (accessible at www.agencymeddirectors.wa.gov/opioiddosing.asp). Proper opioid dosing can be determined by the skilled clinician.

In one embodiment, potentiation of the effect of the opioid analgesic by the iboga alkaloid results in a lower dosage prescribed for the patient, and/or reduced or delayed need for increases in the opioid dose. For example, the patient may require no increase in the opioid dose, a smaller incremental increase in the opioid dose, and/or a longer time to such an increase than without iboga alkaloid administration.

In one embodiment, the iboga alkaloid is noribogaine or a noribogaine derivative as described herein, or a pharmaceutically acceptable salt and/or solvate thereof. In one embodiment, the iboga alkaloid is ibogaine or an ibogaine derivative as described herein, or a pharmaceutically acceptable salt and/or solvate thereof.

In a preferred embodiment, iboga alkaloid or a pharmaceutically acceptable salt and/or solvate thereof is administered orally, which may conveniently be provided in tablet, caplet, sublingual, liquid or capsule form. In certain embodiments, the iboga alkaloid is provided as the HCL salt of the iboga alkaloid (e.g., noribogaine HCl), with dosages reported as the amount of free base iboga alkaloid. In some embodiments, the iboga alkaloid HCl is provided in hard gelatin capsules containing only iboga alkaloid HCl with no excipients. In some embodiments, the capsule further comprises an opioid analgesic.

The patient may be receiving any addictive opioid analgesic for the treatment of pain. In a preferred embodiment, the opioid analgesic is selected from the group consisting of fentanyl, hydrocodone, hydromorphone, morphine, oxycodone, buprenorphine, codeine, heroin, thebaine, buprenorphine, methadone, meperidine, tramadol, tapentadol, levorphanol, sufentanil, pentazocine, oxymorphone, and derivatives of each thereof.

Unit Dose and Kit of Parts

One aspect of this invention is directed to a unit dose of an iboga alkaloid for the potentiation of the effect of an opioid analgesic, wherein the unit dose comprises a composition comprising an iboga alkaloid or salt and/or solvate thereof, wherein the iboga alkaloid is dosed in an amount to potentiate the opioid while maintaining an acceptable QT interval prolongation. In a preferred embodiment, the unit dose further comprises an opioid analgesic.

In one aspect is provided a kit of parts for potentiation of the analgesic effect of an opioid analgesic, wherein the kit comprises a composition comprising an iboga alkaloid or salt and/or solvate thereof and a means for administering the composition to a patient in need thereof. In a preferred embodiment, the kit of parts further comprises an opioid analgesic. In a preferred embodiment, the opioid analgesic is provided in the same composition (e.g., unit dose) as the iboga alkaloid. In one embodiment, the opioid analgesic is provided in a separate composition from the iboga alkaloid. The means for administration to a patient can include, for example, any one or combination of noribogaine, or a noribogaine derivative, or a pharmaceutically acceptable salt and/or solvate thereof, a transdermal patch, a syringe, a needle, an IV bag comprising the composition, a vial comprising the composition, an inhaler comprising the composition, etc. In one embodiment, the kit of parts further comprises instructions for dosing and/or administration of the composition.

In some embodiments, the kit of parts includes a composition comprising iboga alkaloid and opioid analgesic at a ratio between about 100:1 and about 1:100. In one embodiment, the iboga alkaloid to opioid ratio is between about 100:1 and about 1:90. In one embodiment, the iboga alkaloid to opioid ratio is between about 100:1 and about 1:80. In one embodiment, the iboga alkaloid to opioid ratio is between about 100:1 and about 1:70. In one embodiment, the iboga alkaloid to opioid ratio is between about 100:1 and about 1:60. In one embodiment, the iboga alkaloid to opioid ratio is between about 100:1 and about 1:50. In one embodiment, the iboga alkaloid to opioid ratio is between about 100:1 and about 1:40. In one embodiment, the iboga alkaloid to opioid ratio is between about 100:1 and about 1:30. In one embodiment, the iboga alkaloid to opioid ratio is between about 100:1 and about 1:10. In one embodiment, the iboga alkaloid to opioid ratio is between about 100:1 and about 1:1. In one embodiment, the iboga alkaloid to opioid ratio is between about 10:1 and about 1:100. In one embodiment, the iboga alkaloid to opioid ratio is between about 10:1 and about 1:90. In one embodiment, the iboga alkaloid to opioid ratio is between about 10:1 and about 1:80. In one embodiment, the iboga alkaloid to opioid ratio is between about 10:1 and about 1:70. In one embodiment, the iboga alkaloid to opioid ratio is between about 10:1 and about 1:60. In one embodiment, the iboga alkaloid to opioid ratio is between about 10:1 and about 1:50. In one embodiment, the iboga alkaloid to opioid ratio is between about 10:1 and about 1:40. In one embodiment, the iboga alkaloid to opioid ratio is between about 10:1 and about 1:30. In one embodiment, the iboga alkaloid to opioid ratio is between about 10:1 and about 1:20. In a preferred embodiment, the iboga alkaloid to opioid ratio is between about 10:1 and about 1:10. In one embodiment, the iboga alkaloid to opioid ratio is between about 10:1 and about 1:1. The ranges include extremes as well as any subranges.

The composition may include opioid analgesic at any amount. For example, in some embodiments, the composition comprises about 1 mg to about 250 mg opioid analgesic. Preferably, the composition comprises about 5 mg to about 250 mg opioid analgesic. As would be understood by one skilled in the art, the amount of opioid analgesic in the composition is dependent on the opioid analgesic, as well as other considerations (e.g., weight of patient, age, tolerance to or dependence on an opioid, degree of pain, and the like).

In some aspects, the invention is directed to a kit of parts for administration of the composition (i.e., iboga alkaloid and/or opioid), the kit comprising multiple delivery vehicles, wherein each delivery vehicle contains a discrete amount of iboga alkaloid or pharmaceutically acceptable salt and/or solvate thereof, and optionally an opioid analgesic, and further wherein each delivery vehicle is identified by the amount of iboga alkaloid and/or opioid provided therein; and optionally further comprising a dosing treatment schedule in a readable medium. In some embodiments, the dosing treatment schedule includes the amount of iboga alkaloid required to potentiate the action of a given opioid and/or to achieve a target serum level. In some embodiments, the kit of parts includes a dosing treatment schedule that provides an attending clinician the ability to select a dosing regimen of iboga alkaloid based on criteria such as, without limitation, the opioid analgesic administered, sex of the patient, mass of the patient, and the serum level that the clinician desires to achieve. In some embodiments, the dosing treatment schedule further provides information corresponding to the volume of blood in a patient based upon weight (or mass) and sex of the patient. In an embodiment, the storage medium can include an accompanying pamphlet or similar written information that accompanies the unit dose form in the kit. In an embodiment, the storage medium can include electronic, optical, or other data storage, such as a non-volatile memory, for example, to store a digitally-encoded machine-readable representation of such information.

The term "delivery vehicle" as used herein refers to any formulation that can be used for administration of iboga alkaloid or pharmaceutically acceptable salt and/or solvate thereof to a patient. The delivery vehicle optionally comprises an opioid analgesic. Non-limiting, exemplary delivery vehicles include caplets, pills, capsules, tablets, powder, liquid, or any other form by which the drug can be administered. Delivery vehicles may be intended for administration by oral, inhaled, injected, or any other means.

The term "readable medium" as used herein refers to a representation of data that can be read, for example, by a human or by a machine. Non-limiting examples of human-readable formats include pamphlets, inserts, or other written forms. Non-limiting examples of machine-readable formats include any mechanism that provides (i.e., stores and/or transmits) information in a form readable by a machine (e.g., a computer, tablet, and/or smartphone). For example, a machine-readable medium includes read-only memory (ROM); random access memory (RAM); magnetic disk storage media; optical storage media; and flash memory devices. In one embodiment, the machine-readable medium is a CD-ROM. In one embodiment, the machine-readable medium is a USB drive. In one embodiment, the machine-readable medium is a Quick Response Code (QR Code) or other matrix barcode.

In some aspects, the machine-readable medium comprises software that contains information regarding dosing schedules for the unit dose form of iboga alkaloid or pharmaceutically acceptable salt and/or solvate thereof, and optionally other drug information. In some embodiments, the software may be interactive, such that the attending clinician or other medical professional can enter patient information. In a non-limiting example, the medical professional may enter the weight and sex of the patient to be treated, and the software program provides a recommended dosing regimen based on the information entered. The amount and timing of iboga alkaloid recommended to be delivered will be within the dosages as provided herein, and/or those that result in the serum concentrations as provided herein.

In some embodiments, the kit of parts comprises multiple delivery vehicles in a variety of dosing options. For example, the kit of parts may comprise pills or tablets in multiple dosages of iboga alkaloid or pharmaceutically acceptable salt and/or solvate thereof and/or opioid analgesic per pill. Each pill is labeled such that the medical professional and/or patient can easily distinguish different dosages. Labeling may be based on printing or embossing on the pill, shape of the pill, color of pill, the location of the pill in a separate, labeled compartment within the kit, and/or any other distinguishing features of the pill. In some embodiments, all of the delivery vehicles within a kit are intended for one patient. In some embodiments, the delivery vehicles within a kit are intended for multiple patients.

One aspect of this invention is directed to a kit of parts for the potentiation of the analgesic effect of an opioid analgesic in a patient undergoing or planning to undergo opioid analgesic therapy, wherein the kit comprises a unit dose form of iboga alkaloid or salt and/or solvate thereof. The unit dose form provides a patient with an average serum level of iboga alkaloid of less than about 80 ng/mL. In a preferred embodiment, the unit dose form provides a patient with an average serum level of iboga alkaloid of less than about 50 ng/mL.

In one embodiment, the unit dose of iboga alkaloid is from about 0.001 mg to about 50 mg per day. In a preferred embodiment, the unit dose of iboga alkaloid is from about 0.001 mg to about 30 mg per day. In another embodiment, the unit dose of iboga alkaloid is from about 0.001 mg to about 20 mg per day. In another embodiment, the unit dose of iboga alkaloid is from about 0.001 mg to about 10 mg per day. In another embodiment, the unit dose of iboga alkaloid is from about 0.001 mg to about 5 mg per day. In another embodiment, the unit dose of iboga alkaloid is from about 0.001 mg to about 1 mg per day. In another embodiment, the unit dose of iboga alkaloid is from about 0.001 mg to about 0.1 mg per day. In another embodiment, the unit dose of iboga alkaloid is from about 0.001 mg to about 0.01 mg per day. The ranges include both extremes as well as any subranges there between.

In another embodiment, the unit dose of iboga alkaloid is from about 0.01 mg to about 50 mg per day. In another embodiment, the unit dose of iboga alkaloid is from about 0.01 mg to about 30 mg per day. In another embodiment, the unit dose of iboga alkaloid is from about 0.01 mg to about 20 mg per day. In another embodiment, the unit dose of iboga alkaloid is from about 0.01 mg to about 10 mg per day. In another embodiment, the unit dose of iboga alkaloid is from about 0.01 mg to about 5 mg per day. In another embodiment, the unit dose of iboga alkaloid is from about 0.01 mg to about 1 mg per day. In another embodiment, the unit dose of iboga alkaloid is from about 0.01 mg to about 0.1 mg per day. The ranges include both extremes as well as any subranges there between. The ranges include both extremes as well as any subranges there between.

In another embodiment, the unit dose of iboga alkaloid is from about 0.1 mg to about 50 mg per day. In another embodiment, the unit dose of iboga alkaloid is from about 0.1 mg to about 30 mg per day. In another embodiment, the unit dose of iboga alkaloid is from about 0.1 mg to about 20 mg per day. In another embodiment, the unit dose of iboga alkaloid is from about 0.1 mg to about 10 mg per day. In another embodiment, the unit dose of iboga alkaloid is from about 0.1 mg to about 5 mg per day. In another embodiment, the unit dose of iboga alkaloid is from about 0.1 mg to about 1 mg per day. The ranges include both extremes as well as any subranges there between. The ranges include both extremes as well as any subranges there between.

In another embodiment, the unit dose of iboga alkaloid is from about 1 mg to about 50 mg per day. In another embodiment, the unit dose of iboga alkaloid is from about 1 mg to about 30 mg per day. In another embodiment, the unit dose of iboga alkaloid is from about 1 mg to about 20 mg per day. In another embodiment, the unit dose of iboga alkaloid is from about 1 mg to about 10 mg per day. In another embodiment, the unit dose of iboga alkaloid is from about 1 mg to about 5 mg per day. The ranges include both extremes as well as any subranges there between. The ranges include both extremes as well as any subranges there between.

In one embodiment, the unit dose of iboga alkaloid is from about 5 mg to about 50 mg per day. In a preferred embodiment, the unit dose of iboga alkaloid is from about 5 mg to about 30 mg per day. In another embodiment, the unit dose of iboga alkaloid is from about 5 mg to about 20 mg per day. In another embodiment, the unit dose of iboga alkaloid is from about 10 mg to about 50 mg per day. In another embodiment, the unit dose of iboga alkaloid is from about 10 mg to about 30 mg per day. In another embodiment, unit dose of iboga alkaloid is from about 10 mg to about 20 mg per day. The ranges include both extremes as well as any subranges there between.

In one embodiment, the unit dose of iboga alkaloid is about 0.001 mg per day. In one embodiment, the unit dose of iboga alkaloid is about 0.01 mg per day. In one embodiment, the unit dose of iboga alkaloid is about 0.1 mg per day. In one embodiment, the unit dose of iboga alkaloid is about 1 mg per day. In some embodiments, the unit dose of iboga alkaloid or pharmaceutically acceptable salt or solvate thereof is from about 5 mg to about 80 mg. In one embodiment, the unit dose of iboga alkaloid or pharmaceutically acceptable salt or solvate thereof is from about 10 mg to about 80 mg. In one embodiment, the unit dose of iboga alkaloid or pharmaceutically acceptable salt or solvate thereof is from about 20 mg to about 80 mg. In one embodiment, the unit dose of iboga alkaloid or pharmaceutically acceptable salt or solvate thereof is from about 30 mg to about 80 mg. In one embodiment, the unit dose of iboga alkaloid or pharmaceutically acceptable salt or solvate thereof is from about 40 mg to about 80 mg. In one embodiment, the unit dose of iboga alkaloid or pharmaceutically acceptable salt or solvate thereof is from about 50 mg to about 80 mg. In one embodiment, the unit dose of iboga alkaloid or pharmaceutically acceptable salt or solvate thereof is from about 60 mg to about 80 mg. In one embodiment, the unit dose of iboga alkaloid or pharmaceutically acceptable salt or solvate thereof is from about 70 mg to about 80 mg.

In some embodiments, the unit dose of iboga alkaloid or pharmaceutically acceptable salt or solvate thereof is from about 5 mg to about 50 mg. In one embodiment, the unit dose of iboga alkaloid or pharmaceutically acceptable salt or solvate thereof is from about 10 mg to about 50 mg. In one embodiment, the unit dose of iboga alkaloid or pharmaceutically acceptable salt or solvate thereof is from about 20 mg to about 50 mg. In one embodiment, the unit dose of iboga alkaloid or pharmaceutically acceptable salt or solvate thereof is from about 30 mg to about 50 mg. In one embodiment, the unit dose of iboga alkaloid or pharmaceutically acceptable salt or solvate thereof is from about 40 mg to about 50 mg. In one embodiment, the unit dose of iboga alkaloid or pharmaceutically acceptable salt or solvate thereof is from about 10 mg to about 40 mg. In one embodiment, the unit dose of iboga alkaloid or pharmaceutically acceptable salt or solvate thereof is from about 10 mg to about 30 mg. In one embodiment, the unit dose of iboga alkaloid or pharmaceutically acceptable salt or solvate thereof is from about 10 mg to about 20 mg.

In one embodiment, the unit dose is about 5 mg. In one embodiment, the unit dose is about 10 mg. In one embodiment, the unit dose is about 12.5 mg. In one embodiment, the unit dose is about 15 mg. In one embodiment, the unit dose is about 20 mg. In one embodiment, the unit dose is about 25 mg. In one embodiment, the unit dose is about 30 mg. In one embodiment, the unit dose is about 35 mg. In one embodiment, the unit dose is about 40 mg. In one embodiment, the unit dose is about 45 mg. In one embodiment, the unit dose is about 50 mg. In one embodiment, the unit dose is about 60 mg. In one embodiment, the unit dose is about 70 mg. In one embodiment, the unit dose is about 80 mg.

In some embodiments, the unit dose form comprises one or multiple dosages of iboga alkaloid and/or opioid analgesic to be administered periodically, such as once, twice, three time, four times or five time daily with iboga alkaloid or pharmaceutically acceptable salt and/or solvate thereof. In some embodiments, the administration is once daily, or once every second day, once every third day, three times a week, twice a week, or once a week. The dosage and frequency of the administration of the iboga alkaloid and/or opioid analgesic depends on criteria including the route of administration, content of composition, age and body weight of the patient, condition of the patient, sex of the patient, without limitation, as well as by the opioid analgesic employed. Determination of the unit dose form providing a dosage and frequency suitable for a given patient can readily be made by a qualified clinician.

These dose ranges may be achieved by transdermal, oral, or parenteral administration of iboga alkaloid or a pharmaceutically acceptable salt and/or solvate thereof in unit dose form. Such unit dose form may conveniently be provided in transdermal patch, tablet, caplet, liquid or capsule form. In certain embodiments, the iboga alkaloid is provided as iboga alkaloid HCl, with dosages reported as the amount of free base iboga alkaloid. In some embodiments, iboga alkaloid is provided in saline for intravenous administration.

Formulations

This invention further relates to pharmaceutically acceptable formulations comprising a unit dose of iboga alkaloid or pharmaceutically acceptable salt and/or solvate thereof, and optionally an opioid analgesic, wherein the unit dose of iboga alkaloid is an amount to potentiate the opioid while maintaining an acceptable QT interval prolongation.

In one embodiment, the pharmaceutical formulation comprises (a) at least one opioid analgesic, (b) an effective amount of iboga alkaloid or pharmaceutically acceptable salt and/or solvate thereof to potentiate the analgesic effect of the opioid, and (c) optionally a pharmaceutically acceptable carrier. The effective amount of iboga alkaloid is such to potentiate the opioid while maintaining an acceptable QT interval prolongation In one embodiment, the pharmaceutical formulation comprises an opioid and an amount of iboga alkaloid so as to render the amount of opioid sufficient to provide analgesia (pain relief) to a patient when administered thereto. In one embodiment, the amount of iboga alkaloid is sufficient to increase the analgesic effect of the amount of opioid in a patient when administered thereto.

In one embodiment, the pharmaceutical formulation comprises an opioid and an effective amount of iboga alkaloid so as to reduce tolerance or the onset of tolerance to the opioid in a patient when administered thereto. In one embodiment, the pharmaceutical formulation comprises an opioid and an effective amount of iboga alkaloid so as to reduce dependence or the onset of dependence on the opioid in a patient when administered thereto.

In some embodiments, the pharmaceutical formulation comprises iboga alkaloid and opioid analgesic at a ratio between about 100:1 and about 1:100. In one embodiment, the iboga alkaloid to opioid ratio is between about 100:1 and about 1:90. In one embodiment, the iboga alkaloid to opioid ratio is between about 100:1 and about 1:80. In one embodiment, the iboga alkaloid to opioid ratio is between about 100:1 and about 1:70. In one embodiment, the iboga alkaloid to opioid ratio is between about 100:1 and about 1:60. In one embodiment, the iboga alkaloid to opioid ratio is between about 100:1 and about 1:50. In one embodiment, the iboga alkaloid to opioid ratio is between about 100:1 and about 1:40. In one embodiment, the iboga alkaloid to opioid ratio is between about 100:1 and about 1:30. In one embodiment, the iboga alkaloid to opioid ratio is between about 100:1 and about 1:10. In one embodiment, the iboga alkaloid to opioid ratio is between about 100:1 and about 1:1. In one embodiment, the iboga alkaloid to opioid ratio is between about 10:1 and about 1:100. In one embodiment, the iboga alkaloid to opioid ratio is between about 10:1 and about 1:90. In one embodiment, the iboga alkaloid to opioid ratio is between about 10:1 and about 1:80. In one embodiment, the iboga alkaloid to opioid ratio is between about 10:1 and about 1:70. In one embodiment, the iboga alkaloid to opioid ratio is between about 10:1 and about 1:60. In one embodiment, the iboga alkaloid to opioid ratio is between about 10:1 and about 1:50. In one embodiment, the iboga alkaloid to opioid ratio is between about 10:1 and about 1:40. In one embodiment, the iboga alkaloid to opioid ratio is between about 10:1 and about 1:30. In one embodiment, the iboga alkaloid to opioid ratio is between about 10:1 and about 1:20. In a preferred embodiment, the iboga alkaloid to opioid ratio is between about 10:1 and about 1:10. In one embodiment, the iboga alkaloid to opioid ratio is between about 10:1 and about 1:1. The ranges include extremes as well as any subranges.

The pharmaceutical formulation may include opioid analgesic at any amount. For example, in some embodiments, the pharmaceutical formulation comprises about 1 mg to about 250 mg opioid analgesic. Preferably, the pharmaceutical formulation comprises about 5 mg to about 250 mg opioid analgesic. As would be understood by one skilled in the art, the amount of opioid analgesic in the pharmaceutical formulation is dependent on the type of opioid analgesic, as well as other considerations (e.g., weight of patient, age, tolerance to or dependence on an opioid, degree of pain, and the like).

In one embodiment, the pharmaceutical formulation comprises iboga alkaloid at from about 0.001 mg to about 50 mg. In a preferred embodiment, the pharmaceutical formulation comprises iboga alkaloid at from about 0.001 mg to about 30 mg. In another embodiment, the pharmaceutical formulation comprises iboga alkaloid at from about 0.001 mg to about 20 mg. In another embodiment, the pharmaceutical formulation comprises iboga alkaloid at from about 0.001 mg to about 10 mg. In another embodiment, the pharmaceutical formulation comprises iboga alkaloid at from about 0.001 mg to about 5 mg. In another embodiment, the pharmaceutical formulation comprises iboga alkaloid at from about 0.001 mg to about 1 mg. In another embodiment, the pharmaceutical formulation comprises iboga alkaloid at from about 0.001 mg to about 0.1 mg. In another embodiment, the pharmaceutical formulation comprises iboga alkaloid at from about 0.001 mg to about 0.01 mg. The ranges include both extremes as well as any subranges there between.

In another embodiment, the pharmaceutical formulation comprises iboga alkaloid at from about 0.01 mg to about 50 mg. In another embodiment, the pharmaceutical formulation comprises iboga alkaloid at from about 0.01 mg to about 30 mg. In another embodiment, the pharmaceutical formulation comprises iboga alkaloid at from about 0.01 mg to about 20 mg. In another embodiment, the pharmaceutical formulation comprises iboga alkaloid at from about 0.01 mg to about 10 mg. In another embodiment, the pharmaceutical formulation comprises iboga alkaloid at from about 0.01 mg to about 5 mg. In another embodiment, the pharmaceutical formulation comprises iboga alkaloid at from about 0.01 mg to about 1 mg. In another embodiment, the pharmaceutical formulation comprises iboga alkaloid at from about 0.01 mg to about 0.1 mg. The ranges include both extremes as well as any subranges there between. The ranges include both extremes as well as any subranges there between.

In another embodiment, the pharmaceutical formulation comprises iboga alkaloid at from about 0.1 mg to about 50 mg. In another embodiment, the pharmaceutical formulation comprises iboga alkaloid at from about 0.1 mg to about 30 mg. In another embodiment, the pharmaceutical formulation comprises iboga alkaloid at from about 0.1 mg to about 20 mg. In another embodiment, the pharmaceutical formulation comprises iboga alkaloid at from about 0.1 mg to about 10 mg. In another embodiment, the pharmaceutical formulation comprises iboga alkaloid at from about 0.1 mg to about 5 mg. In another embodiment, the pharmaceutical formulation comprises iboga alkaloid at from about 0.1 mg to about 1 mg. The ranges include both extremes as well as any subranges there between. The ranges include both extremes as well as any subranges there between.

In another embodiment, the pharmaceutical formulation comprises iboga alkaloid at from about 1 mg to about 50 mg. In another embodiment, the pharmaceutical formulation comprises iboga alkaloid at from about 1 mg to about 30 mg. In another embodiment, the pharmaceutical formulation comprises iboga alkaloid at from about 1 mg to about 20 mg. In another embodiment, the pharmaceutical formulation comprises iboga alkaloid at from about 1 mg to about 10 mg. In another embodiment, the pharmaceutical formulation comprises iboga alkaloid at from about 1 mg to about 5 mg. The ranges include both extremes as well as any subranges there between. The ranges include both extremes as well as any subranges there between.

In one embodiment, the pharmaceutical formulation comprises iboga alkaloid from about 5 mg to about 50 mg. In one embodiment, the pharmaceutical formulation comprises iboga alkaloid from about 5 mg to about 30 mg. In another embodiment, the pharmaceutical formulation comprises iboga alkaloid from about 5 mg to about 20 mg. In another embodiment, the pharmaceutical formulation comprises iboga alkaloid from about 10 mg to about 50 mg. In another embodiment, the pharmaceutical formulation comprises iboga alkaloid from about 10 mg to about 30 mg. In another embodiment, the pharmaceutical formulation comprises iboga alkaloid from about 10 mg to about 20 mg. The ranges include both extremes as well as any subranges there between.

In some embodiments, the unit dose of iboga alkaloid, with or without opioid analgesic, is administered in one or more dosings.

In some embodiments, the formulation is designed for periodic administration, such as once, twice, three time, four times or five time daily with iboga alkaloid or a pharmaceutically acceptable salt and/or solvate thereof, with or without an opioid analgesic. In some embodiments, the administration is once daily, or once every second day, once every third day, three times a week, twice a week, or once a week. The dosage and frequency of the administration depends on the route of administration, content of composition, age and body weight of the patient, condition of the patient, opioid analgesic(s) administered, without limitation. Determination of dosage and frequency suitable for the present technology can be readily made a qualified clinician.

In some embodiments, the formulation designed for administration in accordance with the methods provide herein can be suitable for a variety of delivery modes including, without limitation, oral and transdermal delivery. Formulations suitable for internal, pulmonary, rectal, nasal, vaginal, lingual, intravenous, intra-arterial, intramuscular, intraperitoneal, intracutaneous and subcutaneous routes may also be used. Possible formulations include tablets, capsules, pills, powders, aerosols, suppositories, parenterals, and oral liquids, including suspensions, solutions and emulsions. Sustained release dosage forms may also be used. All formulations may be prepared using methods that are standard in the art (see e.g., Remington's Pharmaceutical Sciences, 16th ed., A. Oslo editor, Easton Pa. 1980). In a preferred embodiment, the formulation is designed for oral administration, which may conveniently be provided in tablet, caplet, sublingual, liquid or capsule form.

Embodiments

The following embodiments are examples of methods and compositions as described herein. These embodiments are by way of example only, and are not intended to be limiting.

1. A method for potentiating the analgesic effect of an opioid analgesic in a patient undergoing or scheduled to undergo opioid analgesic therapy, the method comprising administering a potentiating amount of an iboga alkaloid or pharmaceutically acceptable salt and/or solvate thereof while maintaining aQT interval prolongation of less than about 60 milliseconds (ms) during said treatment, thereby potentiating the effect of the opioid.

2. The method of embodiment 1, wherein the potentiating amount of iboga alkaloid or pharmaceutically acceptable salt and/or solvate thereof is between about 5 mg and about 50 mg.

3. The method of embodiment 1 or 2, wherein a QT interval prolongation of less than about 30 ms is maintained during said treatment.

4. The method of any one of embodiments 1-3, further comprising administering iboga alkaloid or pharmaceutically acceptable salt and/or solvate thereof concurrently with the opioid.

5. The method of any one of embodiments 1-4, wherein the iboga alkaloid or pharmaceutically acceptable salt and/or solvate thereof is administered in a formulation that further comprises the opioid.

6. A method for preventing or reducing tolerance to an opioid analgesic in a patient undergoing or scheduled to undergo opioid analgesic therapy, the method comprising administering an effective amount of an iboga alkaloid or pharmaceutically acceptable salt and/or solvate thereof to prevent or reduce tolerance to the opioid while maintaining a QT interval prolongation of less than about 60 milliseconds (ms) during said treatment, thereby preventing or reducing tolerance to the opioid.

7. The method of embodiment 6, wherein the effective amount of iboga alkaloid or pharmaceutically acceptable salt and/or solvate thereof is between about 5 mg and about 50 mg.

8. The method of embodiment 6 or 7, wherein a QT interval prolongation of less than about 30 ms is maintained during said treatment.

9. The method of any one of embodiments 6-8, further comprising administering iboga alkaloid or pharmaceutically acceptable salt and/or solvate thereof concurrently with the opioid.

10. The method of any one of embodiments 6-9, wherein the iboga alkaloid or pharmaceutically acceptable salt and/or solvate thereof is administered in a formulation that further comprises the opioid analgesic.

11. The method of embodiment 9, wherein during concurrent administration, the dose of opioid analgesic is reduced by about 25% to about 75%, relative to the customary dose without iboga alkaloid administration.

12. A method for preventing dependence on an opioid analgesic in a patient undergoing or scheduled to undergo opioid analgesic therapy, the method comprising administering an effective amount of an iboga alkaloid or pharmaceutically acceptable salt and/or solvate thereof to prevent dependence on the opioid while maintaining a QT interval prolongation of less than about 60 milliseconds (ms) during said treatment, thereby preventing dependence on the opioid.

13. The method of embodiment 12, wherein the time to dependence on the opioid analgesic is increased.

14. The method of embodiment 12, wherein the dose of opioid analgesic at which dependence occurs is increased.

15. A method for preventing addiction to an opioid analgesic in a patient undergoing or scheduled to undergo opioid analgesic therapy, the method comprising administering an effective amount of an iboga alkaloid or pharmaceutically acceptable salt and/or solvate thereof to prevent addiction to the opioid while maintaining a QT interval prolongation of less than about 60 milliseconds (ms) during said treatment, thereby preventing addiction to the opioid.

16. The method of embodiment 15, wherein the time to addiction to the opioid analgesic is increased.

17. The method of embodiment 15, wherein the dose of opioid analgesic at which addiction occurs is increased.

18. The method of any one of embodiments 12-17, wherein the effective amount of iboga alkaloid or pharmaceutically acceptable salt and/or solvate thereof is between about 5 mg and about 50 mg.

19. The method of any one of embodiments 12-18, wherein a QT interval prolongation of less than about 30 ms is maintained during said treatment.

20. The method of any one of embodiments 12-19, further comprising administering iboga alkaloid or pharmaceutically acceptable salt and/or solvate thereof concurrently with the opioid.

21. The method of any one of embodiments 12-20, wherein the iboga alkaloid or pharmaceutically acceptable salt and/or solvate thereof is administered in a formulation that further comprises the opioid analgesic.

22. The method of embodiment 21, wherein during concurrent administration, the dose of opioid analgesic is reduced by about 25% to about 75%, relative to the customary dose without iboga alkaloid administration.

23. The method of any one of embodiments 1-22, wherein the iboga alkaloid is noribogaine, noribogaine derivative, or pharmaceutically acceptable salt and/or solvate thereof.

24. The method of any one of embodiments 1-22, wherein the iboga alkaloid is ibogaine, ibogaine derivative, or pharmaceutically acceptable salt and/or solvate thereof.

25. The method of any one of embodiments 1-24, wherein the opioid analgesic is selected from the group consisting of fentanyl, hydrocodone, hydromorphone, morphine, oxycodone, buprenorphine, codeine, thebaine, buprenorphine, methadone, meperidine, tramadol, tapentadol, levorphanol, sufentanil, pentazocine, and oxymorphone.

26. The method of embodiment 25, wherein the opioid analgesic is morphine.

27. The method of any one of embodiments 1-26, wherein the amount of iboga alkaloid administered to the patient is increased by about 5 mg to about 20 mg, between six and fourteen days after iboga alkaloid administration commences.

28. A pharmaceutical formulation comprising (a) at least one opioid analgesic, (b) an effective amount of iboga alkaloid or pharmaceutically acceptable salt and/or solvate thereof to potentiate the effect of the opioid as an analgesic, and (c) optionally a pharmaceutically acceptable carrier.

29. The pharmaceutical formulation of embodiment 28, wherein the effective amount of iboga alkaloid or pharmaceutically acceptable salt and/or solvate thereof is between about 5 mg and about 50 mg.

30. The pharmaceutical formulation of embodiment 28 or 29, wherein the opioid analgesic is selected from the group consisting of fentanyl, hydrocodone, hydromorphone, morphine, oxycodone, buprenorphine, codeine, thebaine, buprenorphine, methadone, meperidine, tramadol, tapentadol, levorphanol, sufentanil, pentazocine, and oxymorphone.

31. The pharmaceutical formulation of embodiment 30, wherein the opioid analgesic is morphine.

32. The pharmaceutical formulation of any one of embodiments 28-31, wherein the iboga alkaloid is noribogaine, noribogaine derivative, or pharmaceutically acceptable salt and/or solvate thereof.

33. The pharmaceutical formulation of any one of embodiments 28-31, wherein the iboga alkaloid is ibogaine, ibogaine derivative, or pharmaceutically acceptable salt and/or solvate thereof.

34. The method of any one of embodiments 1-27 or the pharmaceutical formulation of any one of embodiments 28-33, wherein the noribogaine derivative is represented by Formula I:

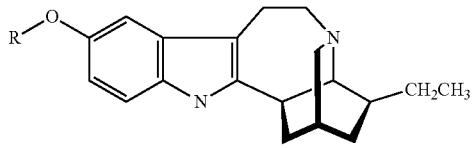

or a pharmaceutically acceptable salt thereof,
wherein R is hydrogen or a hydrolyzable group of the formula:

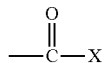

wherein X is an unsubstituted $C_1$-$C_{12}$ group or a $C_1$-$C_{12}$ group substituted by lower alkyl or lower alkoxy groups, wherein the noribogaine having the hydrolyzable group hydrolyzes in vivo to form 12-hydroxy ibogamine.

35. The method of any one of embodiments 1-27 or the pharmaceutical formulation of any one of embodiments 28-33, wherein the noribogaine derivative is represented by Formula II:

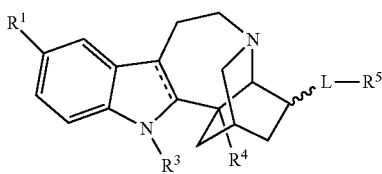

or a pharmaceutically acceptable salt thereof,
wherein
------ is a single or double bond;
$R^1$ is halo, $OR^2$, or $C_1$-$C_{12}$ alkyl optionally substituted with 1 to 5 $R^{10}$;
$R^2$ is hydrogen or a hydrolysable group selected from the group consisting of —C(O) $R^x$, —C(O)O$R^x$ and —C(O)N($R^y$)$_2$ where each $R^x$ is selected from the group consisting of $C_1$-$C_6$ alkyl optionally substituted with 1 to 5 $R^{10}$, and each $R^y$ is independently selected from the group consisting of hydrogen, $C_1$-$C_6$ alkyl optionally substituted with 1 to 5 $R^{10}$, $C_6$-$C_{14}$ aryl optionally substituted with 1 to 5 $R^{10}$, $C_3$-$C_{10}$ cycloalkyl optionally substituted with 1 to 5 $R^{10}$, $C_1$-$C_{10}$ heteroaryl having 1 to 4 heteroatoms and which is optionally substituted with 1 to 5 $R^{10}$, $C_1$-$C_{10}$ heterocyclic having 1 to 4 heteroatoms and which is optionally substituted with 1 to 5 $R^{10}$, and where each $R^y$, together with the nitrogen atom bound thereto form a $C_1$-$C_6$ heterocyclic having 1 to 4 heteroatoms and which is optionally substituted with 1 to 5 $R^{10}$ or a $C_1$-$C_6$ heteroaryl having 1 to 4 heteroatoms and which is optionally substituted with 1 to 5 $R^{10}$;
$R^3$ is selected from the group consisting of hydrogen, $C_1$-$C_{12}$ alkyl optionally substituted with 1 to 5 $R^{10}$, aryl optionally substituted with 1 to 5 $R^{10}$, —C(O)$R^6$, —C(O)N$R^6R^6$ and —C(O)O$R^6$;
$R^4$ is selected from the group consisting of hydrogen, —(CH$_2$)$_m$O$R^8$, —CR$^7$(OH)$R^8$, —(CH$_2$)$_m$CN, —(CH$_2$)$_m$CO$R^8$, —(CH$_2$)$_m$CO$_2R^8$, —(CH$_2$)$_m$C(O)NR$^7R^8$, —(CH$_2$)$_m$C(O)NR$^7NR^8R^8$, —(CH$_2$)$_m$C(O)NR$^7NR^8$C(O)$R^9$, and —(CH$_2$)$_m$NR$^7R^8$;
m is 0, 1, or 2;
L is a bond or $C_1$-$C_{12}$ alkylene;
$R^5$ is selected from the group consisting of hydrogen, $C_1$-$C_{12}$ alkyl substituted with 1 to 5 $R^{10}$, $C_1$-$C_{12}$ alkenyl substituted with 1 to 5 $R^{10}$, —$X^1$—$R^7$, —($X^1$—Y)$_n$—$X^1$—$R^7$, —SO$_2$NR$^7R^8$, —O—C(O)$R^9$, —C(O)O$R^8$, —C(O)NR$^7R^8$, —NR$^7R^8$, —NHC(O)$R^9$, and —NR$^7$C(O)$R^9$;
each $R^6$ is independently selected from the group consisting of hydrogen, $C_1$-$C_{12}$ alkyl, $C_2$-$C_{12}$ alkenyl, $C_2$-$C_{12}$ alkynyl, $C_6$-$C_{10}$ aryl, $C_1$-$C_6$ heteroaryl having 1 to 4 heteroatoms, and $C_1$-$C_6$ heterocycle having 1 to 4 heteroatoms, and wherein the alkyl, alkenyl, alkynyl, aryl, heteroaryl, and heterocycle are optionally substituted with 1 to 5 $R^{10}$;
$X^1$ is selected from the group consisting of O and S;
Y is $C_1$-$C_4$ alkylene or $C_6$-$C_{10}$ arylene, or a combination thereof;
n is 1, 2, or 3;
$R^7$ and $R^8$ are each independently selected from the group consisting of hydrogen, $C_1$-$C_{12}$ alkyl optionally substituted with 1 to 5 $R^{10}$, $C_1$-$C_6$ heterocycle having 1 to 4 heteroatoms and which is optionally substituted with 1 to 5 $R^{10}$, $C_3$-$C_{10}$ cycloalkyl optionally substituted with 1 to 5 $R^{10}$, $C_6$-$C_{10}$ aryl optionally substituted with 1 to 5 $R^{10}$ and $C_1$-$C_6$ heteroaryl having 1 to 4 heteroatoms optionally substituted with 1 to 5 $R^{10}$;
$R^9$ is selected from the group consisting of $C_1$-$C_{12}$ alkyl optionally substituted with 1 to 5 $R^{10}$, $C_1$-$C_6$ heterocycle having 1 to 4 heteroatoms optionally substituted with 1 to 5 $R^{10}$, $C_3$-$C_{10}$ cycloalkyl optionally substituted with 1 to 5 $R^{10}$, $C_6$-$C_{10}$ aryl optionally substituted with 1 to 5 $R^{10}$ and $C_1$-$C_6$ heteroaryl having 1 to 4 heteroatoms optionally substituted with 1 to 5 $R^{10}$;
$R^{10}$ is selected from the group consisting of $C_1$-$C_4$ alkyl, phenyl, halo, —OR$^{11}$, —CN, —COR$^{11}$, —CO$_2R^{11}$, —C(O)NHR$^{11}$, —NR$^{11}R^{11}$, —C(O)NR$^{11}R^{11}$, —C(O)NHN HR$^{11}$, —C(O)NR$^{11}$NHR$^{11}$, —C(O)NR$^{11}$NR$^{11}R^{11}$, —C(O)NHNR$^{11}$C(O)$R^{11}$, —C(O)NHNHC(O)$R^{11}$, —SO$_2$NR$^{11}R^{11}$, —C(O)NR$^{11}$NR$^{11}$C(O)$R^{11}$, and —C(O)NR$^{11}$NHC(O)$R^{11}$; and
$R^{11}$ is independently hydrogen or $C_1$-$C_{12}$ alkyl;
provided that:
when L is a bond, then $R^5$ is not hydrogen;
when ------ is a double bond, $R^1$ is an ester hydrolyzable group, $R^3$ and $R^4$ are both hydrogen, then -L-$R^5$ is not ethyl;
when ------ is a double bond, $R^1$ is —OH, halo or $C_1$-$C_{12}$ alkyl optionally substituted with 1 to 5 $R^{10}$, then $R^4$ is hydrogen; and
when ------ is a double bond, $R^1$ is $OR^2$, $R^4$ is hydrogen, -L-$R^5$ is ethyl, then $R^2$ is not a hydrolyzable group selected from the group consisting of an ester, amide, carbonate and carbamate.

36. The method of any one of embodiments 1-27 or the pharmaceutical formulation of any one of embodiments 28-33, wherein the noribogaine derivative is represented by Formula III:

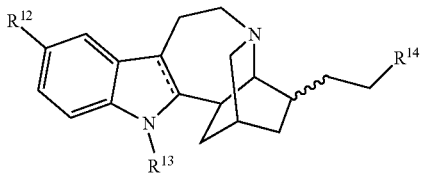

or a pharmaceutically acceptable salt thereof,
wherein
- - - - - - is a single or double bond;
$R^{12}$ is halo, —OH, —SH, —NH$_2$, —S(O)$_2$N(R$^{17}$)$_2$, —R$^z$-L$^1$-R$^{18}$, —R$^z$-L$^1$-R$^{19}$, —R$^z$-L$^1$-R$^{20}$ or —R$^z$-L$^1$-CHR$^{18}$R$^{19}$, where R$^z$ is O, S or NR$^{17}$;
$L^1$ is alkylene, arylene, —C(O)-alkylene, —C(O)-arylene, —C(O)O-arylene, —C(O)O-alkylene, —C(O)NR$^{20}$-alkylene, —C(O)NR$^{20}$-arylene, —C(NR$^{20}$)NR$^{20}$-alkylene or —C(NR$^{20}$)NR$^{20}$-arylene, wherein L$^1$ is configured such that —O-L$^1$-R$^{18}$ is —OC(O)-alkylene-R$^{18}$, —OC(O)O-arylene-R$^{18}$, —OC(O)O-alkylene-R$^{18}$, —OC(O)-arylene-R$^{18}$, —OC(O)NR$^{20}$-alkylene-R$^{18}$, —OC(O)NR$^{20}$-arylene-R$^{18}$, —OC(NR$^{20}$)NR$^{20}$-alkylene-R$^{18}$ or —OC(NR$^{20}$)NR$^{20}$-arylene-R$^{18}$, and wherein the alkylene and arylene are optionally substituted with 1 to 2 R$^{16}$;
$R^{13}$ is hydrogen, —S(O)$_2$OR$^{20}$, —S(O)$_2$R$^{20}$, —C(O)R$^{15}$, —C(O)NR$^{15}$R$^{15}$, —C(O)OR$^{15}$, C$_1$-C$_{12}$ alkyl optionally substituted with 1 to 5 R$^{16}$, C$_1$-C$_{12}$ alkenyl optionally substituted with 1 to 5 R$^{16}$, or aryl optionally substituted with 1 to 5 R$^{16}$;
$R^{14}$ is hydrogen, halo, —OR$^{17}$, —CN, C$_1$-C$_{12}$ alkyl, C$_1$-C$_{12}$ alkoxy, aryl or aryloxy, where the alkyl, alkoxy, aryl, and aryloxy are optionally substituted with 1 to 5 R$^{16}$;
each $R^{15}$ is independently selected from the group consisting of hydrogen, C$_1$-C$_{12}$ alkyl, C$_2$-C$_{12}$ alkenyl, C$_2$-C$_{12}$ alkynyl, aryl, heteroaryl, and heterocycle, and wherein the alkyl, alkenyl, alkynyl, aryl, heteroaryl, and heterocycle are optionally substituted with 1 to 5 R$^{16}$;
$R^{16}$ is selected from the group consisting of phenyl, halo, —OR$^{17}$, —CN, —COR$^{17}$, —CO$_2$R$^{17}$, —NR$^{17}$R$^{17}$, —NR$^{17}$C(O)R$^{17}$, —NR$^{17}$SO$_2$R$^{17}$, —C(O)NR$^{17}$R$^{17}$, —C(O)NR$^{17}$NR$^{17}$R$^{17}$, —SO$_2$NR$^{17}$R$^{17}$ and —C(O)NR$^{17}$NR$^{17}$C(O)R$^{17}$;
each $R^{17}$ is independently hydrogen or C$_1$-C$_{12}$ alkyl optionally substituted with from 1 to 3 halo;
$R^{18}$ is hydrogen, —C(O)R$^{20}$, —C(O)OR$^{20}$, —C(O)N(R$^{20}$)$_2$ or —N(R$^{20}$)C(O)R$^{20}$;
$R^{19}$ is hydrogen, —N(R$^{20}$)$_2$, —C(O)N(R$^{20}$)$_2$, —C(NR$^{20}$)N(R$^{20}$)$_2$, —C(NSO$_2$R$^{20}$)N(R$^{20}$)$_2$, —NR$^{20}$C(O)N(R$^{20}$)$_2$, —NR$^{20}$C(S)N(R$^{20}$)$_2$, —NR$^{20}$C(NR$^{20}$)N(R$^{20}$)$_2$, —NR$^{20}$C(NSO$_2$R$^{20}$)N(R$^{20}$)$_2$ or tetrazole; and
each $R^{20}$ is independently selected from the group consisting of hydrogen, C$_1$-C$_{12}$ alkyl and aryl;
provided that:
when - - - - - - is a double bond and R$^{13}$ and R$^{14}$ are hydrogen, then R$^{12}$ is not hydroxy;

when - - - - - - is a double bond, R$^{14}$ is hydrogen, R$^{12}$ is —O-L$^1$-R$^{18}$, —O-L$^1$-R$^{19}$, —O-L$^1$-R$^{20}$, and L$^1$ is alkylene, then —O-L$^1$-R$^{18}$, —O-L$^1$-R$^{19}$, —O-L$^1$-R$^{20}$ are not methoxy;

when - - - - - - is a double bond, R$^{14}$ is hydrogen, R$^z$ is O, L$^1$ is —C(O)-alkylene, —C(O)-arylene, —C(O)O-arylene, —C(O)O-alkylene, —C(O)NR$^{20}$-alkylene, or —C(O)NR$^{20}$-arylene, then none of R$^{18}$, R$^{19}$ or R$^{20}$ are hydrogen.

37. The method of any one of embodiments 1-27 or the pharmaceutical formulation of any one of embodiments 28-33, wherein the noribogaine derivative is represented by Formula IV:

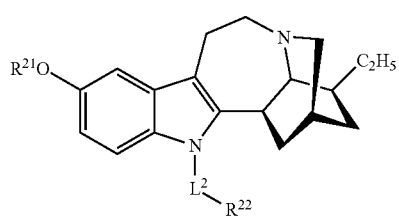

or a pharmaceutically acceptable salt thereof,
wherein
$R^{21}$ is selected from the group consisting of hydrogen, a hydrolysable group selected from the group consisting of —C(O)R$^{23}$, —C(O)NR$^{24}$R$^{25}$ and —C(O)OR$^{26}$, where R$^{23}$ is selected from the group consisting of hydrogen, alkyl, substituted alkyl, alkenyl, substituted alkenyl, alkynyl and substituted alkynyl, R$^{24}$ and R$^{25}$ are independently selected from the group consisting of hydrogen, alkyl, substituted alkyl, alkenyl, substituted alkenyl, alkynyl, substituted alkynyl, aryl, substituted aryl, heteroaryl, substituted heteroaryl, heterocyclic and substituted heterocyclic, R$^{26}$ is selected from the group consisting of alkyl, substituted alkyl, alkenyl, substituted alkenyl, alkynyl, substituted alkynyl, aryl, substituted aryl, heteroaryl, substituted heteroaryl, heterocyclic and substituted heterocyclic, provided that R$^{21}$ is not a saccharide or an oligosaccharide;

$L^2$ is selected from the group consisting of a covalent bond and a cleavable linker group;

$R^{22}$ is selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic, provided that R is not a saccharide or an oligosaccharide;

provided that when L$^2$ is a covalent bond and R$^{22}$ is hydrogen, then R$^{21}$ is selected from the group consisting of —C(O)NR$^{24}$R$^{25}$ and —C(O)OR$^{26}$; and further provided that when R$^{21}$ is hydrogen or —C(O)R$^{23}$ and L$^2$ is a covalent bond, then R$^{22}$ is not hydrogen.

38. The method of any one of embodiments 1-27 or the pharmaceutical formulation of any one of embodiments 28-33, wherein the noribogaine derivative is represented by Formula V:

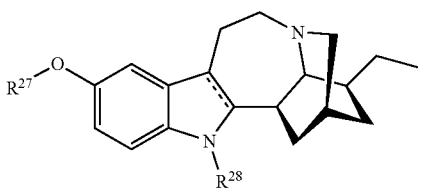

or a pharmaceutically acceptable salt thereof,
wherein:

⚌ refers to a single or a double bond provided that when ⚌ is a single bond, Formula V refers to the corresponding dihydro compound;
$R^{27}$ is hydrogen or $SO_2OR^{29}$;
$R^{28}$ is hydrogen or $SO_2OR^{29}$;
$R^{29}$ is hydrogen or $C_1$-$C_6$ alkyl;
provided that at least one of $R^{27}$ and $R^{28}$ is not hydrogen.

39. The method of any one of embodiments 1-27 or the pharmaceutical formulation of any one of embodiments 28-33, wherein the noribogaine derivative is represented by Formula VI:

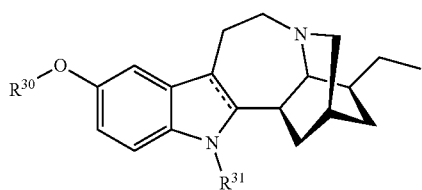

or a pharmaceutically acceptable salt thereof,
wherein:

⚌ refers to a single or a double bond provided that
when ⚌ is a single bond, Formula VI refers to the corresponding vicinal dihydro compound;
$R^{30}$ is hydrogen, a monophosphate, a diphosphate or a triphosphate; and
$R^{31}$ is hydrogen, a monophosphate, a diphosphate or a triphosphate;
provided that both $R^{30}$ and $R^{31}$ are not hydrogen;
wherein one or more of the monophosphate, diphosphate and triphosphate groups of $R^{30}$ and $R^{31}$ are optionally esterified with one or more $C_1$-$C_6$ alkyl esters.

40. The method of any one of embodiments 1-27 or the pharmaceutical formulation of any one of embodiments 28-33, wherein noribogaine or a pharmaceutically acceptable salt and/or solvate thereof is administered.

41. The method of any one of embodiments 1-27 or the pharmaceutical formulation of any one of embodiments 28-33, wherein the ibogaine derivative is represented by Formula VIII:

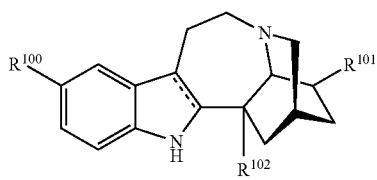

or a pharmaceutically acceptable salt and/or solvate thereof, wherein
$R^{100}$ is hydrogen or $C_1$-$C_3$ alkoxy;
$R^{101}$ is hydrogen, $C_1$-$C_3$ alkyl, $C_1$-$C_3$ alkoxy, $(CH_2)_mOC(O)$alkyl, $(CH_2)_mOH$, $(CH_2)_mOalkyl$, $(CH_2)_m O(CH_2)_p O(CH_2)_q O(CH_2)_r CH_3$ or $CH_2$—Y—$CH_3$ where each of m, p and q is 1, 2 or 3; and r is 0, 1 or 2, Y is O or NH; and
$R^{102}$ is H, $(CH_2)_nOH$, COOH, or $COOR^{104}$, where $R^{104}$ is $C_1$-$C_6$ alkyl or $(CH_2CH_2O)_nCH_3$, where n is 1, 2, or 3.

42. The method of any one of embodiments 1-27 or the pharmaceutical formulation of any one of embodiments 28-33, wherein the ibogaine derivative is selected from the group consisting of coronaridine, ibogamine, voacangine, 18-methoxycoronaridine, 2-Methoxyethyl-18-methoxycoronaridinate, and 18-Methylaminocoronaridine.

43. The method of any one of embodiments 1-27 or the pharmaceutical formulation of any one of embodiments 28-33, wherein the ibogaine derivative is selected from the group consisting of 16-hydroxymethyl-18-hydroxyibogaline, 16-hydroxymethyl-18-methoxyibogaline, 16-ethoxycarbonyl-18-hydroxyibogaline laurate, and 16-ethoxycarbonyl-18-hydroxyibogaline methoxyethoxymethyl ether.

44. The method of any one of embodiments 1-27 or the pharmaceutical formulation of any one of embodiments 28-33, wherein the ibogaine derivative is represented by Formula VIII:

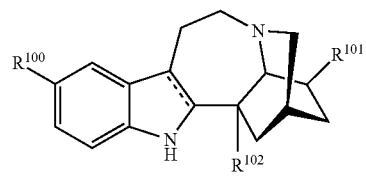

or a pharmaceutically acceptable salt and/or solvate thereof, wherein
$R^{100}$ is $OCH_3$;
$R^{101}$ is $CH_2CH_3$; and
$R^{102}$ is $COOR^{104}$, where $R^{104}$ is $(CH_2CH_2O)_nCH_3$, where n is 1.

45. The method of any one of embodiments 1-27 or the pharmaceutical formulation of any one of embodiments 28-33, wherein ibogaine or a pharmaceutically acceptable salt and/or solvate thereof is administered.

EXAMPLES

The following Examples are intended to further illustrate certain embodiments of the disclosure and are not intended to limit its scope. Further examples and details are provided in the Appendix filed herewith, which is incorporated by reference in its entirety as part of the specification.

Example 1. Pharmacokinetics and Pharmacodynamics of Noribogaine in Humans

Thirty-six healthy, drug-free male volunteers, aged between 18-55 years, were enrolled in and completed the study. This was an ascending single-dose, placebo-controlled, randomized double blind, parallel group study. Mean (SD) age was 22.0 (3.3) years, mean (SD) height was 1.82 (0.08) m, and mean (SD) weight was 78.0 (9.2) kg. Twenty-six subjects were Caucasian, 3 were Asian, 1 Maori, 1

Pacific Islander, and 5 Other. The protocol for this study was approved by the Lower South Regional Ethics Committee (LRS/12/06/015), and the study was registered with the Australian New Zealand Clinical Trial Registry (AC-TRN12612000821897). All subjects provided signed informed consent prior to enrolment, and were assessed as suitable to participate based on review of medical history, physical examination, safety laboratory tests, vital signs and ECG.

Within each dose level, 6 participants were randomized to receive noribogaine and 3 to receive placebo, based on a computer-generated random code. Dosing began with the lowest noribogaine dose, and subsequent cohorts received the next highest dose after the safety, tolerability, and blinded pharmacokinetics of the completed cohort were reviewed and dose-escalation approved by an independent Data Safety Monitoring Board. Blinded study drug was administered as a capsule with 240 ml of water after an overnight fast of at least 10 hours. Participants did not receive any food until at least 5 hours post-dose. Participants were confined to the study site from 12 hours prior to drug administration, until 72 hours post-dose, and there were subsequent outpatient assessments until 216 hours post-dose.

Blood was obtained for pharmacokinetic assessments pre-dose and then at 0.25, 0.5, 0.75, 1.0, 1.25, 1.5, 2, 2.5, 3, 3.5, 4, 4.5, 5, 5.5, 6, 7, 8, 10, 12, 14, 18, 24, 30, 36, 48, 60, 72, 96, 120, 168 and 216 hours post-dose. Samples were centrifuged and plasma stored at $-70°$ C. until analyzed. Block 24 hour urine collections were obtained following study drug administration for the 30 and 60 mg cohorts. Aliquots were frozen at $-20°$ C. until analyzed.

Pulse oximetry and capnography data were collected continuously using a GE Carescape B650 monitoring system from 2 hours prior to dosing and until six hours after dosing, and thereafter at 12, 24, 48 and 72 hours post-dosing. Additional oximetry data were collected at 120, 168 and 216 hours. Pupillary miosis was assessed by pupillometry. Dark-adapted pupil diameter was measured in triplicate using a Neuroptics PLR-200 pupillometer under standardized light intensity (<5 lux) pre-dose, and at 2, 4, 6, 12, 24, 48, 72, 96, 120, 168 and 216 hours post-dosing.

Plasma noribogaine concentrations were determined in the 3 mg and 10 mg dose groups using a validated, sensitive LCMSMS method. Sample preparation involved double extraction of basified plasma samples with tert-butyl methyl ether, drying the samples under a stream of nitrogen and reconstitution of sample with acetonitrile:B.P. water (5:95, v/v) containing 0.1% (v/v) formic acid. The compounds were separated by a 150×2.0 mm Luna 5 μm C18 column and detected with a triple-quadrupole API 4000 or 5000 mass spectrometer using electrospray ionization in positive mode and multiple reaction monitoring. Noribogaine-$d_4$ was used as the internal standard. The precursor-product ion transition values for noribogaine were m/z 297.6→122.3, and for the internal standard noribogaine-$d_4$ m/z 301.1→122.2. Analyst® software was used for data acquisition and processing. The ratio of the peak area of noribogaine to the internal standard noribogaine-$d_4$ was used for calibration and measurement of the unknown concentration of noribogaine. The lower limit of quantification (LLOQ) was 0.025 ng/ml noribogaine. The calibration curve was between 0.025 and 25.600 ng/ml noribogaine. Mobile phase A was acetonitrile:B.P. water (5:95, v/v) containing 0.1% (v/v) formic acid, and mobile phase B was acetonitrile:B.P. water (95:5, v/v) containing 0.1% (v/v) formic acid. Total run time was 6 minutes. Binary flow: Initial concentration was 8% mobile phase B; hold at 8% mobile phase B for 0.5 minutes and linear rise to 90% mobile phase B over 1.5 minutes; hold at 90% mobile phase B for 1 minute and then drop back to 8% mobile phase B over 0.01 minute. Equilibrate system for 3 minutes. Total run time was 6 minutes. Within- and between-day assay precision was <9%, and within- and between-day assay accuracy was <9%.

Plasma noribogaine concentrations were determined in the 30 mg and 60 mg dose groups using a validated, sensitive LCMSMS method. Sample preparation involved deproteinization of plasma samples with acetonitrile and dilution of sample with 0.1% (v/v) formic acid. The compounds were separated by a 150×2.0 mm Luna 5 μm C18 column and detected with a triple-quadrupole API 4000 or 5000 mass spectrometer using electrospray ionization in positive mode and multiple reaction monitoring. Noribogaine-$d_4$ was used as the internal standard. The precursor-product ion transition values for noribogaine were m/z 297.6→122.3, and for the internal standard noribogaine-$d_4$ m/z 301.1→122.2. Analyst® software was used for data acquisition and processing. The ratio of the peak area of noribogaine to the internal standard noribogaine-$d_4$ was used for calibration and measurement of the unknown concentration of noribogaine. The LLOQ was 0.50 ng/ml noribogaine. The calibration curve was between 0.50 and 256.00 ng/ml noribogaine. Mobile phase was the same as method A, and binary flow was also the same as method A. The within- and between-day assay precision was <9%, and the within- and between-day assay accuracy was <9%.

Plasma noribogaine glucuronide concentrations were determined in the 30 mg and 60 mg dose groups using a validated sensitive LCMSMS method. Sample preparation involved deproteinization of plasma samples with acetonitrile, drying the samples under a stream of nitrogen and reconstitution of sample with acetonitrile:B.P. water (5:95, v/v) containing 0.1% (v/v) formic acid. The compounds were separated by a 150×2.0 mm Luna 5 μm C18 column and detected with a triple-quadrupole API 4000 or 5000 mass spectrometer using electrospray ionization in positive mode and multiple reaction monitoring. Noribogaine-$d_4$ was used as the internal standard. The precursor-product ion transition values for noribogaine glucuronide were m/z 472.8→297.3, and for the internal standard noribogaine-$d_4$ m/z 301.1→122.2. Analyst® software was used for data acquisition and processing. The ratio of the peak area of noribogaine glucuronide to the internal standard noribogaine-$d_4$ was used for calibration and measurement of the unknown concentration of noribogaine glucuronide. The LLOQ was 0.050 ng/ml noribogaine glucuronide. The calibration curve was between 0.050 and 6.400 ng/ml noribogaine glucuronide. Mobile phases was the same as method A. Binary flow: Initial concentration was 6% mobile phase B; hold at 6% mobile phase B for 0.5 minutes and linear rise to 90% mobile phase B over 2 minutes; hold at 90% mobile phase B for 1 minute and then drop back to 6% mobile phase B over 0.01 minute. Equilibrate system for 3.5 minutes. Total run time was 7 minutes. The within- and between-day assay precision was <11%, and the within- and between-day assay accuracy was <10%.

Urine noribogaine and noribogaine glucuronide concentrations were determined in the 30 mg and 60 mg dose groups using a validated sensitive LCMSMS method. Sample preparation involved deproteinization of urine samples with acetonitrile and dilution of the sample with 0.1% (v/v) formic acid. The compounds were separated by a 150×2.0 mm Luna 5 μm C18 column and detected with a triple-quadrupole API 5000 mass spectrometer using electrospray ionization in positive mode and multiple reaction monitoring. Noribogaine-$d_4$ was used as the internal standard. The precursor-product ion transition values for noribogaine were m/z 297.6→122.3, noribogaine glucuronide m/z 472.8→297.3, and for the internal standard noribogaine-$d_4$ m/z 301.1→122.2. Analyst® software was used for data acquisition and processing. The ratios of the peak area of noribogaine and noribogaine glucuronide to the internal standard noribogaine-$d_4$ were used for calibration and measurement of the unknown concentration of noribogaine and its glucuronide. Assay LLOQ was 20.0 ng/ml for noribogaine and 2.0 ng/ml for noribogaine glucuronide. The calibration curve was between 20.0 and 5120.0 ng/ml noribogaine, and 2.0 and 512.0 ng/ml noribogaine glucuronide. Mobile phases were as described in method A, and binary flow as in method C. The within- and between-day assay precision was <13%, and within- and between-day assay accuracy was <12%.

Noribogaine and noribogaine glucuronide concentrations above the limit of quantification were used to calculate pharmacokinetic parameters using model-independent methods. The maximum plasma concentration (Cmax) and time to maximum plasma concentration (Tmax) were the observed values. Plasma concentration data in the post-distribution phase of the plasma concentration-time plot were fitted using linear regression to the formula ln C=ln Co−t·Kel, where Co was the zero-time intercept of the extrapolated terminal phase and Kel was the terminal elimination rate constant. The half-life ($t_{1/2}$) was determined using the formula $t_{1/2}$=0.693/Kel. The area under the concentration-time curve (AUC) from time zero to the last determined concentration-time point (tf) in the post distribution phase was calculated using the trapezoidal rule. The area under the curve from the last concentration-time point in the post distribution phase (Ctf) to time infinity was calculated from $AUC_{t-\infty}$=Ctf/Kel. The concentration used for Ctf was the last determined value above the LLOQ at the time point. The total $AUC_{0-\infty}$ was obtained by adding $AUC_{tf}$ and $AUC_{t-\infty}$. Noribogaine apparent clearance (CL/F) was determined using the formula CL/F=Dose/$AUC_{0-\infty}$×1000, and apparent volume of distribution (Vd/F) was determined using the formula Vd/F=(CL/F)/Kel. Total urine noribogaine was the sum of both analytes.

Summary statistics (means, standard deviations, and coefficients of variation) were determined for each dose group for safety laboratory test data, ECG and pharmacokinetic parameters, and pharmacodynamic variables. Categorical variables were analysed using counts and percentages. Dose-proportionality of AUC and Cmax was assessed using linear regression. The effect of dose on pharmacodynamic parameter values over time was assessed using two-factor analysis of variance (ANOVA). Pairwise comparisons (with Tukey-Kramer adjustment) between each dose group to the placebo were conducted at each time point using the least squares estimates obtained from the ANOVA, using SAS Proc Mixed (SAS ver 6.0).

Results

Pharmacokinetics: Mean plasma concentration-time plots of noribogaine are shown in FIG. 1, and mean pharmacokinetic parameters are shown in Table 1.

TABLE 1

|  | 3 mg (n = 6) (mean (SD)) | 10 mg (n = 6) (mean (SD)) | 30 mg (n = 6) (mean (SD)) | 60 mg (n = 6) (mean (SD)) |
| --- | --- | --- | --- | --- |
| Noribogaine | | | | |
| $AUC_{0-\infty}$ (ng · hr/ml) | 74.2 (13.1) | 254.5 (78.9) | 700.4 (223.3) | 1962.2 (726.5) |
| $AUC_{0-216}$ (ng · hr/ml) | 72.2 (13.2) | 251.4 (78.5) | 677.6 (221.1) | 1935.4 (725.4) |
| Cmax (ng/ml) | 5.2 (1.4) | 14.5 (2.1) | 55.9 (14.8) | 116.0 (22.5) |
| Tmax (hr) | 1.9 (0.6) | 2.9 (1.8) | 1.8 (0.6) | 2.4 (0.6) |
| $t_{1/2}$ (hr) | 40.9 (8.7) | 49.2 (11.5) | 27.6 (7.0) | 29.1 (9.3) |
| Vd/F (L) | 2485.1 (801.5) | 3085.8 (1197.0) | 1850.8 (707.9) | 1416.8 (670.1) |
| CL/F (L/h) | 41.4 (7.0) | 42.3 (12.0) | 46.9 (16.4) | 34.0 (11.4) |
| Noribogaine glucuronide | | | | |
| $AUC_{0-\infty}$ (ng · hr/ml) | — | — | 25.8 (9.3) | 67.1 (21.9) |
| $AUC_{0-216}$ (ng · hr/ml) | — | — | 25.7 (9.1) | 65.0 (21.5) |
| Cmax (ng/ml) | — | — | 1.8 (0.6) | 4.1 (1.2) |
| Tmax (hr) | — | — | 3.0 (0.6) | 3.8 (1.2) |
| $t_{1/2}$ (hr) | — | — | 20.6 (4.9) | 23.1 (3.0) |

Noribogaine was rapidly absorbed, with peak concentrations occurring 2-3 hours after oral dosing. Fluctuations in individual distribution-phase concentration-time profiles may suggest the possibility of enterohepatic recirculation (see highlighted individual 4-8 hour profiles in FIG. 1, insert). Both Cmax and AUC increased linearly with dose (Table 1, upper panel). Mean half-life estimates of 28-50 hours were observed across dose groups for noribogaine. Volume of distribution was extensive (1417-3086 L across dose groups).

Figure 2:
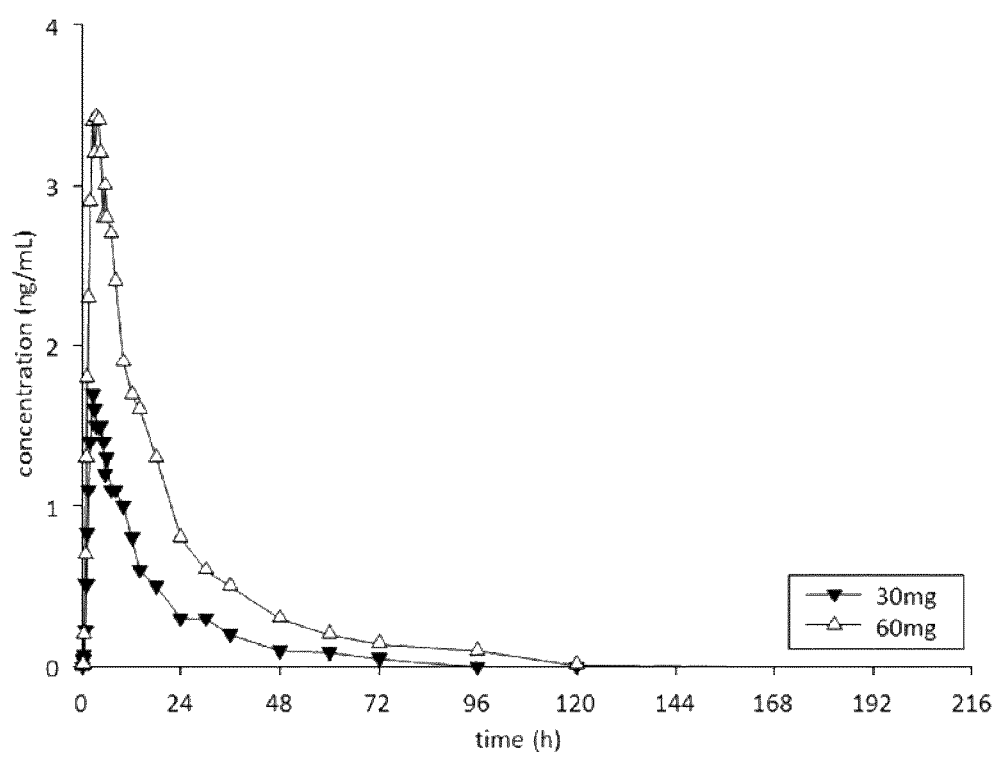
FIG. 2 represents mean plasma noribogaine glucuronide concentration-time profiles in healthy patients after single oral 30 mg (▼) or 60 mg (Δ) doses.

Mean plasma noribogaine glucuronide concentration-time plots for the 30 mg and 60 mg dose group are shown in FIG. 2, and mean pharmacokinetic parameters are shown in Table 1, lower panel. Noribogaine glucuronide was detected in all subjects by 0.75 hours, with peak concentrations occurring 3-4 hours after noribogaine dosing. Mean half-life of 21-23 hours was estimated for plasma noribogaine glucuronide. The proportion of noribogaine glucuronide Cmax and AUC relative to noribogaine was 3-4% for both dose groups. Total urine noribogaine elimination was 1.16 mg and 0.82 mg for the 30 mg and 60 mg dose groups respectively, representing 3.9% and 1.4% of the doses administered.

Pharmacodynamics: There was no evidence of pupillary constriction in subjects dosed with noribogaine. No between-dose group differences in pupil diameter were detected over time. After adjusting for baseline differences, comparison of each dose group with placebo by ANOVA showed no statistically significant differences (p>0.9).

Noribogaine treatment showed no analgesic effect in the cold pressor test. Analgesic effect was assessed based on duration of hand immersion in ice water and on visual analog scale (VAS) pain scores upon hand removal from the water bath. For duration of hand immersion, after adjusting for baseline differences, comparison of each dose group with placebo by ANOVA showed no statistically significant differences (p>0.9). Similarly, for VAS pain scores, after adjusting for baseline differences, comparison of each dose group with placebo by ANOVA showed no statistically significant differences (p=0.17).

Example 2. Safety and Tolerability of Noribogaine in Humans

Safety and tolerability of noribogaine were tested in the group of volunteers from Example 1. Cold pressor testing was conducted in 1° C. water according to the method of Mitchell et al. (*J Pain* 5:233-237, 2004) pre-dose, 6, 24, 48, 72 and 216 hours post-dosing. Safety evaluations included clinical monitoring, recording of adverse events (AEs), safety laboratory tests, vital signs, ECG telemetry from −2 h to 6 h after dosing, and 12-lead electrocardiograms (ECGs) up to 216 hours post-dosing.

Results

A total of thirteen adverse events were reported by seven participants (Table 2). Six adverse events were reported by three participants in the placebo group, five adverse events were reported by two subjects in the 3 mg dose group, and one adverse event was reported by single subjects in the 10 mg and 30 mg dose groups, respectively. The most common adverse events were headache (four reports) and epistaxis (two reports). All adverse events were of mild-moderate intensity, and all resolved prior to study completion. There were no changes in vital signs or safety laboratory tests of note. In particular, there were no changes in oximetry or capnography, or changes in respiratory rate. There were no QTcF values >500 msec at any time. One subject dosed with 10 mg noribogaine had a single increase in QTcF of >60 msec at 24 hours post-dosing.

TABLE 2

| Dose (mg) | Mild | Moderate | Severe |
|---|---|---|---|
| Placebo | Blepharitis<br>Bruising<br>Dry Skin<br>Eye pain, nonspecific<br>Infection at cannula site | Epistaxis | — |
| 3 | Back pain<br>Dizziness<br>Epistaxis<br>Headache | Headache | — |
| 10 | Headache | — | — |
| 30 | Headache | — | — |
| 60 | — | — | — |

Example 3. Safety, Tolerability, and Efficacy of Noribogaine in Opioid-Addicted Humans The efficacy of noribogaine in humans was evaluated in opioid-dependent participants in a randomized, placebo-controlled, double-blind trial. Patients had been receiving methadone treatment as the opioid substitution therapy, but were transferred to morphine treatment prior to noribogaine administration. This was done to avoid negative noribogaine-methadone interactions that are not observed between noribogaine and methadone. See U.S. Application Publication No. 2014/0288056, filed Mar. 14, 2014, and U.S. application Ser. No. 14/346,655, filed Mar. 21, 2014, which are incorporated herein by reference in their entireties.

Three cohorts of nine (9) subjects (6 administered noribogaine and 3 administered placebo in each cohort) were evaluated for tolerability, pharmacokinetics, and efficacy. Cohort 1 received a single dose of 60 mg noribogaine or placebo. Cohort 2 received a single dose of 120 mg noribogaine or placebo. Cohort 3 received a single dose of 180 mg noribogaine or placebo. Treatment was administered 2 hours after last morphine dose and the time to resumption of morphine (opioid substitution treatment, OST) was determined. Few adverse effects of noribogaine were observed in any of the participants, including no hallucinatory effects. Table 3 shows the reported adverse events for each treatment.

TABLE 3

Treatment Emergent Adverse Events Summary

| System Organ Class<br>Preferred Term | Placebo<br>(N = 9) | 60 mg<br>(N = 6) | 120 mg<br>(N = 6) | 180 mg<br>(N = 6) |
|---|---|---|---|---|
| Number of Subjects Reporting any AEs | 19:7 (77.8%) | 15:5 (83.3%) | 28:6 (100.0%) | 17:4 (66.7%) |
| Ear and Labyrinth Disorders | 0 | 0 | 2:2 (33.3%) | 0 |
| Tinnitus | 0 | 0 | 2:2 (33.3%) | 0 |
| Eye Disorders | 2:2 (22.2%) | 3:3 (50.0%) | 5:5 (83.3%) | 5:4 (66.7%) |
| Visual Impairment | 2:2 (22.2%) | 2:2 (33.3%) | 5:5 (83.3%) | 5:4 (66.7%) |
| Dry Eye | 0 | 1:1 (16.7%) | 0 | 0 |
| Gastrointestinal Disorders | 3:2 (22.2%) | 2:2 (33.3%) | 7:2 (33.3%) | 4:2 (33.3%) |
| Nausea | 1:1 (11.1%) | 0 | 3:2 (33.3%) | 2:2 (33.3%) |
| Diy Mouth | 0 | 0 | 1:1 (16.7%) | 1:1 (16.7%) |
| Vomiting | 0 | 0 | 2:1 (16.7%) | 1:1 (16.7%) |
| Diarrhoea | 1:1 (11.1%) | 0 | 1:1 (16.7%) | 0 |
| Dyspepsia | 1:1 (11.1%) | 2:2 (33.3%) | 0 | 0 |
| General Disorders and Administration Site Conditions | 4:3 (33.30%) | 0 | 2:2 (33.30%) | 1:1 (16.7%) |
| Catheter Site Related Reaction | 0 | 0 | 0 | 1:1 (16.7%) |
| Catheter Site Pain | 3:2 (22.2%) | 0 | 2:2 (33.3%) | 0 |
| Malaise | 1:1 (11.1%) | 0 | 0 | 0 |

TABLE 3-continued

Treatment Emergent Adverse Events Summary

| System Organ Class<br>Preferred Term | Placebo<br>(N = 9) | 60 mg<br>(N = 6) | 120 mg<br>(N = 6) | 180 mg<br>(N = 6) |
|---|---|---|---|---|
| Infections and Infestations | 1:1 (11.1%) | 0 | 1:1 (16.7%) | 2:2 (33.3%) |
| Cellulitis | 0 | 0 | 1:1 (16.7%) | 1:1 (16.7%) |
| Urinary Tract Infection | 0 | 0 | 0 | 1:1 (16.7%) |
| Catheter Site Infection | 1:1 (11.1%) | 0 | 0 | 0 |
| Musculoskeletal and Connective Tissue Disorders | 1:1 (11.1%) | 2:1 (16.7%) | 0 | 2:2 (33.30%) |
| Back Pain | 1:1 (11.1%) | 2:1 (16.7%) | 0 | 1:1 (16.7%) |
| Limb Discomfort | 0 | 0 | 0 | 1:1 (16.7%) |
| Nervous System Disorders | 7:5 (55.6%) | 7:4 (66.7%) | 5:4 (66.7%) | 3:2 (33.3%) |
| Headache | 6:5 (55.6%) | 7:4 (66.7%) | 2:2 (33.3%) | 3:2 (33.3%) |
| Hyperaesthesia | 0 | 0 | 1:1 (16.7%) | 0 |
| Pseudoparalysis | 0 | 0 | 1:1 (16.7%) | 0 |
| Tremor | 0 | 0 | 1:1 (16.7%) | 0 |
| Somnoience | 1:1 (11.1%) | 0 | 0 | 0 |
| Psychiatric Disorders | 1:1 (11.1%) | 1:1 (16.7%) | 0 | 0 |
| Depressed Mood | 0 | 1:1 (16.7%) | 0 | 0 |
| Euphoric Mood | 1:1 (11.1%) | 0 | 0 | 0 |
| Respiratory, Thoracic and Mediastinal Disorders | 0 | 0 | 4:2 (33.3%) | 0 |
| Epistaxis | 0 | 0 | 2:1 (16.7%) | 0 |
| Oropharyngeal Pain | 0 | 0 | 1:1 (16.7%) | 0 |
| Rhinorrhoea | 0 | 0 | 1:1 (16.7%) | 0 |
| Skin and Subcutaneous Tissue Disorders | 0 | 0 | 2:1 (16.7%) | 0 |
| Skin Discomfort | 0 | 0 | 1:1 (16.7%) | 0 |
| Skin Irritation | 0 | 0 | 1:1 (16.7%) | 0 |

Note:
Within each system organ class, Preferred Terms are presented by descending incidence of descending dosages groups and then the placebo group.
Note:
N = number of subjects in the safety population.

Figure 3:
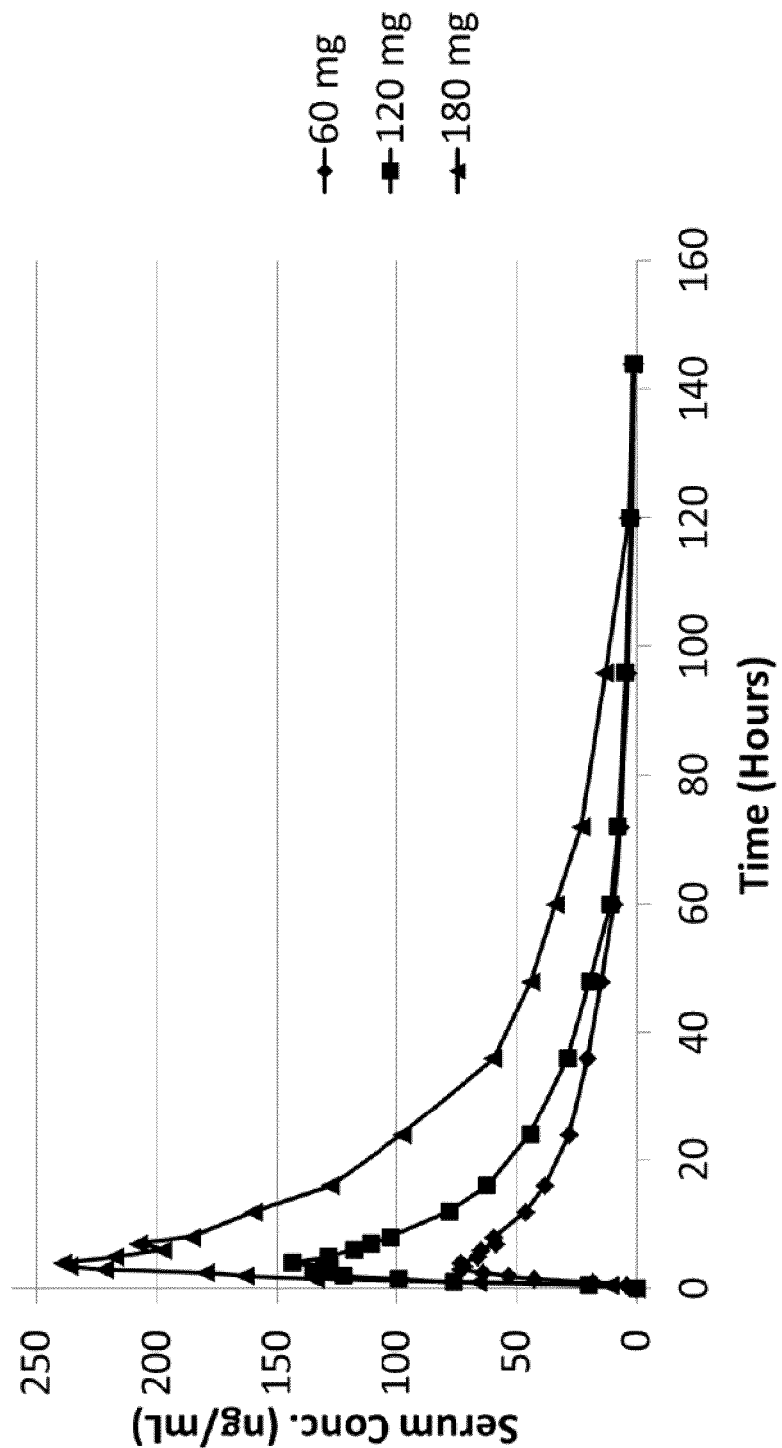
FIG. 3 illustrates the mean noribogaine concentration-time profile in opioid-addicted patients after a single oral 60 mg (♦), 120 mg (■), or 180 mg (▲) dose of noribogaine.

FIG. 3 indicates the average serum noribogaine concentration over time after administration of noribogaine for each cohort (60 mg, diamonds; 120 mg, squares; or 180 mg, triangles).

Results

Pharmacokinetic results for each cohort are given in Table 4. Maximum serum concentration of noribogaine (Cmax) increased in a dose-dependent manner. Time to Cmax (Tmax) was similar in all three cohorts. Mean half-life of serum noribogaine was similar to that observed in healthy patients.

TABLE 4

Pharmacokinetic results from the Patients in Phase IB Study

| PK parameter | Cohort 1 (60 mg)<br>Data (mean ± SD)<br>[range] | Cohort 2 (120 mg)<br>Data (mean ± SD)<br>[range] | Cohort 3 (180 mg)<br>Data (mean ± SD)<br>[range] |
|---|---|---|---|
| Cmax (ng/ml) | 81.64 ± 23.77<br>[41.29-113.21] | 172.79 ± 30.73<br>[138.84-229.55] | 267.88 ± 46.92<br>[204.85-338.21] |
| Tmax (hours) | 3.59 ± 0.92<br>[2.50-5.00] | 2.99 ± 1.23<br>[0.98-4.02] | 4.41 ± 1.80<br>[3.00-8.00] |
| $AUC_{(0-T)}$ (ng · hr/ml) | 2018.01 ± 613.91<br>[1094.46-2533.44] | 3226.38 ± 1544.26<br>[1559.37-5638.98] | 6523.28 ± 2909.80<br>[3716.69-10353.12] |
| $AUC_{(0-\gamma)}$ (ng · hr/ml) | 2060.31 ± 609.39<br>[1122.29-2551.63] | 3280.50 ± 1581.43<br>[1595.84-5768.52] | 6887.67 ± 3488.91<br>[3734.21-12280.91] |
| Half-life (hrs) | 29.32 ± 7.28<br>[18.26-37.33] | 30.45 ± 9.14<br>[21.85-48.33] | 23.94 ± 5.54<br>[19.32-34.90] |
| Vd/F | 1440.7 ± 854.0<br>[619.5-2772.5] | 2106.43 ± 1644.54<br>[824.24-5243.78] | 1032.19 ± 365.30<br>[581.18-1608.98] |
| Cl/F | 32.14 ± 12.38<br>[23.51-53.46] | 44.68 ± 21.40<br>[20.80-75.20] | 31.47 ± 13.12<br>[14.66-48.20] |

Figure 4:
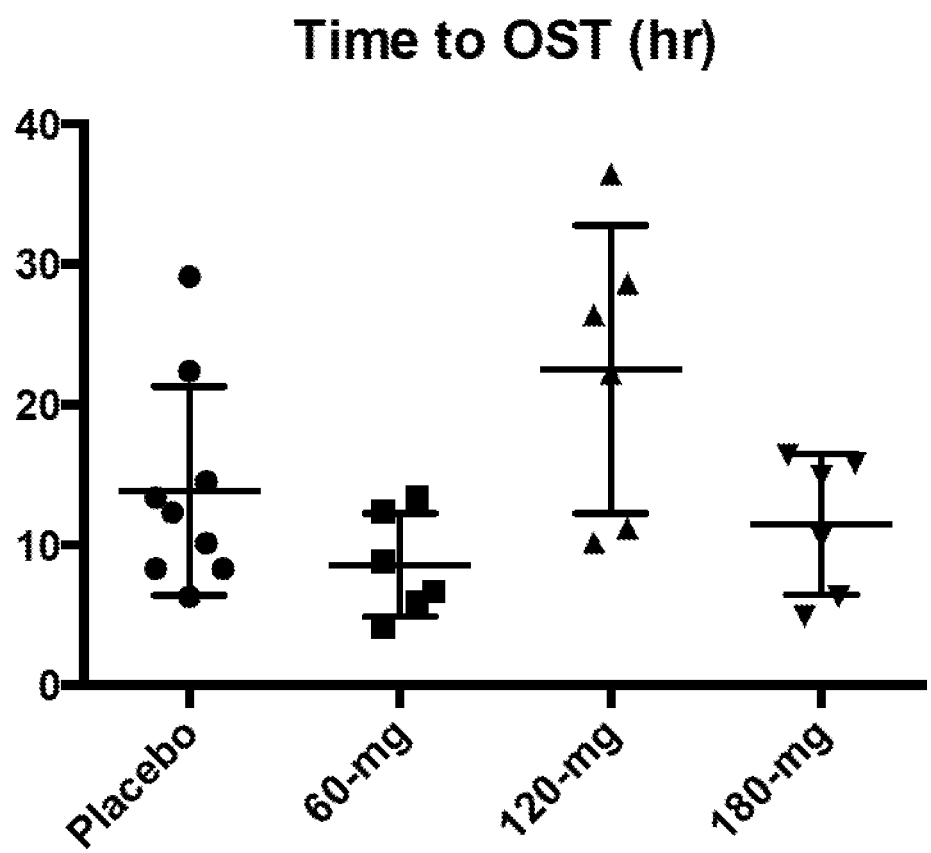
FIG. 4 illustrates hours to resumption of opioid substitution treatment (OST) for each patient given placebo (●), or a single oral dose of noribogaine (60 mg, ■; 120 mg, ▲; 180 mg, ▼). Center horizontal line represents mean. Error bars represent standard deviation.

FIG. 4 indicates the time to resumption of morphine (OST) for patients treated with placebo (circles), 60 mg noribogaine (squares), 120 mg noribogaine (triangles), and 180 mg noribogaine (inverted triangles). Patients receiving a single 120 mg dose of noribogaine exhibited an average time to resumption of opioids of greater than 20 hours. Patients receiving a single 180 mg dose of noribogaine exhibited an average time to resumption of opioids similar to that of placebo. This demonstrates that increasing the dose of noribogaine to 180 mg results in a shorter time to resumption of OST than observed in patients receiving 120 mg noribogaine. Time to resumption of OST after treatment with 180 mg was still longer than untreated patients (7 hours, not shown) or those administered 60 mg noribogaine.

Patients were evaluated based on the Clinical Opiate Withdrawal Scale (COWS), Subjective Opiate Withdrawal Scale (SOWS), and Objective Opiate Withdrawal Scale (OOWS) scoring systems over the period of time between administration of noribogaine (or placebo) until resumption of OST. These scales are outlined in Guidelines for the Psychosocially Assisted Pharmacological Treatment of Opioid Dependence, World Health Organization, Geneva (2009), Annex 10, which is incorporated herein by reference in its entirety. The scales measure the intensity of withdrawal symptoms, based on clinical, subjective, and objective indicia.

Figure 5:
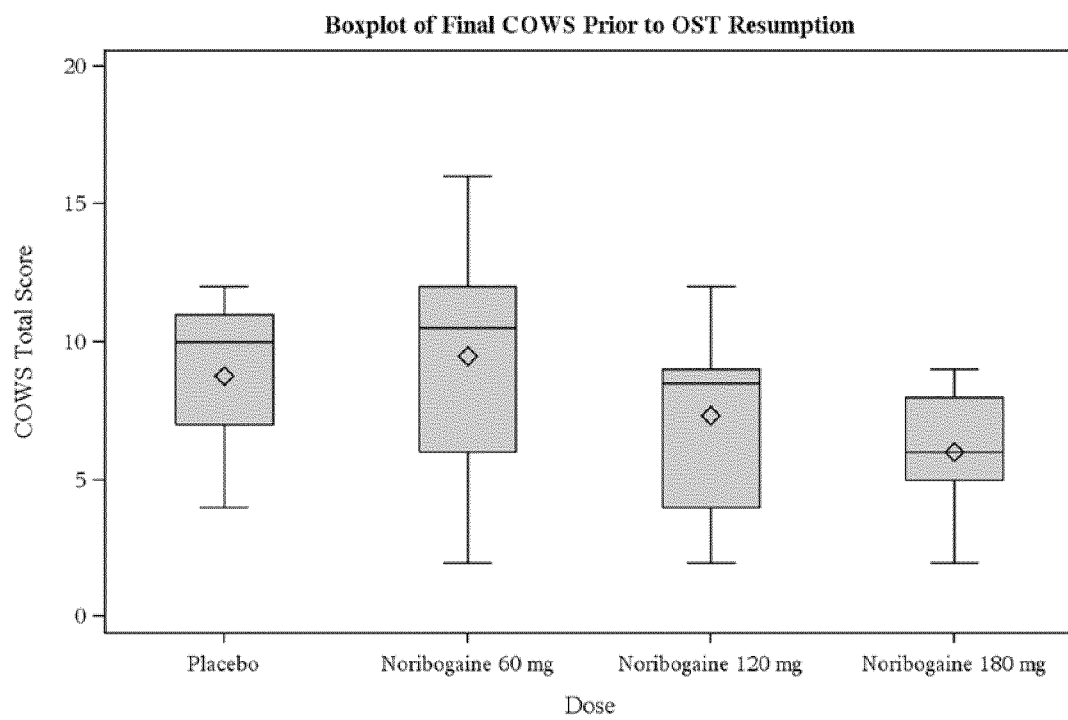
FIG. 5 illustrates results of noribogaine treatment on final COWS scores before resumption of OST. Boxes include values representing 25%-75% quartiles. Diamonds represent the median, crossbars represent mean. Whiskers represent values within one standard deviation of mid-quartiles. No outliers were present.

FIG. 5 shows the COWS scores at time of resumption of OST for each cohort. Box includes values representing 25%-75% quartiles. Diamond=median; crossbar in box=mean; whiskers=values within standard deviation of mid-quartiles. No outliers present. The highly variable COWS scores across and within each cohort indicates that patients were resuming opiates without relation to the intensity of withdrawal. This was also reflected in SOWS and OOWS scores at the time of resumption of OST.

Figure 6A:
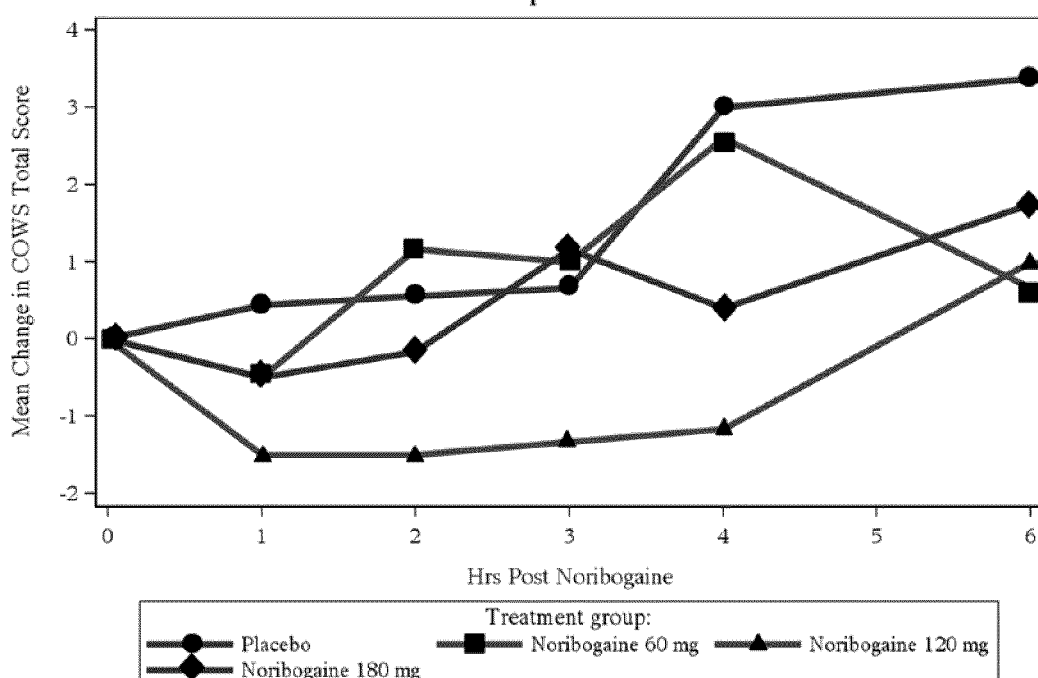
FIG. 6A illustrates of the mean change in total COWS scores over the first 6 hours following dosing of noribogaine (60 mg, ■: 120 mg, ▲; 180 mg, ♦) or placebo (●). Data is given relative to baseline COWS score.
Figure 6B:
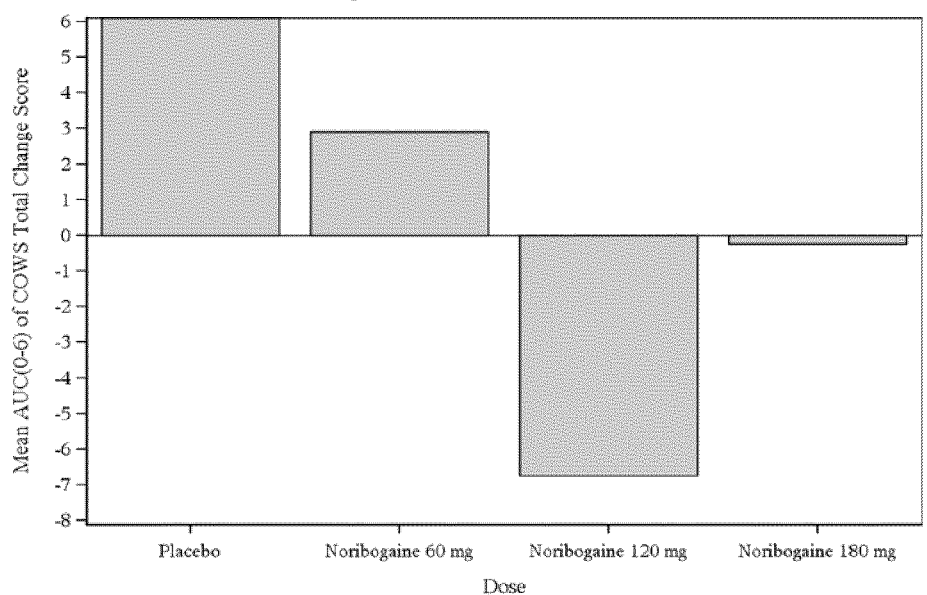
FIG. 6B illustrates the mean area under the curve (AUC) over the initial 6 hour period after administration of noribogaine or placebo, based on the COWS score data given in FIG. 6A. A negative change in score indicates that withdrawal symptoms subsided over the period.
Figure 7A:
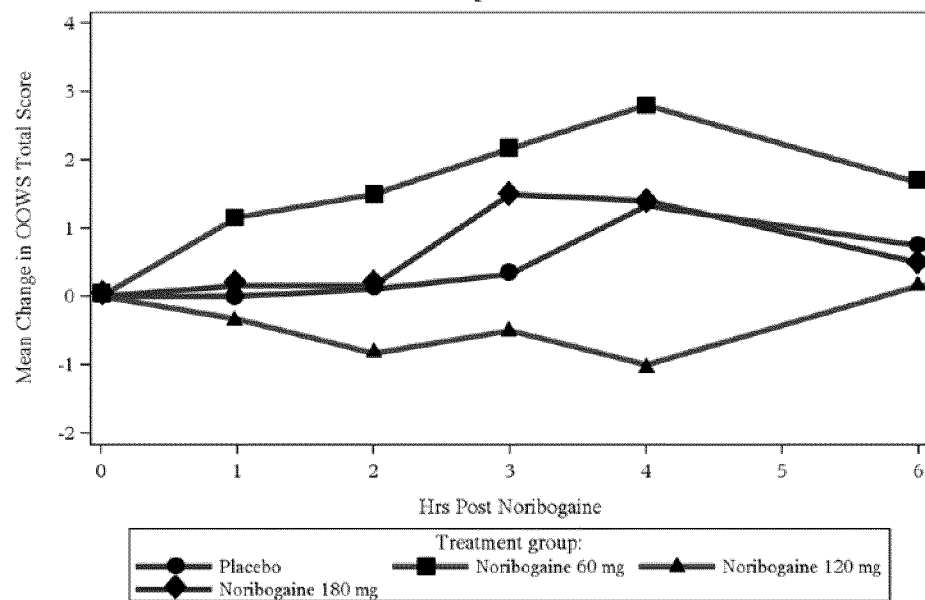
FIG. 7A illustrates of the mean change in total OOWS scores over the first 6 hours following dosing of noribogaine (60 mg ■, 120 mg, ▲: 180 mg. ♦) or placebo (●). Data is given relative to baseline OOWS score.
Figure 7B:
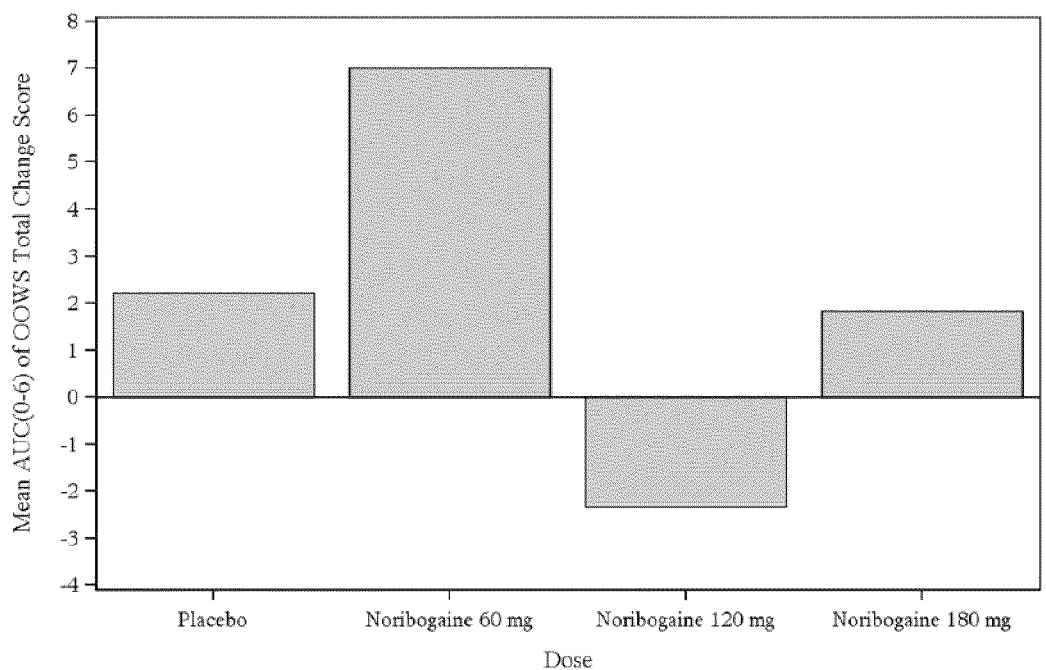
FIG. 7B illustrates the mean area under the curve (AUC) over the initial 6 hour period after administration of noribogaine or placebo, based on the OOWS score data given in FIG. 7A. A negative change in score indicates that withdrawal symptoms subsided over the period.
Figure 8A:
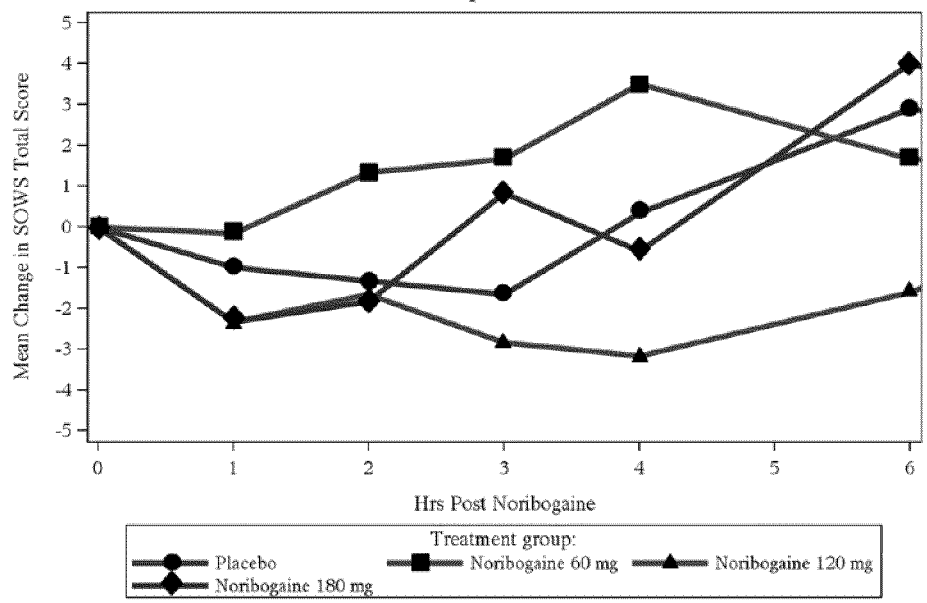
FIG. 8A illustrates of the mean change in total SOWS scores over the first 6 hours following dosing of noribogaine (60 mg, ■; 120 mg, ▲; 180 mg. ♦) or placebo (●). Data is given relative to baseline SOWS score.
Figure 8B:
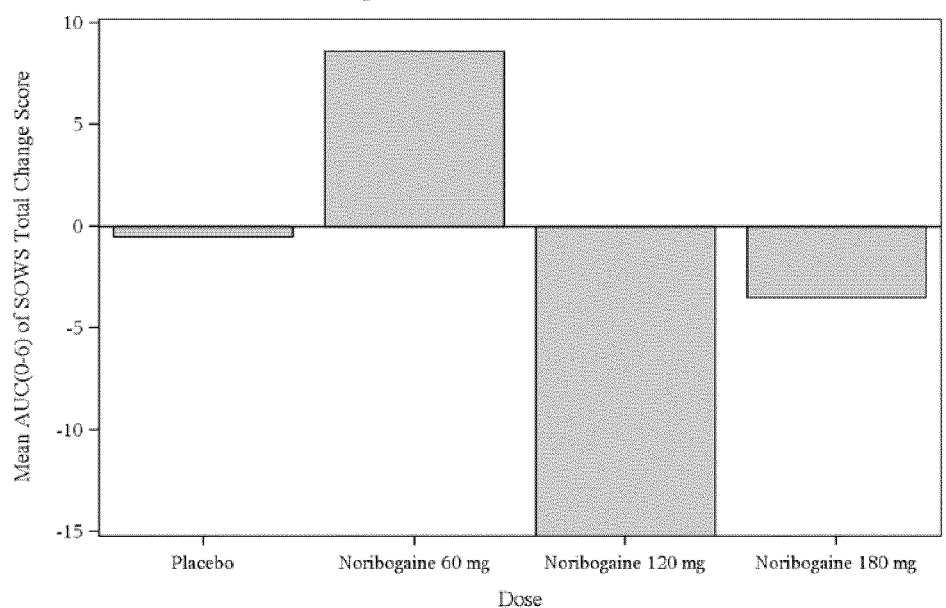
FIG. 8B illustrates the mean area under the curve (AUC) over the initial 6 hour period after administration of noribogaine or placebo, based on the SOWS score data given in FIG. 8A. A negative change in score indicates that withdrawal symptoms subsided over the period.

FIG. 6A shows the mean change in total COWS scores over the first six hours following dosing and prior to resumption of OST. FIG. 6B shows the mean AUC(0-6 hours) of the COWS total score change from baseline. FIG. 7A shows the mean change in total OOWS scores over the first six hours following dosing and prior to resumption of OST. FIG. 7B shows the mean AUC(0-6 hours) of the OOWS total score change from baseline. FIG. 8A shows the mean change in total SOWS scores over the first six hours following dosing and prior to resumption of OST. FIG. 8B shows the mean AUC(0-6 hours) of the SOWS total score change from baseline. These data indicate that withdrawal symptoms get worse over time after cessation of OST, and that patients administered placebo experience generally worse withdrawal symptoms over that period. Patients who received 120 mg noribogaine generally experienced fewer withdrawal symptoms than the other patients, regardless of the scale used. Patients administered placebo generally experienced more withdrawal symptoms than patients who were administered noribogaine.

Figure 9A:
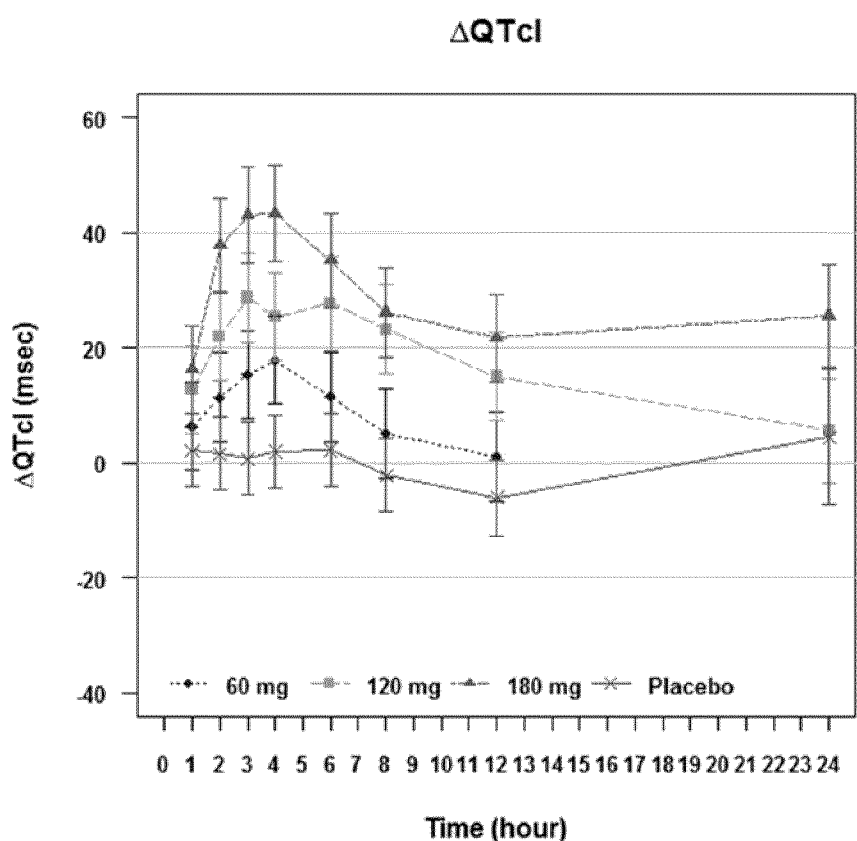
FIG. 9A illustrates the average change in QT interval ($\Delta$QTc1) for each cohort (60 mg, ■; 120 mg, ▲; 180 mg, ♦; or placebo, ●) over the first 24 hours post administration.
Figure 9B:
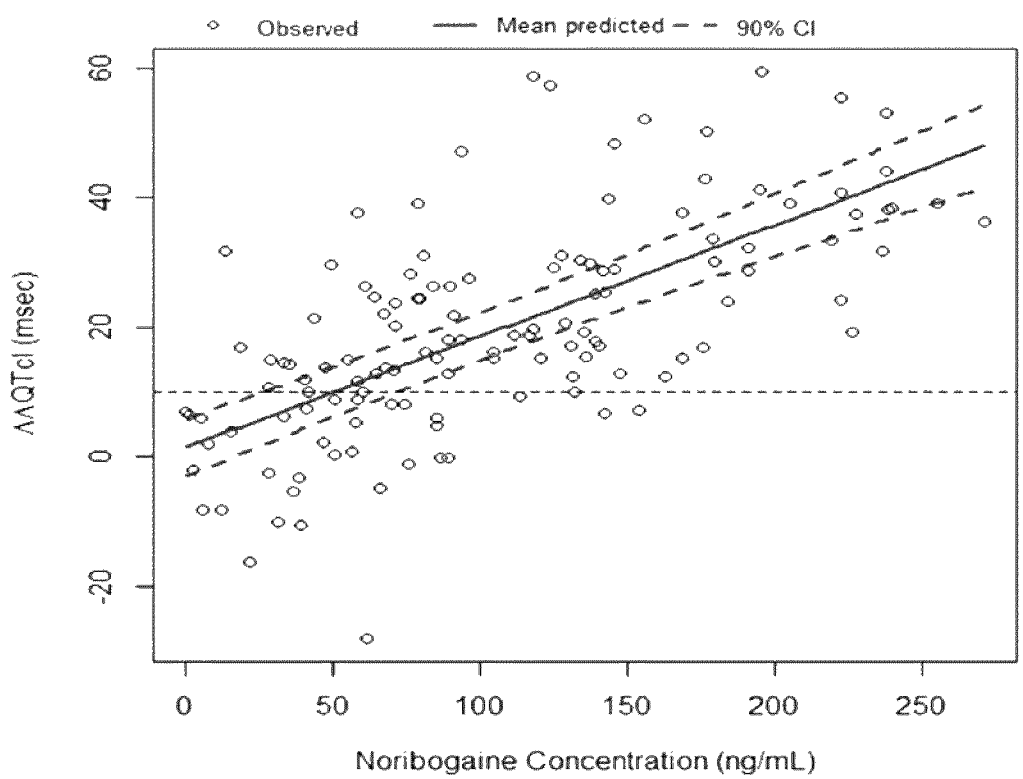
FIG. 9B illustrates the relationship between noribogaine concentrations and $\Delta\Delta$QTcI with 90% CI.
Figure 9C:
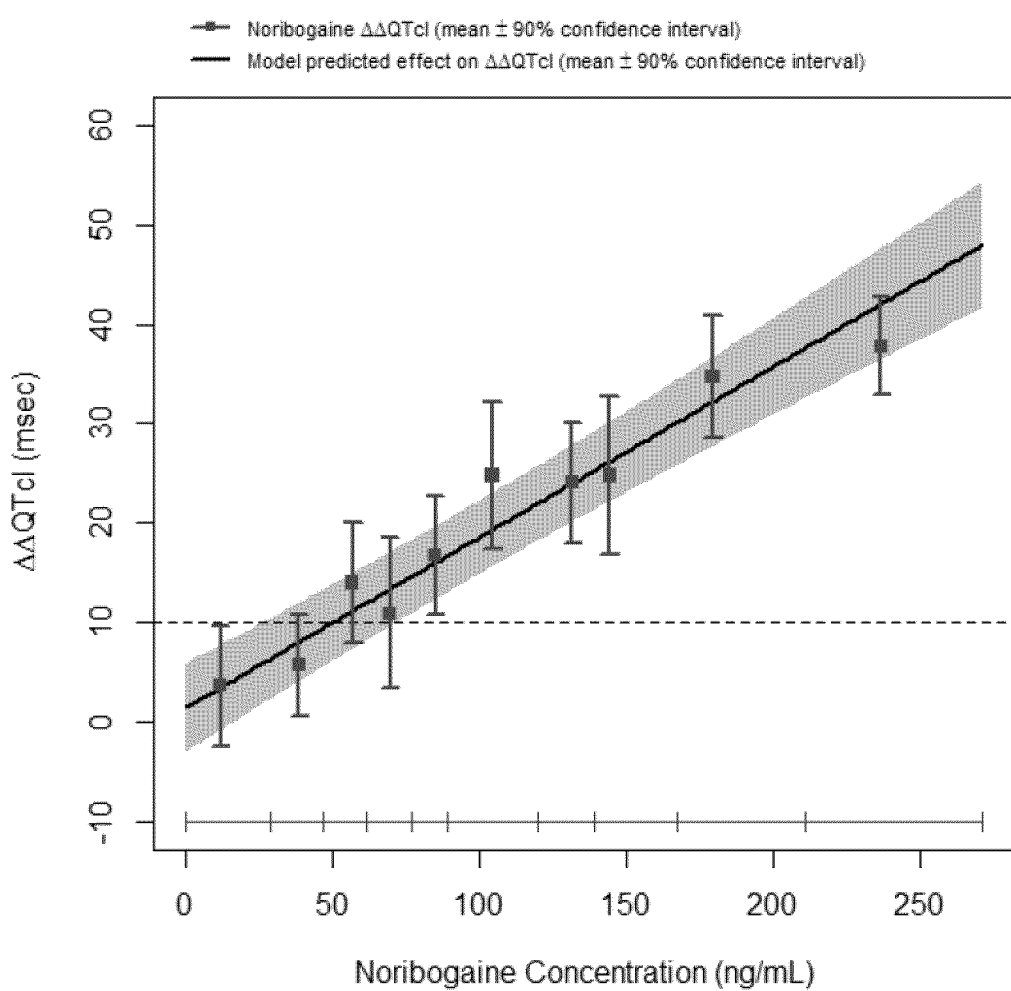
FIG. 9C is a goodness-of-fit plot for observed and predicted relation between noribogaine plasma levels.

Patients' QT intervals were evaluated at regular time points throughout the study. FIG. 9A shows the average change in QT interval ($\Delta$QTc1, i.e., QT interval prolongation) over the first 24 hours post noribogaine (or placebo) administration. FIG. 9B shows the relationship between noribogaine concentrations and $\Delta\Delta$QTc1 with 90% CI. There is a dose-dependent increase in QT interval prolongation that is correlated with the serum concentration of noribogaine. A goodness-of-fit plot for the observed and predicted relation between noribogaine plasma levels and $\Delta\Delta$QTc1 is provided in FIG. 9C.

Example 4. Efficacy of Noribogaine to Potentiate Opioid Analgesic Effect in Humans Case 1

Figure 10:
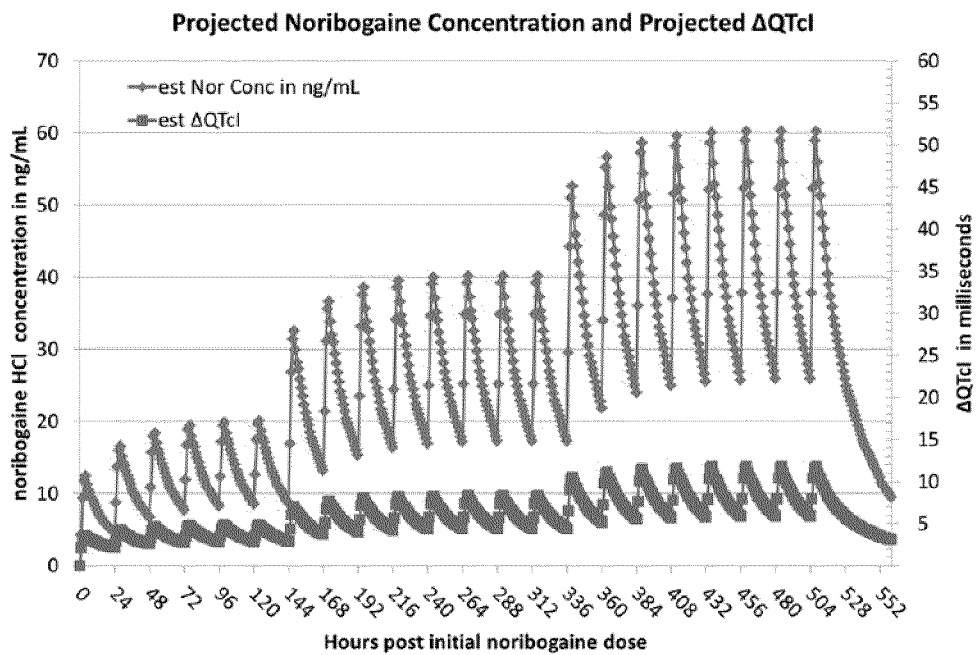
FIG. 10 illustrates the projected noribogaine serum concentration (♦) and projected QT prolongation ($\Delta$QTcI) (■) during the course of noribogaine treatment as described in Example 4, case 1.

A male patient, age 35, undergoing opioid analgesic therapy for chronic back pain, is treated with noribogaine hydrochloride at the doses indicated in Table 5, concurrently with the opioid. The amount of opioid analgesic administered to the patient is about half of the customary dose given in a similar situation without noribogaine co-treatment. The patient does not exhibit tolerance to or dependence on the opioid during the study period. Table 5 and FIG. 10 indicate the projected serum concentration and increase in QTc1 during the course of treatment. Data is estimated based on the human trial data provided in Examples 1-3.

TABLE 5

| Dose # | INPUT DOSE mg | Projected Mean Plasma Conc ng/mL pre-dose | Projected Mean QTcl Increase in msec pre-dose |
|---|---|---|---|
| 1 | 10 | 9 | 3 |
| 2 | 10 | 9 | 3 |
| 3 | 10 | 8 | 3 |
| 4 | 10 | 8 | 3 |
| 5 | 10 | 7 | 3 |
| 6 | 10 | 5 | 2 |
| 7 | 20 | 7 | 3 |
| 8 | 20 | 8 | 3 |
| 9 | 20 | 8 | 3 |
| 10 | 20 | 9 | 3 |
| 11 | 20 | 9 | 3 |
| 12 | 20 | 13 | 4 |
| 13 | 20 | 15 | 4 |
| 14 | 20 | 16 | 4 |
| 15 | 30 | 17 | 4 |
| 16 | 30 | 17 | 4 |
| 17 | 30 | 17 | 4 |
| 18 | 30 | 17 | 4 |
| 19 | 30 | 17 | 4 |
| 20 | 30 | 22 | 5 |
| 21 | 30 | 24 | 6 |
| 22 | 30 | 25 | 6 |

Case 2

Figure 11:
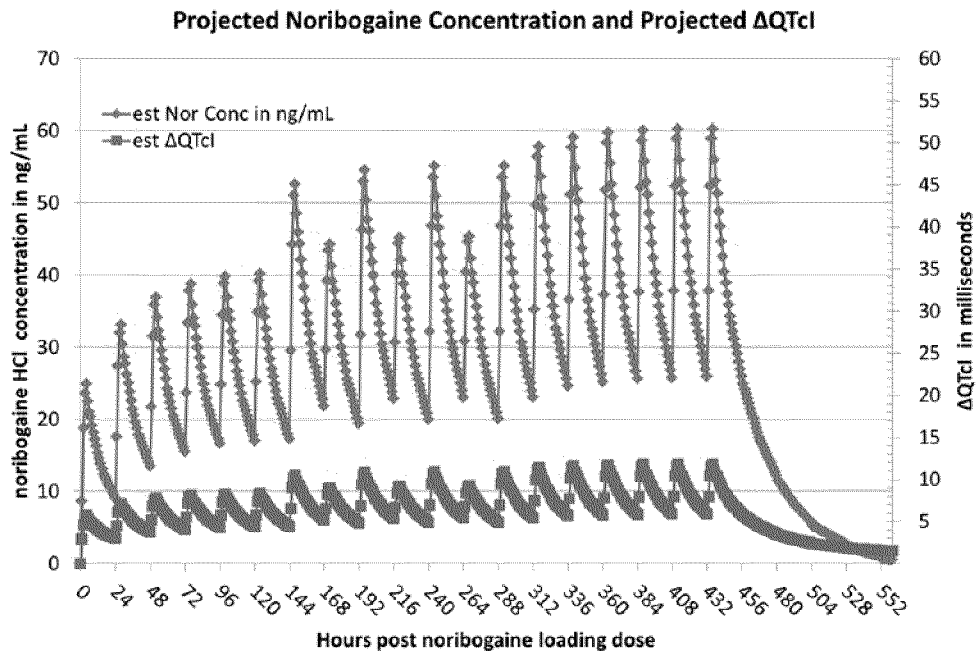
FIG. 11 illustrates the projected noribogaine serum concentration (♦) and projected QT prolongation ($\Delta$QTcI) (■) during the course of noribogaine treatment as described in Example 4, case 2.

A female patient, age 42, undergoing opioid analgesic therapy for acute pain, is treated with noribogaine hydrochloride at the doses indicated in Table 6, concurrently with the opioid. The amount of opioid analgesic administered to the patient is slightly above half of the customary dose given in a similar situation without noribogaine co-treatment. The patient does not exhibit tolerance to or dependence on the opioid during the study period. Table 6 and FIG. 11 indicate the projected serum concentration and increase in QTc1 during the course of treatment. Data are estimated based on the human trial data provided in Examples 1-3.

TABLE 6

| Dose # | INPUT DOSE mg | Projected Mean Plasma Conc ng/mL pre-dose | Projected Mean QTcl Increase in msec pre-dose |
|---|---|---|---|
| 1 | 20 | 17 | 4 |
| 2 | 20 | 17 | 4 |
| 3 | 20 | 17 | 4 |
| 4 | 20 | 15 | 4 |
| 5 | 20 | 13 | 4 |
| 6 | 20 | 9 | 3 |
| 7 | 30 | 13 | 4 |
| 8 | 20 | 15 | 4 |
| 9 | 30 | 17 | 4 |
| 10 | 20 | 17 | 4 |
| 11 | 30 | 17 | 4 |
| 12 | 20 | 22 | 5 |
| 13 | 30 | 19 | 5 |
| 14 | 30 | 23 | 5 |
| 15 | 30 | 20 | 5 |
| 16 | 30 | 23 | 5 |
| 17 | 30 | 20 | 5 |
| 18 | 30 | 23 | 5 |
| 19 | 30 | 25 | 6 |

Example 5. Noribogaine is a G-Protein Biased K-Opioid Receptor Agonist

Selected Abbreviations and Acronyms
GPCR: G protein-coupled receptor
OPRM: μ-opioid receptor
OPRK: κ-opioid receptor
OPRD: δ-opioid receptor
NorBNI: nor-binaltorphimine
DAMGO: [D-Ala2, NMe-Phe4, Gly-ol5]-enkephalin

5.1: Materials and Methods

Materials

[Phenyl-3,4-$^3$H]-U-69,593 (43.6 Ci/mmol), [Tyrosyl-3,5-$^3$H(N)]-DAMGO ([D-Ala$^2$, N-MePhe, Gly$^5$-ol]-enkephalin) (50 Ci/mmol) and [35S]GTPγS (Guanosine 5"-(gamma-thio)triphosphate) (1250 Ci/mmol) were purchased from PerkinElmer Life Sciences (Boston, Mass.). U69,593, naloxone, nor-binaltorphimine (nor-BNI), morphine, nalmefene, dynorphin A, DAMGO, GTPγS, GDP and all buffer constituents were purchased from Sigma-Aldrich Corp. (St. Louis, Mo.). CHO-K1 cell lines expressing human opioid receptors were provided by Dr. Toll at Torrey Pines Institute. Ibogaine was provided by Dr. Mash at the University of Miami (Miami, Fla.). 18-methoxycoronaridine (18-MC) was purchased at Orbiter Pharmaceutical. Noribogaine hydrochloride was purchased at Sigma Aldrich Chemie GmbH (Buchs, Switzerland).

Membrane Preparation

Membranes from rat midbrain tissues were purchased at Chantest (Cleveland, Ohio). Membranes of human OPRK were purchased from PerkinElmer Life Sciences (Boston, Mass.) and human OPRM CHO-K1 cells were prepared as described below. Adherent cells were harvested on ice, with cold PBS and a cell scraper, pelleted and frozen at −80° C. overnight. Cell lysis was performed at 4° C. in 50 mM Tris (pH 7), 2.5 mM EDTA and cOmplete protease inhibitor cocktail (cOmplete, F. Hoffmann-La Roche Ltd). Cells were homogenized with a polytron and centrifuged at 2500 rpm for 10 min at 4° C. Supernatant was recovered and the process was repeated once. Supernatant was centrifuged at 21,000 rpm for 90 min at 4° C. and pellets were re-suspended in 50 mM Tris (pH 7) and 0.32M sucrose. Total protein concentration was evaluated using a Thermo Scientific NanoDrop spectrophotometer and by Bradford assay Membrane sample aliquots were stored at −80° C. at 1 to 5 mg/mL protein concentration. Membranes from brain tissues were stored in 50 mM Tris (pH 7), 1 mM EDTA and 0.32M sucrose with protease inhibitors cocktail.

Radioligand Binding

Competitive binding experiments were performed using Perkin Elmer recommended conditions. Membranes were thawed on ice and diluted in binding buffer 50 mM Tris-HCl pH 7.4, 5 mM MgCl$_2$ at 5 μg of membrane per reaction. Competition binding assay experiment were performed in 500 μL total volume containing [$^3$H]U69,593 (0.88 nM) for OPRK membranes or [$^3$H]DAMGO (0.75 nM) for OPRM membranes in the presence of increasing concentrations of each unlabeled drug (noribogaine, ibogaine, 18-MC, U69,593, morphine, DAMGO, naloxone) for 60 minutes at 25° C. Nonspecific binding was defined in the presence of 1 μM naloxone. Bound and free radiolabelled ligands were separated by filtration using a MicroBeta FilterMate-96 Harvester and wash 6×1 mL with ice cold wash buffer (50 mM Tris-HCl pH 7.4) over GF/B filter (presoaked in 0.5% BSA) (Perkin Elmer, Waltham, Mass.). Radioactivity counts were determined using Perkin Elmer Micro βeta microplate counter with scintillation cocktail MicroScint-20™ according to manufacturer recommendations. Data were collected and the half maximal inhibitory concentration (IC$_{50}$) and apparent binding affinity (K$_i$) for all data sets were calculated with GraphPad Prism 5.04.

[$^{35}$S]GTPγS Binding Assay

[$^{35}$S]GTPγS binding to Gα proteins was determined using a modified procedure from (Toll, Berzetei-Gurske et al. 1998). Cell membranes were thawed on ice and experiments were carried out in a 96-well format. Cell membranes (10 μg per reaction) were incubated in a binding buffer (20 mM HEPES, pH 7.4, 100 mM NaCl, 10 mM MgCl$_2$x6H$_2$O, 0.2% bovine serum albumin, and GDP 10 μM, pH 7.4) containing 80 pM [$^{35}$S]GTPγS and varying concentrations of opioid agonists (U69,593, DAMGO. morphine, dynorphin A, nalmefene, or noribogaine) in a total volume of 100 μL for 60 min at 25° C. Membranes were pre-incubated with the GDP for 15 min on ice prior to the addition of ligands. Antagonists were added to the membrane solution 20 min prior the addition of the agonist, and [$^{35}$S]GTPγS was added 5 min after the agonist. Non-specific and basal levels of GTPγS binding was evaluated by using 10 μM cold GTPγS and binding buffer, respectively. Bound and free [$^{35}$S] GTPγS were separated by filtration using a MicroBeta FilterMate-96 Harvester and wash 4×1 mL with ice cold wash buffer (20 mM Tris, pH 7.4, and 2.5 mM MgCl$_2$x6H$_2$O, pH 7.4) over GF/B filter (presoaked in 0.5% BSA) (Perkin Elmer, Waltham, Mass.). Radioactivity counts were determined using Perkin Elmer Micro βeta microplate counter with scintillation cocktail MicroScint-20™ according to manufacturer recommendations. Data were collected and the half maximal effective concentration (EC$_{50}$) and maximal responses (E$_{max}$) values were calculated with GraphPad Prism 5.04.

β-Arrestin-2 Recruitment Assay

The PathHunter enzyme complementation Arrestin-2 Recruitment assay was performed at DiscoveRx Corporation, Fremont, Calif. This assay utilized CHO-K1 cells stably transfected to overexpress β-arrestin-2 fused to a β-galactosidase fragment together with human OPRK gene (NM_000912.3, human KOR) or human OPRM gene (NM_000914.3, encoding human MOR). Briefly, when β-arrestin-2 travels to active receptor, the complementary β-galactosidase fragments fused to the receptor and β-arrestin interact to form a functional enzyme with activity that is detected by chemiluminescence. For all in vitro assays, data were normalized as a percentage of control agonist responses, typically defined by dynorphin A stimulated activity in the OPRK assays, and [Met] Enkephalin stimulated activity in the OPRM assays. For agonist dose-response experiments, cells were treated with test compound for 90 min prior to assessment of enzyme complementation. For antagonist dose-inhibition experiments, the cells were incubated with the test compound for 30 min prior to agonist addition. For OPRK, a dose corresponding to the EC$_{50}$ (316.9 nM) of Dynorphin A was used. For OPRM a dose corresponding to the EC$_{50}$ (2.1 μM) of [Met] Enkephalin was used.

Data Analysis

The IC$_{50}$ and K$_i$ values for ligands in the radioactive binding assays were determined by fitting competition binding data of individual experiments normalized to buffer (total binding) and 1 μM naloxone (nonspecific binding) to a single site competition model in GraphPad Prism 5.04 using the transformation of Cheng and Prusoff (CFeq): K$_i$=IC$_{50}$/(1+[S]/K$_m$), where [S] is the concentration of agonist and K$_m$ is the K$_i$ value for [$^3$H]U69,593 and [$^3$H]DAMGO determined by homologous competition. The EC$_{50}$ and E$_{max}$ values to agonists for [$^{35}$S]GTPγS binding and β-arrestin-2 translocation were determined by fitting data from individual experiments to sigmoidal concentration-response curves with variable slope in GraphPad Prism 5.04. Final mean and S.E.M. were calculated using individual values from each experiment. Functional inhibitory potency (K$_e$) values for agonist dose-response displacement experiments were calculated using the Gaddum/Schild EC$_{50}$ shift calculation or with the following equation: K$_e$=[nanomolar antagonist]/(dose ratio−1), where dose ratio is the ratio of the EC$_{50}$ for an agonist in the presence and absence of another ligand/inhibitor at a given concentration. K$_e$ values for dose-inhibition experiments were calculated with a modified CFeq: K$_e$=IC$_{50}$/(1+[S]/EC$_{50}$) where [S] is the concentration of agonist used and EC$_{50}$ is the functional potency of the agonist.

Coupling efficiency (e-coupling) values indicated the relationship between the apparent binding affinity K$_i$ versus the apparent functional potency EC$_{50}$ of a given agonist ligand and used the equation pKi-pEC$_{50}$. For the functional inhibitory components of antagonists and partial agonists, e-coupling represents the relationship between the K$_i$ versus the K$_e$ of a given ligand (against Dynorphin A for OPRK assays, and against U69,593 for OPRM assays) and used the equation pK$_i$-pK$_e$. Efficacy efficiency (e-signal) values indicated the ratio of the E$_{max}$ to a given agonist ligand versus the E$_{max}$ to Dynorphin A (or U69,593) and uses the equation E$_{max}$(control agonist)/E$_{max}$(test compound). For inhibitory ligands, e-signal was calculated using maximal level of inhibition (I$_{max}$) normalized from 0 (basal, buffer) to 1 (agonist without inhibitor). Bias-coupling (quantification of pathway bias) was evaluated by subtracting the EC$_{50}$ or the K$_e$ issued from the G-protein pathway assays by those issued from β-arrestin pathway assays for a given ligand and in a linear (nM) scale. Bias-efficacy in favor of the G-protein pathway was evaluated by dividing the functional activation and the functional inhibition maximum responses (e-signal) from the G-protein pathway by the beta-arrestin pathway assays for a given ligand.

μ-Opioid Receptor Ibogaine Binding Model

The mouse μ-opioid receptor OPRM co-crystal structure available in the Protein Data Bank (PDB), PDB accession 4dkl, Uniprot accession P42866 was used in a model of receptor binding. The mouse OPRM has 94% (global) sequence identity to the corresponding human receptor (Uniprot accession P35372) and all residues in the binding site are identical. The receptor was crystallized as a fusion protein (OPRM-T4L) with an irreversible morphine antagonist ligand (bound to Lys233, pdb numbering). All simulations were performed using the Schrodinger 2014.2 and Desmond 2014.2 software suite. For initial docking studies the PDB file was imported into Maestro 9.5 (Schrodinger) and the standard protein preparation workflow was run to assign bond orders and clean up the structure including hydrogen bond optimization and constrained minimization. In the preparation process missing side chains were added using Prime. The fusion protein was manually cut and removed between residues Val262 and Glu270 to leave just the GPCR transmembrane domain; the cut residues were capped as primary amide (C-terminal) and acetate (N-terminal). A (non-covalent) ligand entry (separate from the chain) was manually created in Maestro. The resulting protein complex was again processed via the protein preparation workflow. A docking grid was created around the co-crystal ligand using Glide (standard settings). Several small molecules including the morphinan co-crystal ligand (unbound), Ibogaine, Noribogaine and Voacangine were imported as 2D SDF into Maestro and 3D structure representations were generated using LigPrep (default settings); two representations (inverted at the tertiary bridgehead nitrogen) were generated for each ligand. These were docking using Glide SP (standard settings except keeping 5 poses per compound out of 30 for post-minimization). The docked morphinan ligand reproduced the co-crystal almost perfectly. This docked complex was then optimized using Prime Refine Protein-Ligand complex (default settings). This complex was then used to generate another docking grid using Glide (default settings around the ligand) followed by Glide SP docking of the prepared ligands. In these results, the top poses of noribogaine and ibogaine aligned well the morphinan antagonist (hydrophobic Ibogaine and Noribogaine bicyclic system and ethyl substituent with morphinan cyclopropyl residues and the positively charged tertiary amines, which all form a hydrogen bond to the site chain of Asp147). The μ-OR noribogaine docking complex was then used in a 12 ns molecular dynamics (MD) simulation. The MD system generation and simulations were performed in Desmond using an all atom system with a membrane model and explicit water model (ASP). The Desmond software automatically sets up the systems (adjust charges, adds water molecules) and performs several rounds of minimization and short simulations before the 12 ns production run. MD was run on the Pegasus 2 cluster at the Center for Computational Science at the University of Miami (http://ccs.miami.edu/hpc/) using 48 processors and completed in less than 19 hours. Simulation analysis was performed using the Desmond trajectory analysis software. A representative frame with these most prevalent interactions throughout the simulation was extracted from the trajectory, processed via protein preparation (including constrained minimization) to remove overlapping atoms, and visualized using PyMol.

5.2: Apparent Binding Affinities of Noribogaine to OPRM and OPRK

Figure 12A:
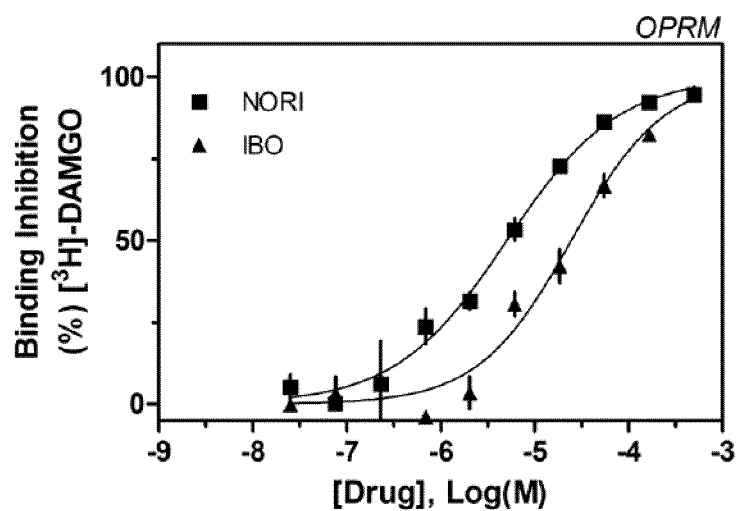
FIG. 12A shows the affinity of noribogaine at the mu (OPRM) opioid receptor based on competitive inhibition by noribogaine and ibogaine of [$^3$H]-DAMGO binding to OPRM. Data used for the non-linear regression analysis are shown as the mean±SEM of each representative experiment(s). Mean±SEM of apparent binding affinity $K_i$ values of a least 3 experiments are shown in Table 7.
Figure 12B:
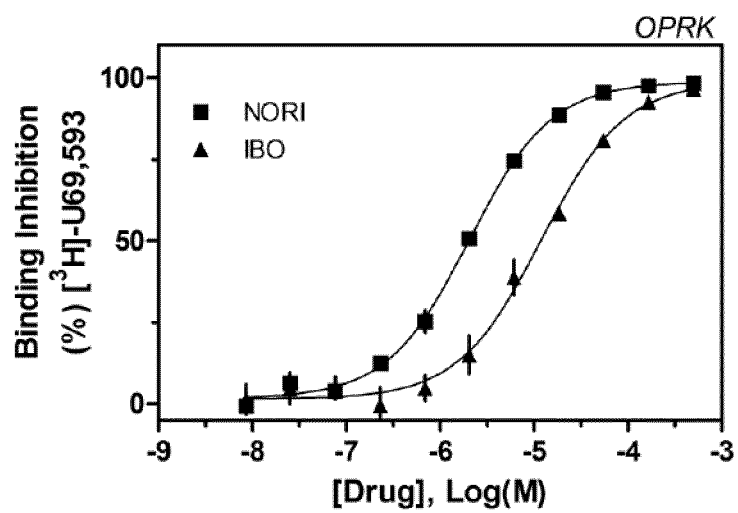
FIG. 12B shows the affinity of noribogaine at the kappa (OPRK) opioid receptor based on competitive inhibition by noribogaine and ibogaine of [$^3$H]-U69,593 binding to OPRK. Data used for the non-linear regression analysis are shown as the mean±SEM of each representative experiment(s). Mean±SEM of apparent binding affinity $K_i$ values of a least 3 experiments are shown in Table 7.

Competitive inhibition of [$^3$H]-U69,593 to human OPRK and of [$^3$H]-DAMGO to human OPRM by noribogaine was conducted and compared to ibogaine, 18-methoxycoronaridine (18-MC) and various control ligands (FIG. 12, Table 7). Noribogaine exhibited the highest apparent affinity for OPRK with a K$_i$ value of 720±128 nM. Ibogaine displayed a K$_i$ of 3.68±0.22 μM, while 18-MC had a K$_i$ a 1.84±0.12 μM. At the OPRM, noribogaine displayed a K$_i$ of 1.52±0.3 μM, while ibogaine and 18-MC K$_i$ values were 6.92±0.83 μM and 2.26±0.35 μM respectively. Values of both noribogaine and ibogaine for the human OPRM/K receptors were comparable that of the calf OPRM and OPRK receptors (1.52 and 0.96 μM, Table 7) where noribogaine was previously shown to be ~30× less affine at OPRD than at OPRK (Pearl, Herrick-Davis et al. 1995). In these assays, 18-MC was equi-affine to both human OPRK and OPRM, contrary to the reported 5× selectivity at OPRM (Glick, Maisonneuve et al. 2000). Experimental values, historical values from the literature, and control ligands, are displayed in Table 7 for agonists, partial agonists, and antagonists used in this study.

TABLE 7

Binding affinity of Noribogaine and other drugs at the human mu (OPRM) and kappa (OPRK) opioid receptors. Ki values of Noribogaine, Ibogaine, 18-MC (n ≥ 3). Values for control ligands Morphine, Naloxone DAMGO, U69,593, Dynorphin A, [Met]-Enkephalin, Nalmefene, Buprenorphine were determined and/or gathered from the literature. Specificity for the OPRK receptor was evaluated using $\Delta pK_i = pKi(OPRK) - pKi(OPRM)$.
Agonists (bold), partial agonists (underline), and antagonists (*italics*).

| Compound | OPRM [$^3$H]-DAMGO binding | | | OPRK Specificity [$^3$H]-U69,593 Binding | | | | References |
|---|---|---|---|---|---|---|---|---|
| | $pK_i$ | $K_i$ (nM) | SEM | $PK_i$ | $K_i$ (nM) | SEM | $\Delta pK_i$ | |
| U69,593 | | N.Q. | | 9.2 | 0.59/0.87 | | >3 | Perkin Elmer/This work |
| DAMGO | 9.1 | 0.6/0.5 | 0.2 | | N.Q. | | <−3 | (Toll, Berzetei-Gurske et al. 1998)/This work |
| Dynorphin A | 8.1 | 7.7 | 2.2 | 8.8 | 1.7-0.05** | 0.85-0.01** | 0.7 | (Toll, Berzetei-Gurske et al. 1998)-(Li, Zhu et al. 1993) |
| [Met]-Enkephalin | 9.2 | 0.63 | | 6.0 | 1000 | | <−3 | (Meng, Xie et al. 1993) |
| Morphine | 9.0 | 1.1 | 0.05 | 7.3 | 46.9 | 4.5 | −1.6 | (Toll, Berzetei-Gurske et al. 1998) |
| Nalmefene | 9.0 | 1 | | 10 | 0.083 | 0.0008 | 1.1 | (Bart, Schluger et al. 2005) |
| Buprenorphine | 10 | 0.08 | 0.02 | 10 | 0.11 | 0.05 | −0.1 | (Huang, Kehner et al. 2001) |
| 6'GNTI | 7.1 | 82 | 21 | 8.9 | 1.15 | 0.39 | 1.84 | (Sharma, Jones et al. 2001) |
| Noribogaine | 5.6 | 2660* | (OPRD = 24720) | 6.0 | 960* | | 0.4 | (Pearl, Herrick-Davis et al. 1995) |
| | 5.8 | 1520 | 300 | 6.1 | 720 | 128 | 0.3 | This work |
| Ibogaine | 5.0 | 11040* | (OPRD – N.Q.) | 5.4 | 3770 | | 0.5 | (Pearl, Herrick-Davis et al. 1995) |
| | 5.2 | 6920 | 830 | 5.4 | 3680 | 220 | 0.3 | This work |
| 18-MC | 6.0 | 1100* | 300 | 5.3 | 5100* | 500 | −0.7 | (Glick, Maisonneuve et al. 2000) |
| | 5.6 | 2360 | 350 | 5.7 | 1840 | 120 | 0.1 | This work |
| Naloxone | *8.9* | 1.4/1.3 | 0.05 | *8.6* | 2.5 | 0.3 | −0.3 | (Toll, Berzetei-Gurske et al. 1998)/This work |
| NorBNI | *7.7* | 21 | 5 | *9.7* | 0.2-0.04** | 0.05-0.01** | 2.0 | (Toll, Berzetei-Gurske et al. 1998)(Li, Zhu et al. 1993) |

*calf receptor;
**[$^3$H]diprenorphine binding;
OPRD: human opioid receptor delta;
N.Q. non-quantifiable 5.3: Functional Agonist Properties of Noribogaine at OPRM and OPRK [$^{35}$S]GTPγS Binding Stimulation.

Figure 13A:
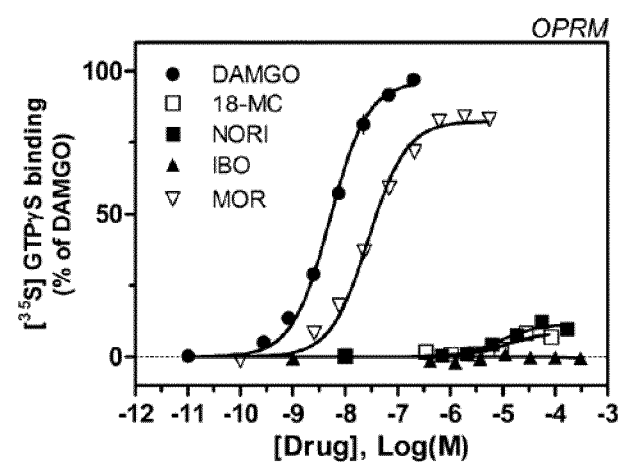
FIG. 13A shows noribogaine-induced stimulation of [$^{35}$S] GTPγS binding at the mu (OPRM) opioid receptors. CHO-K1 cells membrane preparation expressing the OPRM receptors were stimulated by increasing concentrations of agonists (DAMGO, Morphine: MOR, Nalmefene: NALM) and test compounds (Noribogaine: NORI, Ibogaine: IBO; 18-MC). Data used for the non-linear regression analysis are shown as the mean±SEM of each representative experiment(s). Mean±SEM of $EC_{50}$ and $E_{max}$ values of 2 to 10 experiments are shown in Table 8.
Figure 13B:
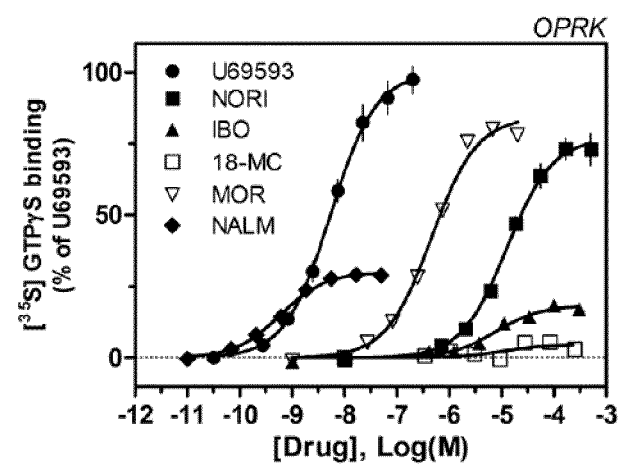
FIG. 13B shows noribogaine-induced stimulation of [$^{35}$S] GTPγS binding at the kappa (OPRK) opioid receptors. CHO-K1 cells membrane preparation expressing the OPRK receptors were stimulated by increasing concentrations of agonists (DAMGO, Morphine: MOR, Nalmefene: NALM) and test compounds (Noribogaine: NORI, Ibogaine: IBO; 18-MC). Data used for the non-linear regression analysis are shown as the mean±SEM of each representative experiment(s). Mean±SEM of $EC_{50}$ and $E_{max}$ values of 2 to 10 experiments are shown in Table 8.

[$^{35}$S]GTPγS binding to membranes of CHO cells stably transfected with OPRK or OPRM was examined in response to noribogaine, ibogaine, morphine, and nalmefene drug treatment and measured the activation of the G-protein pathway by agonists (FIGS. 13A and 13B). The prototypical full agonist U69,593, and the endogenous ultra-potent agonist, Dynorphin A, were used as controls for OPRK function and DAMGO was used for OPRM. Calculated $EC_{50}$ and $E_{max}$ values are enumerated in Table 8.

Noribogaine was marginally active at stimulating [$^{35}$S]GTPγS binding to OPRM, with an $E_{max}$ of 10% the full agonist DAMGO (FIG. 13A) and comparable to the level of activation previously reported (Antonio, Childers et al. 2013). Morphine was a partial agonist with an $E_{max}$ of 80±4.5% of DAMGO signal and an $EC_{50}$ of 32±1.2 nM. The partial agonist buprenorphine stimulated OPRM with an $E_{max}$ of 26±2.2% in these assays, as previously reported (Saidak, Blake-Palmer et al. 2006), and ibogaine and 18-MC failed to stimulate the OPRM G-protein pathway.

Noribogaine was a partial agonist at stimulating [$^{35}$S]GTPγS binding to OPRK with an $E_{max}$ of 72±3.8% of U69,593, and an $EC_{50}$ of 8.75±1.09 μM (FIG. 13B). Ibogaine displayed a lower agonist power than noribogaine at OPRK with an $E_{max}$ of 18±1.4%, while 18-MC failed to stimulate [$^{35}$S]GTPγS binding to OPRK. In these assays, morphine and dynorphin A displayed $E_{max}$ values of 91±7% and 94±7% respectively, and nalmefene, a partial agonist of OPRK, maximally stimulated at 35±4.7% and similar to formally reported values (Bart, Schluger et al. 2005).

The apparent coupling efficiencies of agonists DAMGO, U69,593, morphine, dynorphin A, nalmefene, 6'GNTI, noribogaine and ibogaine at the G-protein pathway were calculated (see methods) and found to be congruent with values shifted by ~1 log (Tables 2 and 5). Dynorphin A and 6'GNTI were outliers and displayed better coupling efficiencies (0.56 and 0.26) than other agonists at stimulating [$^{35}$S]GTPγS binding in comparison to their apparent binding affinities against [$^3$H]U69,593 and [$^3$H]diprenorphin (Tables 2 and 5).

TABLE 8

Activation and inhibition by Noribogaine of [$^{35}$S]GTPγS binding in CHO—K1 stably expressing human OPRM and OPRK.
Data used for the non-linear regression analysis are shown as the mean ± SEM of (n) experiments. [Met]-Enkephalin and 6'GTNI values were gathered from references as indicated. Non-italic section indicates values (EC$_{50}$) for the activation component of the ligand and italic section indicates the values (K$_e$) for the inhibitory component of the ligand.
Coupling efficiency (e-coupling) was calculated as in methods. Outliers are underlined.

| Compound Activation/*Inhibition* | [35S]GTPgS Binding Activation | | | | | | | | |
|---|---|---|---|---|---|---|---|---|---|
| | pEC$_{50}$ | EC$_{50}$ (nM) | (SEM) | n | Efficacy (%) | (SEM) | n | e-coupling | References |
| OPRM: | | | | | | | | | |
| DAMGO | 7.5 | 29 | 9 | 7 | 100 | | n.a. | 1.77 | |
| [Met]-Enkephalin | 7.4 | ~40 | | | ~95 | | | 1.8 | (Saidak, Blake-Palmer et al. 2006) |
| Morphine | 7.5 | 32 | 1.2 | 3 | 80 | 4.5 | 4 | 1.47 | |
| Buprenorphine | | n.d. | | | 26 | 2.2 | 2 | n/d | |
| Noribogaine | 4.8 | 16050 | 9409 | 4 | 9.4 | 1.8 | 4 | 1.02 | |
| Ibogaine | | n.d. | | 2 | −2.9 | | | | |
| 18-MC | | n.d. | | 2 | <5 | | | | |
| 6'GNTI | | >1000 | | | 0~ | | | | (Waldhoer, Fong et al. 2005) |
| *Noribogaine* (K$_e$) | *4.7* | *19203* | *5168* | *−100~* | | | | *1.10* | |
| *Naloxone* (K$_e$) | *8.5* | *3.36* | *0.75* | *−100* | | | | *0.38* | |
| PRK: | | | | | | | | | |
| U69,593 | 8.1 | 7.25 | 0.9 | 9 | 100 | | n.a. | 0.92 | |
| Dynorphin A | 9.7 | 0.18 | 0.04 | 6 | 94 | 7 | 3 | 0.56 | |
| Morphine | 6.4 | 434 | 67 | 4 | 91 | 7 | 3 | 0.97 | |
| Noribogaine | 5.1 | 8749 | 1092 | 10 | 72 | 3.8 | 14 | 1.08 | |
| Nalmefene | 9.2 | 0.69 | 0.14 | 3 | 35 | 4.7 | 3 | 0.92 | |
| 6'GNTI | 8.7 | 2.1 | 0.5 | | 37 | 2 | | 0.26 | (Schmid, Streicher et al. 2013) |
| Ibogaine | 4.9 | 12000~ | | 2 | 18 | 1.4 | | 1.39~ | |
| 18-MC | 4.8 | 16000~ | | 2 | <5 | | | 0.94~ | |
| *Noribogaine* (K$_e$)-*U69* | *4.9* | *11560* | *786* | | *−30* | | | *1.22* | |
| *Noribogaine* (K$_e$)-*Dyn* | *4.4* | *39797* | *15560* | | *−25* | | | *1.72* | |
| *Nalmefene* (K$_e$) | *9.9* | *0.14* | *0.04* | | *−65* | | | *0.23* | |
| *6'GNTI* (K$_e$) | *9.7* | *0.18* | | | *−32* | | | *−0.81* | Adapted from (Schmid, Streicher et al. 2013) |
| *18 MC* (K$_e$) | *5.3* | *4556* | *1392* | | *−100* | | | *0.39* | |
| *NorBNI* (K$_e$) | *10.5* | *0.03269* | | | *−100* | | | *−0.1* | |
| *Naloxone* (K$_e$) | *8.5* | *3.36* | *0.75* | | *−100* | | | *0.13* | | n/a non-applicable. n/d not determined 5.4: Functional Inhibitory Properties of Noribogaine at OPRM [$^{35}$S]GTPγS Binding Stimulation.

Figure 14A:
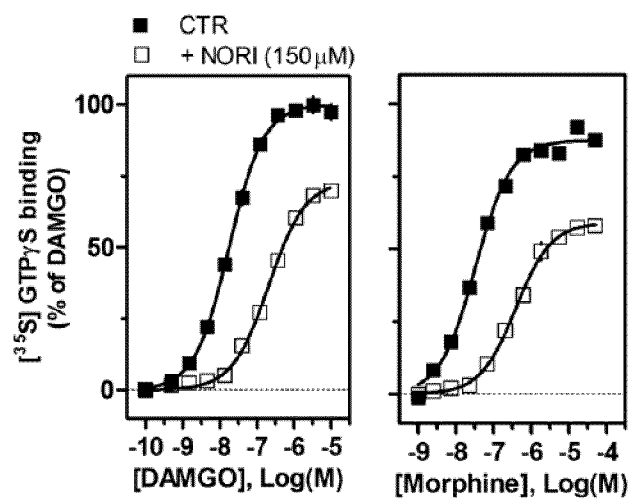
FIG. 14A shows noribogaine inhibition of agonist-induced [$^{35}$S]GTPγS binding at the mu receptor (OPRM). CHO-K1 cells membrane preparation expressing the OPRM receptors were stimulated by increasing concentration of agonists DAMGO and Morphine (MOR) in the presence of 150 μM Noribogaine. Data used for the non-linear regression analysis are shown as the mean±SEM of each representative experiment(s) performed in triplicate.
Figure 14B:
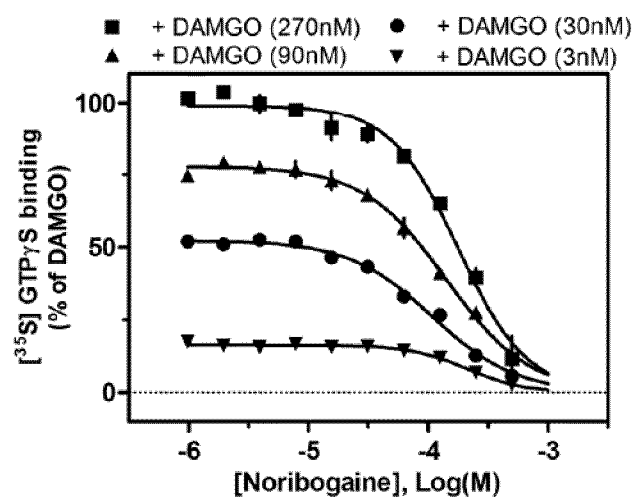
FIG. 14B shows noribogaine inhibition of agonist-induced [$^{35}$S]GTPγS binding at the mu receptor (OPRM). [$^{35}$S]GTPγS binding signal from four concentrations of DAMGO (3, 30, 90, and 270 nM) was recorded in the presence of increasing concentrations of noribogaine. Data used for the non-linear regression analysis are shown as the mean±SEM of each representative experiment(s) performed in triplicate.

Noribogaine marginally stimulated [$^{35}$S]GTPγS binding via OPRM with an approximated EC$_{50}$ of 16 μM (FIG. 13A). Therefore, whether noribogaine is an antagonist of OPRM was investigated. DAMGO and morphine dose responses were carried out in the presence and absence of 150 μM of noribogaine (FIG. 14A). Noribogaine was an inhibitor of both agonists tested and right-shifted their EC$_{50}$ by a magnitude of ~1 log. The calculated K$_e$ values (see methods) were 19±5 μM against DAMGO and 28±14 μM against morphine (Table 8) and both were in the concentration range of the EC$_{50}$ of noribogaine at OPRM G-protein pathway. In a similar design, naloxone displayed a K$_e$ of 3.36±0.75 nM, a value close to its K$_i$ at OPRM (Tables 7 and 8). Noribogaine also decreased the E$_m$ of both DAMGO and morphine dose-responses curves in this assay (FIG. 14A), indicating partial unsurmountable antagonism that can encompass several distinct molecular mechanisms such as (a) irreversible competitive antagonism, (b) noncompetitive antagonism, and/or (c) functional antagonism; for review (Neubig, Spedding et al. 2003). Dose-inhibition curves of noribogaine against increasing doses of DAMGO were performed (FIG. 14B). Noribogaine dose-dependently inhibited DAMGO-stimulated [$^{35}$S]GTPγS binding at OPRM with an IC$_{50}$ of 134±17 μM, independent of the agonist concentrations of DAMGO.

5.5: Functional Inhibition of Noribogaine-Induced OPRK [$^{35}$S]GTPγS Binding by Antagonists.

Figure 15:
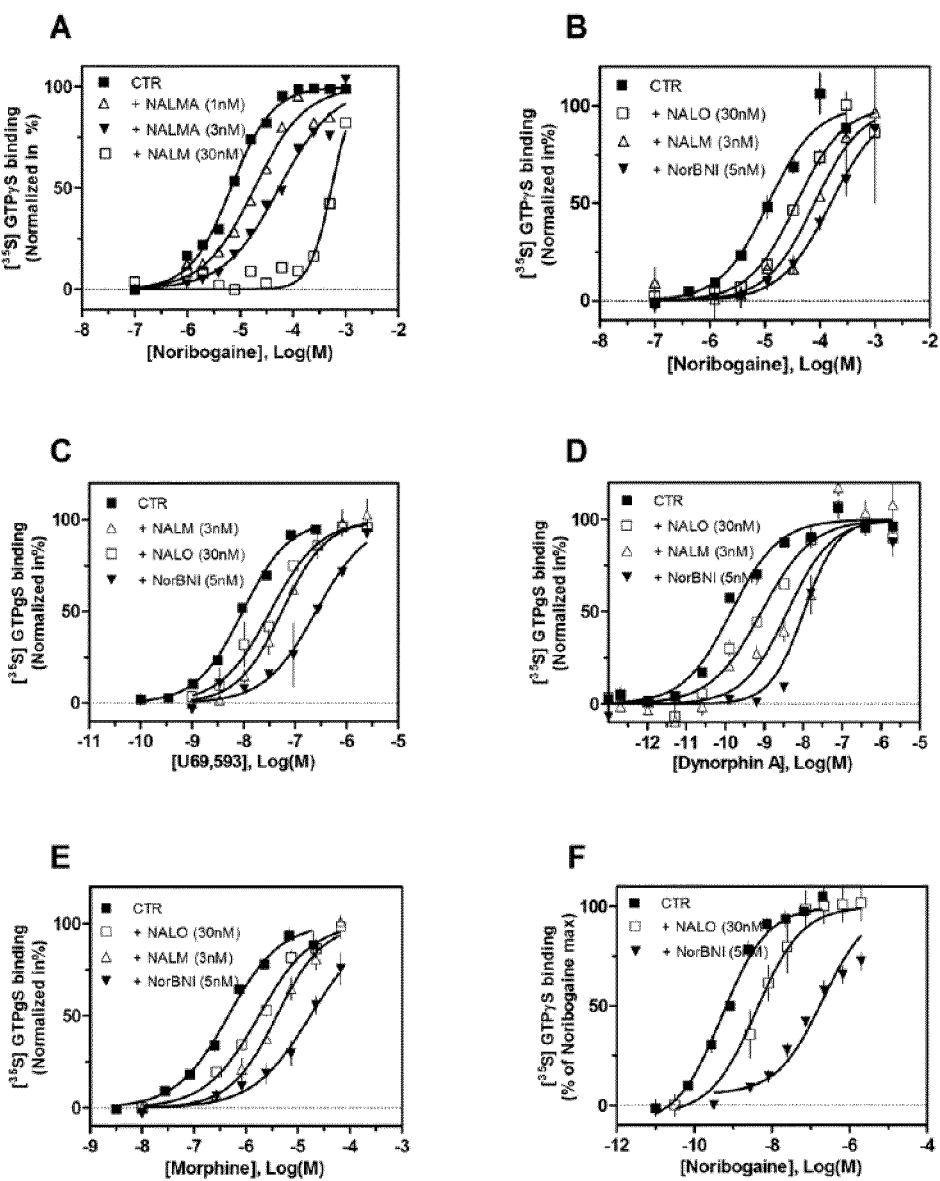
FIG. 15 shows inhibition of noribogaine-induced [$^{35}$S]GTPγS binding by OPRK antagonists. (Panel A) Noribogaine dose-response curves were examined in the presence of increasing concentrations of Nalmefene (NALM). (Panels B-E) The inhibitory effects of antagonists Naloxone (NALO—30 nM), Nalmefene (NALM—3 nM) and NorBNI (5 nM) were tested against increasing concentrations of Noribogaine, and control agonists U69,593, Dynorphin A, Morphine, and Nalmefene-induced signal. Functional inhibition constant Ke was extracted for each dose response-curve shifts and Table 9 represents the mean±SEM of 3-7 experiments. Data used for the analysis are shown as the mean±SEM of representative experiment(s).

Inhibitory effects of naloxone, Nor-BNI, and nalmefene on the agonist-induced [$^{35}$S]GTPγS binding to OPRK by noribogaine and U69,593, Dynorphin A, morphine, and nalmefene were investigated (FIG. 15, Table 9). Dose-responses to these agonists were gathered in the absence and presence of fixed antagonist concentration: 30 nM Naloxone, 5 nM Nor-BNI, and 3 nM nalmefene. The compound 18-MC was also tested, which appeared to be an antagonist in this assay with a K$_e$ of 4.5±1.4 μM against U69,593.

Antagonists and partial agonist nalmefene dose-dependently right-shifted the dose-response curves of noribogaine, consistent with the addition of a surmountable competitor of the noribogaine binding site (FIG. 15). Functional inhibition constants (K$_e$) for antagonists are shown in Table 9 with the assumption of ideal conditions of competitiveness and equilibrium. In all instances, the functional inhibition constants for these inhibitors were close to their K$_i$, indicating that noribogaine was no different than other agonists tested and was apparently competing for a common binding site.

TABLE 9

Functional inhibition constants $K_e$ of Noribogaine and other ligands to agonist-induced [$^{35}$S]GTPγS binding in CHO—K1 stably expressing human OPRK. Data used for the non-linear regression analysis are shown as the mean ± SEM of 3 up to 7 experiments. Italic value represents the estimate of a hypothetical functional activation constant of designated agonist in the presence of other agonists.

| Antagonists & Rival agonists $K_e$ (nM) | U69'593 | Dynorphin A | Morphine | Noribogaine | Nalmefene | $K_i$ | $EC_{50}$ |
|---|---|---|---|---|---|---|---|
| U69'593 | n/a | n/a | n/d | *0.4* | *4* | 0.9 | 7.3 |
| Dynorphin A | n/a | n/a | n/a | *0.003* | *0.1* | 0.05 | 0.18 |
| Morphine | n/d | n/a | n/a | *74* | *270* | 47 | 434 |
| Noribogaine | 12e3 ± 0.8e3 | 40e3 ± 16e3 | 15e3 ± 4e3 | n/a | *24e3* | 700 | 8.7e3 |
| Nalmefene | 0.14 ± 0.04 | 0.077 ± 0.016 | 0.11 ± 0.005 | 0.33 ± 0.07 | n/a | 0.08 | 0.7 |
| *Naloxone* | 8.6 ± 1.3 | 4.8 ± 0.9 | 8.2 ± 1.2 | 4.2 ± 2.3 | 9.2 | 2.5 | n/a |
| *NorBNI* | 0.12 ± 0.04 | 0.029 ± 0.004 | 0.07 ± 0.013 | 0.075 ± 0.036 | 0.1 ± 0.09 | 0.2 | n/a |
| *18-MC* | 4.5e3 ± 1.4e3 | 2.8e3 ± 0.6e3 | 2.9e3 ± 0.7e3 | 4.3e3 ± 1.9e3 | n/d | 1.8e3 | n/a | n/a non-applicable. n/d not determined 5.6: Residual Functional Antagonist Properties of Noribogaine at OPRK [$^{35}$S]GTPγS Binding Stimulation.

Noribogaine was a partial agonist at OPRK in the [$^{35}$S]GTPγS binding stimulation assays (FIG. 13). Therefore, it was investigated whether noribogaine, termed here as 'rival agonist', and the partial agonist nalmefene was able to functionally compete with and level down the activity of more efficacious agonists than itself.

Figure 16A:
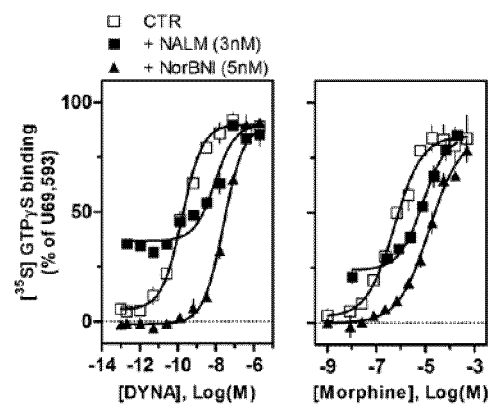
FIG. 16A shows that noribogaine partially inhibits of agonist-induced [$^{35}$S]GTPγS binding at the kappa receptor (OPRK). Experiments tested the effects of the partial agonist, Nalmefene (NALM), in the presence of other agonists. CHO-K1 cells membrane preparation expressing the OPRK receptors were stimulated by increasing concentration of agonists Dynorphin A (left panel—DYNA) or Morphine (right panel—MOR) in the presence of 3 nM Nalmefene or 150 μM Noribogaine at ~5× their EC50. Control antagonist NorBNI was added at 5 nM and 100 μM and compared for right-shift of the agonists dose-responses. Data are shown as the mean±SEM of representative experiment(s) performed in triplicate.
Figure 16B:
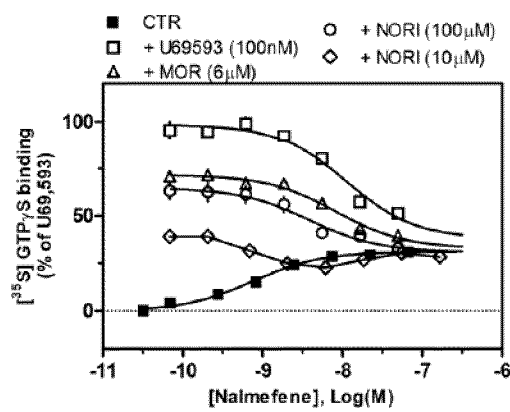
FIG. 16B shows that noribogaine partially inhibits of agonist-induced [$^{35}$S]GTPγS binding at the kappa receptor (OPRK). Experiments tested the effects of the partial agonist, Nalmefene (NALM), in the presence of other agonists. Membranes were stimulated by increasing concentrations of Nalmefene in the presence of agonists U69,593 (100 nM), Morphine (MOR—6 and 5 μM), and Noribogaine (NORI—10 and 100 μM). Data are shown as the mean±SEM of representative experiment(s) performed in triplicate.
Figure 16C:
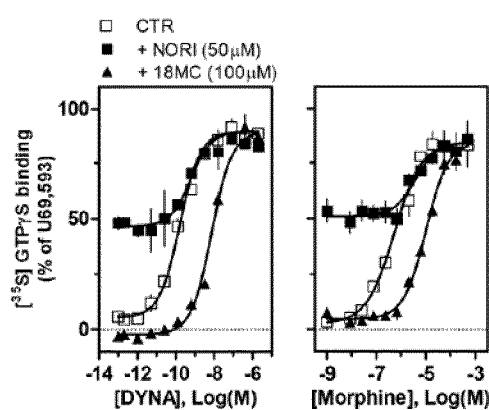
FIG. 16C shows that noribogaine partially inhibits of agonist-induced [$^{35}$S]GTPγS binding at the kappa receptor (OPRK). Experiments tested the effects of the partial agonist, Noribogaine (NORI), in the presence of other agonists. CHO-K1 cells membrane preparation expressing the OPRK receptors were stimulated by increasing concentration of agonists Dynorphin A (left panel—DYNA) or Morphine (right panel—MOR) in the presence of 3 nM Nalmefene or 150 μM Noribogaine at ~5× their EC50. Control antagonist 18-MC was added at 5 nM and 100 μM in similar conditions and compared for right-shift of the agonists dose-responses. Data are shown as the mean±SEM of representative experiment(s) performed in triplicate.

Dynorphin A and morphine dose-responses curves were performed in the presence and the absence of rival agonists nalmefene or noribogaine at concentrations of ~5× their $EC_{50}$ (nalmefene 3 nM, noribogaine 50 µIV) (FIGS. 16A and 16C). Nalmefene readily right-shifted the $EC_{50}$ of Dynorphin A and morphine with an apparent $K_e$ of 0.077±0.016 nM and 0.11±0.005 nM, within the range of its apparent Ki (0.08 nM) and similar to the pure antagonist NorBNI (Table 9). Noribogaine, on the other hand, poorly right-shifted the $EC_{50}$ of these agonists and the $K_e$ estimates in these conditions were 40±16 µM and 15±4 µM respectively, about 40× its $K_i$. (Table 9, underlined values).

Figure 16D:
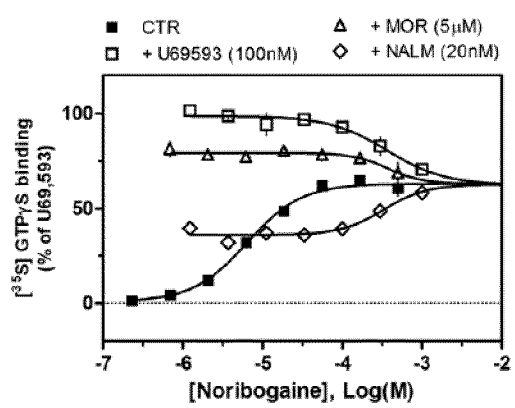
FIG. 16D shows that noribogaine partially inhibits of agonist-induced [$^{35}$S]GTPγS binding at the kappa receptor (OPRK). Experiments tested the effects of the partial agonist, Noribogaine (NORI), in the presence of other agonists. Membranes were stimulated by increasing concentrations of Noribogaine in the presence of agonists U69,593 (100 nM), Morphine (MOR-6 and 5 μM), and Nalmefene (NALM—20 nM). Data are shown as the mean±SEM of representative experiment(s) performed in triplicate.

In another set of experiments (FIGS. 16B and 16D), noribogaine and nalmefene dose-response curves were produced in the presence of a set concentration of agonists. Nalmefene readily leveled-down the signal of moderate to high concentrations of rival full (U69,593) or partial (noribogaine) agonists to its own reduced levels (30%) with an apparent $IC_{50}$ proportional to the rival agonist concentration (including noribogaine). Noribogaine also leveled-down the signal of high concentrations of rival agonists to its own reduced signal (70%), but the $IC_{50}$ values were high (100-300 µM range). Finally, the apparent functional potency of dynorphin A, U69'593 and morphine were estimated by being set as rival agonist dose-responses in the presence of either noribogaine or nalmefene. In this setting, the calculated $K_e$ (activation) for all rival agonists were lower in the presence of noribogaine than in the presence of nalmefene (close to their experimental $EC_{50}$) and showed that noribogaine was a somewhat poor functional blocker of these agonists (Table 9, underlined values).

5.7: Functional Antagonist Properties of Noribogaine at OPRK-Mediated β-Arrestin-2 Recruitment.

Figure 17A:
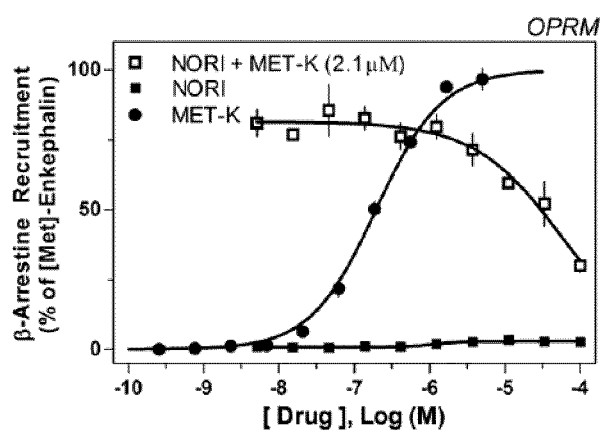
FIG. 17A shows that noribogaine inhibits agonist-induced β-arrestin recruitment at the mu (OPRM) receptor. CHO-K1 cells expressing the OPRM receptors were stimulated by increasing concentrations of the reference agonist [Met]-Enkephalin (MET-K) and test compound Noribogaine (NORI). Reference agonists were applied at a concentration of 80% their EC50 in the presence of increasing concentrations of noribogaine. Data used for the non-linear regression analysis are shown as the mean±SEM of one standardized experiment performed in duplicate.
Figure 17B:
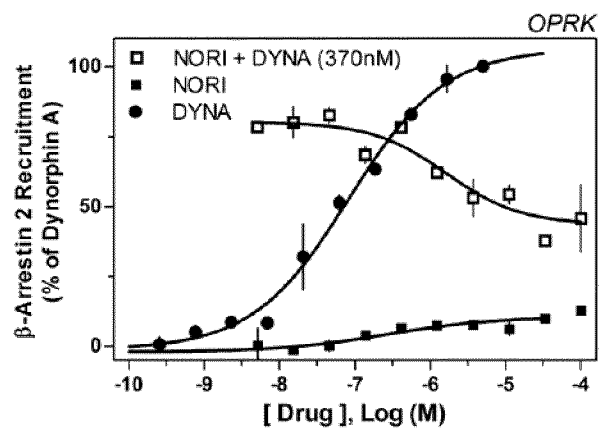
FIG. 17B shows that noribogaine inhibits agonist-induced β-arrestin recruitment at the kappa (OPRK) receptors. CHO-K1 cells expressing the OPRK receptors were stimulated by increasing concentrations of the reference agonist Dynorphin A (DYNA) and test compound Noribogaine (NORI). Reference agonists were applied at a concentration of 80% their EC50 in the presence of increasing concentrations of noribogaine. Data used for the non-linear regression analysis are shown as the mean±SEM of one standardized experiment performed in duplicate.

PathHunter β-Arrestin GPCR assays detecting the interaction of β-Arrestin with the activated receptor were used to measure non-G protein OPRM&K activity as in (Violin, Crombie et al.). Dose-response curves to noribogaine were compared to full agonists [Met]-enkephalin (OPRM), and Dynorphin A (OPRK) drug treatments (FIGS. 17A and 17B). Calculated $EC_{50}$ values, maximal responses and coupling efficiencies are shown in Table 10. Control agonist [Met]-Enkephalin displayed an $EC_{50}$ of 193±11 nM at OPRM and Dynorphin A displayed an $EC_{50}$ of 82±21 nM at OPRK. Noribogaine displayed a profound functional bias at OPRK and was marginally efficacious at inducing β-Arrestin-2 recruitment at OPRK with an $E_{max}$ of 12.6±3% of dynorphin A maximal stimulation and an estimated $EC_{50}$ of 265 nM. Noribogaine was also not an agonist at OPRM.

Figure 18:
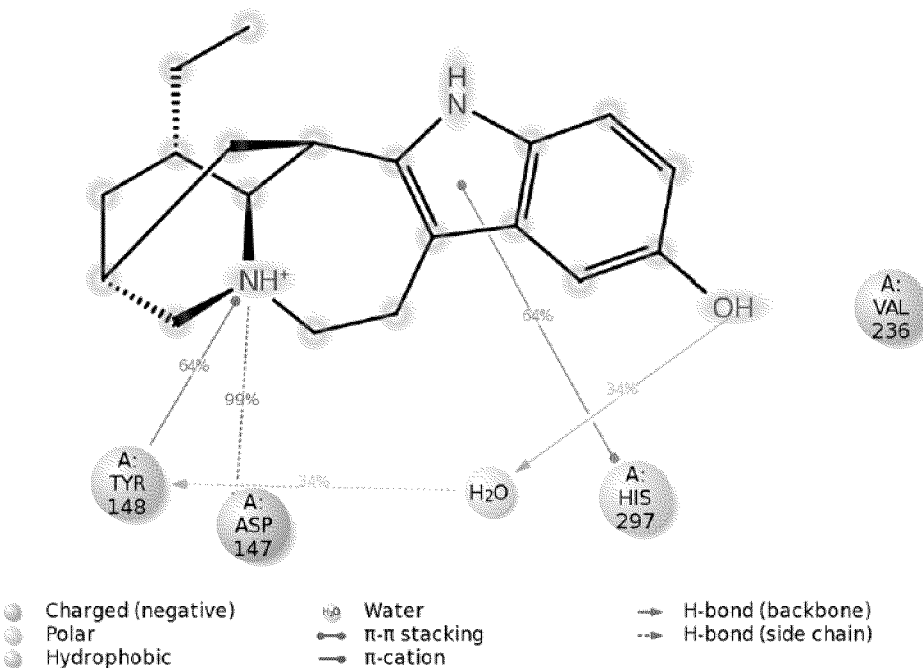
FIG. 18 shows ligand-protein binding contacts of Noribogaine with OPMR over a 12 ns molecular dynamics simulation; data shown are the prevalent interactions that occur more than 30% in the simulation time.

Noribogaine was then tested for its ability to inhibit agonist-induced β-Arrestin-2 recruitment at OPRM and OPRK (FIGS. 17A and 17B). In these assays, β-Arrestin-2 recruitment was induced by the agonists [Met]-Enkephalin (OPRM) and Dynorphin A (OPRK) at their $EC_{80}$ concentration and challenged with increasing concentrations of noribogaine. Noribogaine inhibited agonist responses at OPRM and OPRK up to 60-100% and ~60%, with an 1050 of ~57 µM and 1.45±1.1 µM respectively (FIG. 18). The $K_e$ values were ~4.8 µM and 262 nM for OPRM and OPRK respectively (Table 10). Thus, noribogaine was apparently 144× more potent at inhibiting Dynorphin A-induced β-arrestin-2 recruitment than at inhibiting Dynorphin A-induced G-protein activation (Table 11).

TABLE 10

Activation and inhibition by Noribogaine of β-arrestin 2 recruitment in
CHO—K1 stably expressing human OPR1VI and OPRK.
Data used for the non-linear regression analysis are shown as the mean ± SEM of one standardized experiment.
Morphine, buprenorphine and 6'GTNI values were gathered from references as indicated. Non-italic section
indicates values ($EC_{50}$) for the activation component of the ligand and italic section indicates the values ($K_e$) for
the inhibitory component of the ligand. Coupling efficiency (e-coupling) was calculated as in methods.

| | β-arrestin 2 recruitment | | | | | | |
|---|---|---|---|---|---|---|---|
| Compound | | $EC_{50}$ | | Efficacy | | | |
| Activation/*Inhibition* | $pEC_{50}$ | (nM) | (SEM) | (%) | (SEM) | e-coupling | References |
| OPRM: | | | | | | | |
| DAMGO | 6.1 | 794 | | 100 | | 3.20 | (DeWire, Yamashita et al. 2013) |
| [Met]-Enkephalin | 6.7 | 193 | 11 | 100 | | 1.94 | |
| Morphine | 6.3 | 501 | | 11.3 | | 2.66 | (DeWire, Yamashita et al. 2013) |
| Buprenorphine | | n/a | | 0 | | n/a | (DeWire, Yamashita et al. 2013) |
| Noribogaine | 5.9 | ~1150 | | 3 | 0.5 | n/a | |
| *Noribogaine* ($K_e$) | *4.2* | *~4794* | | *~100~* | | *~1.10* | |
| OPRK: | | | | | | | |
| U69'593 | 7.2 | 59 | | 100 | | 1.83 | (Schmid, Streicher et al. 2013) |
| Dynorphin A | 7.1 | 82 | 21 | 100 | | 3.22 | |
| Noribogaine | 6.6 | ~265 | | 12.6 | 3 | −0.43 | |
| 6'GNTI | 8.2 | 5.9 | 3.3 | 12 | 3 | 0.71 | (Schmid, Streicher et al. 2013) |
| *Noribogaine* ($K_e$)-*Dyn* | *6.6* | *262* | | *~60~* | | *−0.44* | |
| *6'GNTI* ($K_e$) | *9.3* | *0.56* | | *−69* | *2* | *−0.31* | Adapted from (Schmid, Streicher et al. 2013) |
| *NorBNI* ($K_e$) | *9.4* | *0.37* | | *−100* | | *0.27* | |

TABLE 11

Noribogaine activation and inhibition bias quantification at OPRK.

| | G-protein Pathway | | Beta-Arrestin2 Pathway | | Bias G-protein/Beta-arrestin2 | |
|---|---|---|---|---|---|---|
| Activation | e-coupling | e-signal | e-coupling | e-signal | Bias-coupling | Bias-efficacy |
| U69'593 | 0.92 | 1.00 | 1.83 | 1.00 | 1/8 | 0 |
| Dynorphin A | 0.56 | 0.94 | 3.22 | 1.00 | 1/457 | −0.06 |
| Noribogaine | 1.08 | 0.72 | −0.43 | 0.13 | 32 | 0.59 |
| 6'GTNI | 0.26 | 0.37 | 0.71 | 0.12 | 1/3 | 0.25 |
| Inhibition | e-coupling | e-signal | e-coupling | e-signal | Bias-coupling | Bias-efficacy |
| Noribogaine | 1.72 | 0.25 | −0.44 | 0.60 | 144 | −0.35 |
| 6'GTNI | −0.81 | 0.32 | −0.31 | 0.69 | 1/3 | −0.37 |

Figure 19:
FIG. 19 shows a binding model of Noribogaine in OPMR extracted from a molecular dynamics simulation.

5.8: Binding Model of Noribogaine and Ibogaine to the Inactive Conformation of OPRM An in silico binding model was developed based on the mouse OPRM co-crystal structure [PMID 22437502] (Manglik, Kruse et al. 2012) as described in methods. The mouse and human OPRM share 94% (global) sequence identity and all binding site residues are identical. After initial optimization of the model, the top docking poses of noribogaine and ibogaine were pharmacophorically aligned with the co-crystal morphinan antagonist as one would expect: the hydrophobic ibogaine and noribogaine bicyclic system and ethyl substituent with morphinan cyclopropyl residues were spatially aligned and the positively charged tertiary amines were superimposed with each forming a hydrogen bond to the site chain of Asp147. Then, the noribogaine and ibogaine OPRM complexes were each used in a 12 ns all atom explicit water molecular dynamics simulation (see methods). Trajectory analysis revealed the most prevalent interactions of noribogaine (FIG. 18) and ibogaine. Both ligands formed a stable hydrogen bond with Asp147 via their tertiary amine. Noribogaine and ibogaine formed pi-cation interaction with Tyr148 (64 and 56%, respectively), and hydrophobic interactions with His297 (64 and 93%, respectively). Further hydrophobic interactions were observed between Val236 (~40 and ~60%, respectively), Tyr326 (~20 and ~40% respectively), Met151 (~20% and ~30%, respectively) and also Trp293, Ile296, Val300. Characteristically, noribogaine, but not ibogaine, formed a water bridge with Tyr148 for 34% of the simulation time. Both ligands showed a hydrogen bond with His297 for about 20% of the simulation. A representative illustration frame of noribogaine in the OPRM was extracted from the simulation and is shown in FIG. 19.

Discussion

Historically, in vivo studies excluded the possibility of prototypical agonistic mechanism of ibogaine and noribogaine at the mu and/or kappa opioid receptors while potential antagonistic mechanisms were also not conclusive. These ambiguous results lead research groups to provide non-opioid mechanistic explanations to the effects of ibogaine and noribogaine with opiate drugs and in the opioid system. This study now demonstrates that noribogaine is in fact a mixed agonist-antagonist of OPRK and OPRM as well as a profound G-protein biased OPRK ligand. Ibogaine and 18-MC were either not agonists or poor agonists of OPRM or OPRK. 18-MC was a regular competitive antagonist of agonist-induced OPRK signaling. Thus, noribogaine belongs to a different class of opioid ligands than ibogaine or 18-MC.

Pharmacological manipulations, especially with partial agonists, of the OPRK/dynorphin tone may hold potential for the treatment of certain drug addictions and psychiatric comorbidity. Finally, it was shown that noribogaine triggered the release of prolactin in rats and that this effects was centrally mediated (Baumann, Rothman et al. 2001). Without being bound by theory, it is believed that noribogaine-induced prolactin release is mediated by the direct activation of OPRK, similar to what was proposed for nalmefene (Bart, Schluger et al. 2005)

In line with their localization in the hippocampus, amygdala, hypothalamus, striatum and spinal cord, the function of the OPRK are related to learning and memory, emotional control, stress response and pain (Schwarzer 2009; Bruchas, Land et al. 2010; Butelman, Yuferov et al. 2012). OPRK agonists hold therapeutic potential for mood and addiction disorders, psychiatric co-morbidities, and pain management, but they also induce undesirable on-target side effects such as place aversion, dysphoria and anhedonia. On the other hand, OPRK antagonists hold therapeutic potential as antidepressants and anxiolytics, but may induce hyperalgic states. Recent elegant studies in rodents have mechanistically linked the activation of p38 MAPK to stress-mediated OPRK stimulation via the β-arrestin mediated transduction pathway (Bruchas, Macey et al. 2006; Bruchas, Land et al. 2007). In this frame, OPRK G-protein biased agonists were described as hypothetical analgesic drugs without aversive and dysphoric components (Chavkin 2011). In t study, noribogaine was found to be a partial agonist (70%) at the OPRK G-protein pathway. It also displayed profound functional bias and was not an agonist of the OPRK β-arrestin pathway. Therefore, noribogaine appears to carry the prerequisite pharmacological characteristics of analgesic kappa opioid drug devoid of aversive and dysphoric effects.

Only one ligand as so far been reported to be a G protein-biased OPRK agonist that poorly recruits β-arrestin (Rives, Rossillo et al. 2012). 6'-guanidinonaltrindole (6'-GNTI) acts as a β-arrestin antagonist in the presence of unbiased OPRK agonists, just as noribogaine does in the present study. However, noribogaine differs from 6'-GNTI in several aspects. Noribogaine was more biased than 6'-GNTI with a 2.4× stronger efficacy bias than 6'GNTI (70%-12%=0.59 versus 37%-12%=0.25) (Tables 4, 5). Noribogaine displayed an apparent functional coupling bias of 32× for activation ($EC_{50}$[G-protein]=8 μM vs $EC_{50}$[β-Arrestin]=265 nM) and 144× for inhibition ($K_e$[G-protein]=48 μM vs $K_e$[β-Arrestin]=262 nM) which was not observed for 6'GNTI. At a set concentration corresponding to physiological levels in the brain of rats (e.g. 5 μM) noribogaine tested in vitro preserved signaling of Dynorphin A to the G-protein pathway while markedly inhibiting dynorphin A-induced β-arrestin recruitment and thereby incurring functional selectivity to the otherwise unbiased endogenous agonist dynorphin A. This peculiar pharmacological property could contribute to anti-dysphoric activities against stress-induced, drug-activated or over-active dynorphin-kappergic system as seen during drug dependence, withdrawals, stress and anxiety related disorders.

Ligand-induced functional selectivity of otherwise unbiased agonists was previously demonstrated for some receptors of the GPCR family (i.e. the allosteric ligand LPI805 for the NK2 receptor (Maillet, Pellegrini et al. 2007). However, in the present study noribogaine does not appear to be an allosteric ligand and has many features of an OPRK orthosteric ligand: 1) it directly competed with the binding of orthosteric radiolabelled agonists DAMGO, U69,593; 2) it displayed functionally competitive behavior with certain antagonists and agonists; 3) it was docked to the morphiman orthosteric binding site of the OPRM inactive state in silico with a good stringency. The data provided herein suggest that noribogaine induces functional selectivity to dynorphin A via the interplay of a set of active and inactive conformational states. Certain conformations would be easily accessible to other agonists (the inactive conformations and active G-protein conformations) and other conformations would be energetically challenging to populate in the place of noribogaine (non-recruiting β-arrestin-2 receptor conformations). Indeed, multiple studies provide evidence for the existence of intermediate conformational states linking the inactive receptor to the fully active receptor and agonist binding and activation of GPCRs has been proposed to occur through a multistep process. The intermediate conformational states generated during multistep agonist binding may have unique functional properties as it is known that GPCR can couple to different G-proteins and also activate non-G protein dependent pathways. Interestingly, recent investigations in drug design described an allotropic binding mode for certain OPRK agonists, which encompassed sequential drug-receptor interaction mechanisms (Munro, Xu et al. 2013).

In conclusion, this study shows that noribogaine is a dual ligand of both mu and kappa opioid receptors (OPRM and OPRK) with peculiar pharmacological properties. Noribogaine displayed mixed agonism-antagonism properties and a profound G-protein bias at the opioid receptors. Noribogaine also incurred functional selectivity to the otherwise unbiased dynorphin A signaling and the kappa system. This study clarifies the mechanisms of noribogaine at modulating opioid receptor function, proposing explanatory mechanisms for the known modulatory properties of noribogaine at the opioid system in vivo as well as new avenues of therapeutic development and applicability.

All references cited are incorporated by reference herein in their entireties.

What is claimed is:

1. A method for potentiating the analgesic effect of an opioid analgesic in a patient undergoing or scheduled to undergo opioid analgesic therapy, the method comprising administering a potentiating amount of an iboga alkaloid or pharmaceutically acceptable salt and/or solvate thereof while maintaining a QT interval prolongation of less than about 60 milliseconds (ms) during said treatment thereby potentiating the effect of the opioid.

2. A method for preventing or reducing tolerance to an opioid analgesic in a patient undergoing or scheduled to undergo opioid analgesic therapy, the method comprising administering an effective amount of an iboga alkaloid or pharmaceutically acceptable salt and/or solvate thereof to prevent or reduce tolerance to the opioid while maintaining a QT interval prolongation of less than about 60 milliseconds (ms) during said treatment, thereby preventing or reducing tolerance to the opioid.

* * * * *